(12) United States Patent
Sin et al.

(10) Patent No.: US 7,166,744 B2
(45) Date of Patent: Jan. 23, 2007

(54) RETINOID DERIVATIVES AND METHODS FOR PRODUCING SAID COMPOUNDS AND ANTI-CANCER PHARMACEUTICAL COMPOSITION COMPRISING SAID COMPOUNDS

(75) Inventors: Hong-Sig Sin, Seoul (KR); Soo-Jong Um, Kyunggi-do (KR); Young-Soy Rho, Jeonlabuk-do (KR); Si-Ho Park, Jeonlabuk-do (KR); Youn-Ja Kwon, Kyunggi-do (KR); Myoung-Soon Park, Kyunggi-do (KR); Hye-Sook Han, Seoul (KR); So-Mi Kim, Cheju-do (KR); Dong-Myoung Kim, Seoul (KR); Deok-Kun Oh, Kyunggi-do (KR); Jong-Sup Park, Seoul (KR); Tae-Sung Bae, Jeonlabuk-do (KR)

(73) Assignee: Chebigen Co., Ltd., Seoul (KR)

( * ) Notice: Subject to any disclaimer, the term of this patent is extended or adjusted under 35 U.S.C. 154(b) by 182 days.

(21) Appl. No.: 10/239,001

(22) PCT Filed: May 29, 2002

(86) PCT No.: PCT/KR02/01014

§ 371 (c)(1),
(2), (4) Date: Sep. 17, 2002

(87) PCT Pub. No.: WO02/096857

PCT Pub. Date: Dec. 5, 2002

(65) Prior Publication Data

US 2003/0171339 A1 Sep. 11, 2003

(30) Foreign Application Priority Data

May 29, 2001 (KR) .......................... 2001-0029813
Mar. 20, 2002 (KR) .......................... 2002-0015016

(51) Int. Cl.
C07C 311/02 (2006.01)
C07C 233/01 (2006.01)

(52) U.S. Cl. .................. 564/88; 564/169; 564/217; 546/95; 514/294; 514/478; 514/490; 514/492; 514/502; 514/513; 514/419; 514/381

(58) Field of Classification Search .................. 564/88, 564/169, 217; 546/95; 514/294, 478, 490, 514/492, 502, 513, 419, 381
See application file for complete search history.

(56) References Cited

U.S. PATENT DOCUMENTS

| 4,087,409 A | 5/1978 | Preston |
| 4,266,056 A | 5/1981 | Henrick et al. |
| 4,281,138 A | 7/1981 | Shetty et al. |
| 4,310,546 A | 1/1982 | Gander |
| 4,595,696 A * | 6/1986 | Loev et al. |
| 5,047,066 A | 9/1991 | Mano et al. |

FOREIGN PATENT DOCUMENTS

| EP | 30009 A1 | 6/1981 |
| EP | 124877 A2 | 11/1984 |
| EP | 261911 A2 | 3/1988 |
| GB | 1449027 A | 9/1976 |
| WO | WO 83/02558 | 8/1983 |
| WO | WO 91/01128 | * 2/1991 |
| WO | WO 91/01301 | * 2/1991 |

OTHER PUBLICATIONS

Clifford et al., "Effects of Novel Phenylretinamides on Cell Growth and Apoptosis in Bladder Cancer", Cancer Epidemiology, Biomarkers & Prevention, Apr. 2001, 10(4):391-395.
Swanson et al., "Biotransformation and Biological Activity of N-(4-Hydroxyphenyl) Retinamide Derivatives in Rodents," J. Pharmacology and Experimental Therapeutic, 1981, 219(3):632-637.
Landsteiner, K. and Scheer, J., "Serological Studies on Azoproteins," J. Experimental Medicine, 1934, 59:751-768.
Yang-Yen, H.F. et al., Antagonism Between Retinoic Acid Receptors ~, New Biologist, 1991; 3:1206-1219.
Hathcock J.N. et al., Evaluation of vitamin A Toxicity, Am.J.Clin. Nutr., 1990; 52:183-202.
Angel, P. et al., Phorbol Ether-Inducible Genes Contain a Common Cis Element ~, Cell, 1987; 49: 729-739.
Ryseck, R.P. et al., Transcriptional activation of c-jun ~, Nature, 1988; 334:535-537.
Angel, P. and Karin M., The role of Jun, Fos and the Ap-1 complex ~, Biochimica at Biophysica Acta, 1991; 1072:129-157.
Muller, J.M. et al., Study of Gene Regulation ~, Methods: A Companion to Methods in Enzymology, 1997; 11:301-312.

(Continued)

*Primary Examiner*—Elvis O. Price
(74) *Attorney, Agent, or Firm*—JHK Law; Joseph Hyosnk Kim

(57) ABSTRACT

The present invention relates to a novel retinoid derivative compound represented by the formula I:

(I)

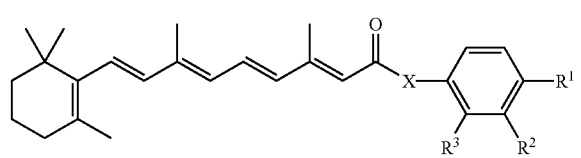

wherein X, $R^1$, $R^2$ and $R^3$ are as defined herein or pharmaceutically acceptalbe salts thereof. Also, the present invention relates to processes for producing the compound of the formula I and to an anti-cancer composition comprising the compound of the formula I. The compound of the formula I according to the present invention exerts high anti-cancer effects while not causing undesirable side effects.

17 Claims, 15 Drawing Sheets

OTHER PUBLICATIONS

Bernstein, L.R. and C olburn N.H., AP1/jun Function is Differentially Induced ~, Science, 1989; 244:566-569.

Barthelman, M. et. al., Inhibitory Effects of Perillyl Alcohol ~, Cancer Res., 1998; 58:711-716.

McDonnell, S. and Matrisian L.M., Stromelysin in tumor progression and metastasis, Cancer Metastasis Rev., 1990; 9:305-319.

Crawford, H.C. and Matrisian L.M., Mechanisms Controlling the Transcription ~, Enzyme Protein, 1996; 49:20-37.

* cited by examiner

HCT116

MCF-7

(A) HCT116

(B) MCF-7

2.5 μM 5.0 μM

10 μM (A) HCT116

(B) MCF-7

- ■ HPR
- ▲ KCBG10
- ◆ KCBG40
- ● KCBG41

(A)

(B)

Control(DMSO)

ATRA(10μM)

HPR(10μM)

KCBG60(10μM)

B(10μM)

RETINOID DERIVATIVES AND METHODS FOR PRODUCING SAID COMPOUNDS AND ANTI-CANCER PHARMACEUTICAL COMPOSITION COMPRISING SAID COMPOUNDS

CONTINUING DATA

This application is a national stage application of PCT/KR02/01014, filed May 29, 2002 under 35 U.S.C. §371.

TECHNICAL FIELD

The present invention relates to novel retinoid derivatives or pharmaceutically acceptable salts thereof having anti-cancer activity, processes for producing said compounds and anti-cancer pharmaceutical compositions comprising said compounds as an active ingrediant.

BACKGROUND ART

There have been developed many particular chemical substances for the prevention and treatment of cancer. Representative examples of such anti-cancer substances include vitamin A (retinol) and retinoids. U.S. Pat. No. 4,310,546 discloses N-(4-acyloxyphenyl)-all-trans-retinamide, U.S. Pat. No. 4,323,581 discloses N-(4-hydroxyphenyl)-all-trans-retinamide, and U.S. Pat. No. 4,665,098 discloses N-(4-hydroxyphenyl) retinamide known as fenretimide.

Retinoids are involved in cell differentiation and individual development by binding to RAR(retinoic acid receptor) or RXR(retinoid X receptor), which exist in a nucleus of a cell, to assist transcriptional activity of RAR/RXR. These compounds are known to exert anti-cancer effects by indirectly interacting with the transcriptional activator, AP-1 (activation protein-1) and inhibiting activity of AP-1 to prevent the expression of a target gene of AP-1, which is involved in the development and metastasis of cancer (Yang-Yen H. F., et al., New Biol. 3:1206–1219, 1991). It is also known that retinols and retinoids suppress imprudent proliferation of cells and induce differentiation or apoptosis and thus will be potentially used for the prevention and treatment of cancer (Hong W. K. and Itri L. M., Biol. Chem. Med., 2nd ed. edited by Sporn et al., New York: Raven Press; 597–630, 1994). However, the therapeutic use of retinoids has been restricted because these compounds would be accompanied by undesirable side effects, for example skin irritation, toxication on organis, and deformation of organs, occurred by some of proteins activated by binding retinoids to their receptors, (Hathcock J. N., et al., Am. J. Clin. Nutr., 52, 183–202, 1990).

Recently, several retinoid derivatives have been found to exhibit improved anti-cancer efficacy over prior retinoids but show reduced side effects. U.S. Pat. No. 6,117,845 discloses anti-cancer compounds represented by the formula:

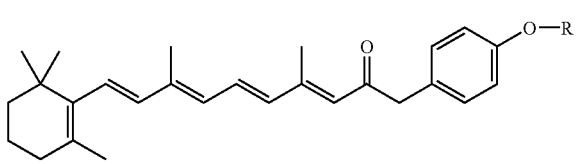

Also, U.S. Pat. No. 6,274,742 discloses N-homocysteine thiolactonyl retinamide compounds represented by the formula:

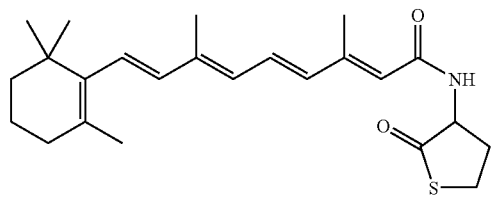

Some of the foregoing compounds are demonstrated to have relatively excellent anti-cancer effects with low side effects and are under clinical trials. Such representative examples include N-(4-hydroxyphenyl)-all-trans-retinamide compounds. However, even N-(4-hydroxyphenyl)-all-trans-retinamide compounds do not fulfill requirements for a anti-cancer drug in that these compounds stimulate tissues when being orally administered at a high dose, which would be an inherent problem of retinoid family drugs.

DISCLOSURE OF INVENTION

Therefore, it is an object of the present invention is to provide novel retinoid derivatives that are structurally different from and exeret increased anti-cancer effects but reduced undesirable side effects over retinoid compounds known heretofore.

In accordance with one aspect of the present invention, there are provided a retinamide compound represented by the formula I:

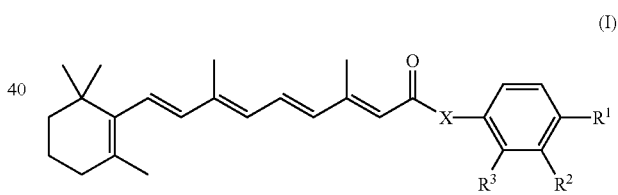

wherein (i) X is O, NH or S; $R^1$ and $R^2$, which may be identical or different, are each independently —OH, —SH, —NH$_2$, —COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each R is CH$_2$, O, NH or S, $R^4$ is H or $C_{1-6}$ alkyl, and each m is an integer of 0 to 5; and $R^3$ is H;

(ii) X is the same as defined above; $R^1$ and $R^3$, which may be identical or different, are each independently —OH, —SH, —NH$_2$, —COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each R is CH$_2$, O, NH or S, $R^4$ is H or $C_1$–$C_6$ alkyl, and each m is an integer of 0 to 5; and $R^2$ is H;

(iii) X is the same as defined above; R¹ is —OH, —SH, —NH₂, —COOH, —R(CH₂)$_m$CH₃, —RCOCO(CH₂)$_m$CH₃, —RCO(CH₂)$_m$CHCH₃CH₃, —RCO(CH₂)$_m$NR⁴CH₃, —RCOCHOH(CH₂)$_m$CH₃, —RCOCH₂(CH₂)$_m$CH₃, —RCOCH₂CHOH(CH₂)$_m$CH₃, —RCOCH₂(CH₂)$_m$COOH, —RSO₂CH₂(CH₂)$_m$CH₃, —RPO₂(OH)CH₂(CH₂)$_m$CH₃ or RCOCH(NHCOCH₃)CH₂CH₂CONH₂, in which each R is CH₂, O, NH or S, R⁴ is H or C₁–C₆ alkyl, and each m is an integer of 0 to 5; R² is H; and R³ is H, OH or Cl;

(iv) X is the same as defined above; R³ is —OH, —SH, —NH₂, —COOH, —R(CH₂)$_m$CH₃, —RCOCO(CH₂)$_m$CH₃, —RCO(CH₂)$_m$CHCH₃CH₃, —RCO(CH₂)$_m$NR⁴CH₃, —RCOCHOH(CH₂)$_m$CH₃, —RCOCH₂(CH₂)$_m$CH₃, —RCOCH₂CHOH(CH₂)$_m$CH₃, —RCOCH₂(CH₂)$_m$COOH, —RSO₂CH₂(CH₂)$_m$CH₃, —RPO₂(OH)CH₂(CH₂)$_m$CH₃ or RCOCH(NHCOCH₃)CH₂CH₂CONH₂, in which each R is CH₂, O, NH or S, R⁴ is H or C₁–C₆ alkyl, and each m is an integer of 0 to 5; R² is H; and R¹ is H, OH or Cl; or (v) X is the same as defined above; R¹, R² and R³, which may be identical or different, are each independently —OH, —SH, —NH₂, —COOH, —R(CH₂)$_m$CH₃, —RCOCO(CH₂)$_m$CH₃, —RCO(CH₂)$_m$CHCH₃CH₃, —RCO(CH₂)$_m$NR⁴CH₃, —RCOCHOH(CH₂)$_m$CH₃, —RCOCH₂(CH₂)$_m$CH₃, —RCOCH₂CHOH(CH₂)$_m$CH₃, —RCOCH₂(CH₂)$_m$COOH, —RSO₂CH₂(CH₂)$_m$CH₃, —RPO₂(OH)CH₂(CH₂)$_m$CH₃ or RCOCH(NHCOCH₃)CH₂CH₂CONH₂, in which each R is CH₂, O, NH or S, R⁴ is H or C₁–C₆ alkyl, and each m is an integer of 0 to 5; and pharmaceutically acceptable salts thereof.

In accordance with another aspect of the present invention, there is provided processes for producing the above compound of the formula I.

In accordance with further aspect of the present invention, there is provided an anti-cancer composition comprising a therapeutically effective amount of the above compound of the formula I and a pharmaceutically acceptable carrier.

BRIEF DESCRIPTION OF THE DRAWINGS

The above and other objects, features and other advantages of the present invention will be more clearly understood from the following detailed description taken in conjuction with the accompanying drawings.

BEST MODE FOR CARRYING OUT THE INVENTION

Figure 1:
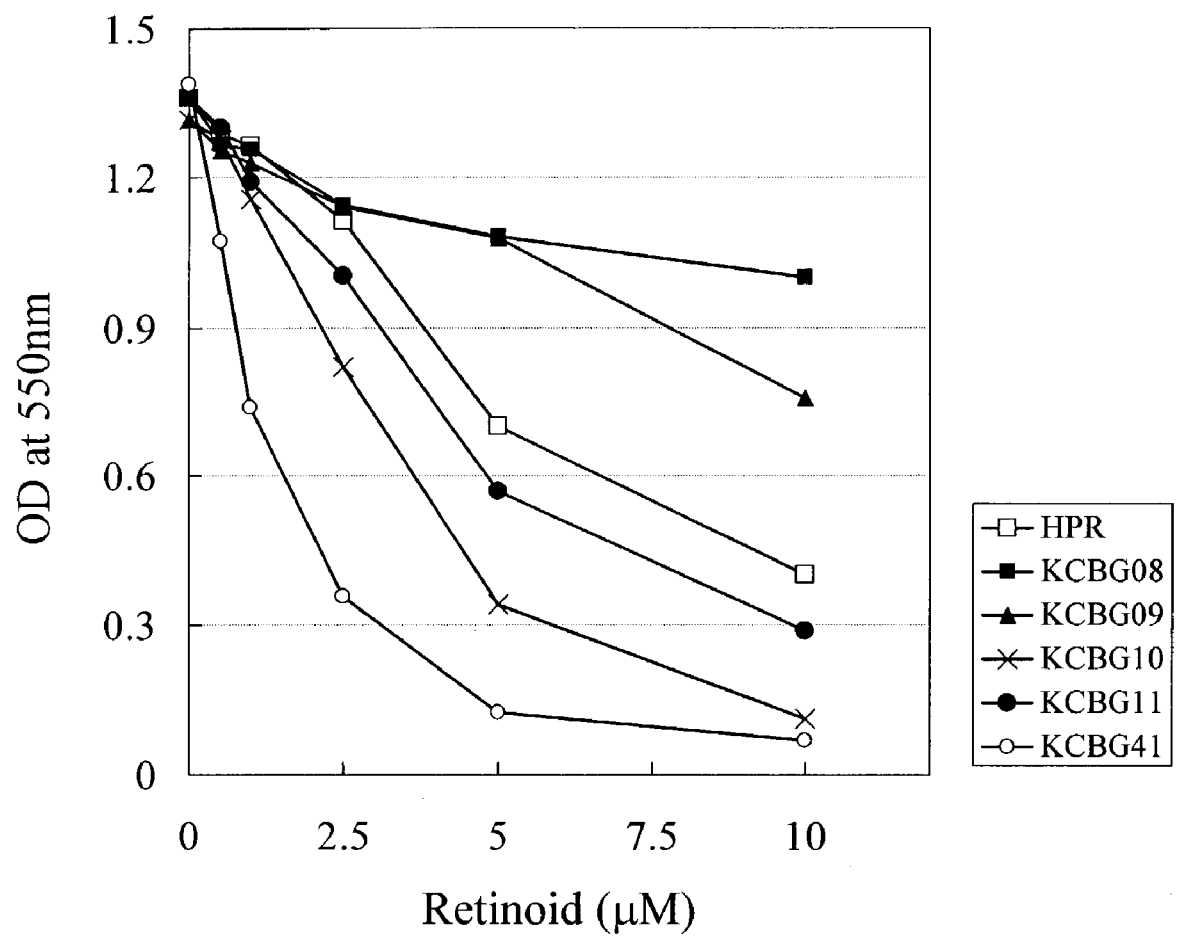
FIG. 1 is the results of an MTT assay on the effects of various retinoid derivatives on proliferation of colon cancer cells HCT116 48 hours after being treated with the respective retinoid derivatives at different concentrations.

In the first embodiment, the retinamide derivatives according to the present invention include a compound of the formula Ia:

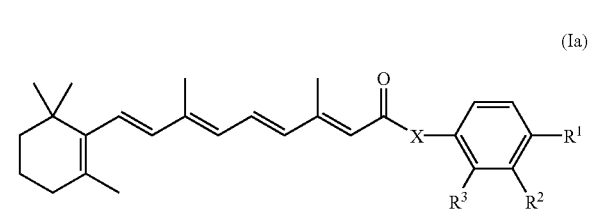

(Ia)

wherein

X is O, NH or S;

R¹ and R², which may be identical or different, are each independently —OH, —SH, —NH₂, —COOH, —R(CH₂)$_m$CH₃, —RCOCO(CH₂)$_m$CH₃, —RCO(CH₂)$_m$CHCH₃CH₃, —RCO(CH₂)$_m$NR⁴CH₃, —RCOCHOH(CH₂)$_m$CH₃, —RCOCH₂(CH₂)$_m$CH₃, —RCOCH₂$_{CH}$OH(CH₂)$_m$CH₃, —RCOCH₂(CH₂)$_m$COOH, —RSO₂CH₂(CH₂)$_m$CH₃, —RPO₂(OH)CH₂(CH₂)$_m$CH₃ or RCOCH(NHCOCH₃)CH₂CH₂CONH₂, in which each R is CH₂, O, NH or S, R⁴ is H or C₁–C₆ alkyl, and each m is an integer of 0 to 5; and $R^3$ is H.

In the second embodiment, the retinamide derivatives include a compound of the formula Ib:

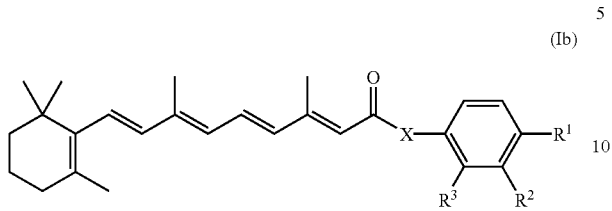

(Ib)

wherein
X is O, NH or S;
$R^1$ and $R^3$, which may be identical or different, are each independently —OH, —SH, —NH$_2$, —COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2{}_{CH}$OH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each R is CH$_2$, O, NH or S, $R^4$ is H or $C_1$–$C_6$ alkyl, and each m is an integer of 0 to 5; and
R is H.

In the third embodiment, the retinamide derivatives according to the present invention include a compound of the formula Ic:

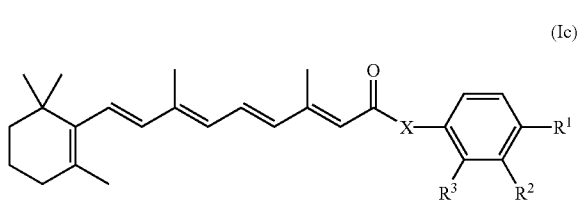

(Ic)

wherein
X is O, NH or S;
$R^1$ is —OH, —SH, —NH$_2$, —COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each R is CH$_2$, O, NH or S, $R^4$ is H or $C_1$–$C_6$ alkyl, and each m is an integer of 0 to 5;
$R^2$ is H; and
$R^3$ is H, OH or Cl.

In the fourth embodiment, the retinamide derivatives according to the present invention include a compound of the formula Id:

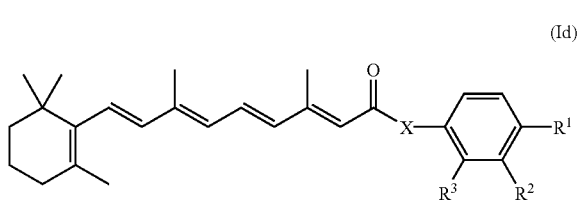

(Id)

wherein
X is O, NH or S;
$R^1$ is H, OH or Cl;
$R^2$ is H; and
$R^3$ is —OH, —SH, —NH$_2$, —COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each R is CH$_2$, O, NH or S, $R^4$ is H or $C_1$–$C_6$ alkyl, m is an integer of 0 to 5.

In the fifth embodiment, the retinamide derivatives according to the present invention include a compound of the formula Ie:

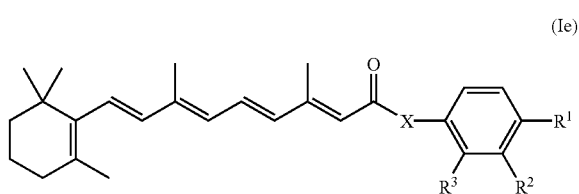

(Ie)

wherein
X is O, NH or S;
$R^1$, $R^2$ and $R^3$, which may be identical or different, are each independently —OH, —SH, —NH$_2$, —COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each R is CH$_2$, O, NH or S, $R^4$ is H or $C_1$–$C_6$ alkyl, and each m is an integer of 0 to 5.

Preferred examples of the retinoid derivatives according to the present invention include:

2.2-[(2E,4E,6E,8E)-3,7-dimethyl-9-(2,6,6-trimethyl-cyclohex-1-enyl)-nona-2,4,6,8-tetraenoylamino]-5-hydroxyphenyl butanoate (KCBG10);

5-butyryloxy-2-[3,7-dimethyl-9-(2,6,6-trimethyl-cyclohex-1-enyl)-nona-2,4,6,8-tetraenoylamino]-phenyl butanoate (KCBG09);

2-[(2E,4E,6E,8E)-3,7-dimethyl-9-(2,6,6-trimethyl-cyclohex-1-enyl)-nona-2,4,6,8-tetraenoylamino]-5-hydroxyphenyl propionate (KCBG15);

2-[(2E,4E,6E,8E)-3,7-dimethyl-9-(2,6,6-trimethyl-cyclohex-1-enyl)-nona-2,4,6,8-tetraenoylamino]-5-hydroxyphenyl-2-oxo-propionate (KCBG22);

2-[(2E,4E,6E,8E)-3,7-dimethyl-9-(2,6,6-trimethyl-cyclohex-1-enyl)-nona-2,4,6,8-tetraenoylamino]-5-hydroxyphenyl-(dimethylamino)-acetate (KCBG23);

4-(4-[(2E,4E,6E,8E)-3,7-dimethyl-9-(2,6,6-trimethyl-1-cyclohexenyl)-2,4,6,8-nonatetraenoyl]aminophenoxy)-4-oxobutanoic acid (KCBG32);

2-butyryloxy-5-(2E,4E,6E,8E)-[3,7-dimethyl-9-(2,6,6-trimethyl-cyclohex-1-enyl -nona -2,4,6,8-tetraenoylamino]-phenyl butanoate (KCBG34);

5-(2E,4E,6E,8E)-[3,7-dimethyl-9-(2,6,6-trimethyl-cyclohex-1-enyl)-nona-2,4,6,8-tetraenoylamino]-2-hydroxyphenyl butanoate (KCBG35);

2-[(2E,4E,6E,8E)-3,7-dimethyl-9-(2,6,6-trimethyl-cyclohex-1-enyl)-nona-2,4,6,8-tetraenoylamino]-5-hydroxyphenyl-2-oxobutanoate (KCBG38);

2-[(2E,4E,6E,8E)-3,7-dimethyl-9-(2,6,6-trimethyl-cyclohex-1-enyl)-nona-2,4,6,8-tetraenoylamino]-5-hydroxyphenyl-3-hydroxy-butanoate (KCBG39);

(2E,4E,6E,8E)-[3,7-dimethyl-9-(2,6,6-trimethyl-cyclohex-1-enyl)-nona-2,4,6,8-tetraenoylamino]-(4-butyrylamino)-phenylamide (KCBG40);

(2E,4E,6E,8E)-[3,7-dimethyl-9-(2,6,6-trimethyl-cyclohex-1-enyl)-nona-2,4,6,8-tetraenoylamino]-(3-butylamino-4-hydroxy)-phenylamide (KCBG41);

4-[(2E,4E,6E,8E)-3,7-dimethyl-9-(2,6,6-trimethyl-1-cyclohexenyl)-2,4,6,8-nonatetraenoyl]aminophenyl-1-butanesulfonate (KCBG43);

4-[(2E,4E,6E,8E)-3,7-dimethyl-9-(2,6,6-trimethyl-1-cyclohexenyl)-2,4,6,8-nonatetraenoyl]aminophenyl-2-oxopropanoate (KCBG45);

4-[(2E,4E,6E,8E)-3,7-dimethyl-9-(2,6,6-trimethyl-1-cyclohexenyl)-2,4,6,8-nonatetraenoyl]aminophenyl-2-oxobutanoate (KCBG47);

4-(4-[(2E,4E,6E,8E)-3,7-dimethyl-9-(2,6,6-trimethyl-1-cyclohexenyl)-2,4,6,8-nonatetraenoyl]aminophenoxy)-4-oxobutanoic acid (KCBG50);

4-(4-[(2E,4E,6E,8E)-3,7-dimethyl-9-(2,6,6-trimethyl-1-cyclohexenyl)-2,4,6,8-nonatetraenoyl]aminophenoxy)-oxohexandioic acid (KCBG51);

4-[(2E,4E,6E,8E)-3,7-dimethyl-9-(2,6,6-trimethyl-cyclohex-1-enyl)-nona-2,4,6,8-tetraenoylamino]-phenyl-2-acetylamino-4-carbamoyl butanoate (KCBG52);

4-(4-[(2E,4E,6E,8E)-3,7-dimethyl-9-(2,6,6-trimethyl-1-cyclohexenyl)-2,4,6,8-nonatetraenoyl]aminophenoxy)-oxopeptandioic acid (KCBG53);

4-(4-[(2E,4E,6E,8E)-3,7-dimethyl-9-(2,6,6-trimethyl-1-cyclohexenyl)-2,4,6,8-nonatetraenoyl]aminophenoxy)-oxooctandioic acid (KC BG54); and 4-[(2E,4E,6E,8E)-3,7-dimethyl-9-(2,6,6-trimethyl-1-cyclohexenyl)-2,4,6,8-nonatetraenoyl]aminophenyl butanoate (KCBG60).

The retinoid compound of the formula I according to the present invention can be prepared by reacting retinoic acid with a compound of the formula II:

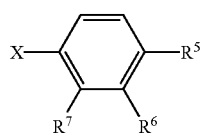

(II)

wherein X is OH, $NH_2$ or SH; and $R^5$ and $R^6$ are each independently OH, $NH_2$ or SH and $R^7$ is H or Cl for the preparation of the above class (i) of the compounds of the formual I; $R^5$ and $R^7$ are each independently OH, $NH_2$ or SH and $R^6$ is H for the preparation of the above class (ii) of the compounds of the formual I; $R^5$ is OH, $NH_2$ or SH, $R^6$ is H and $R^7$ is H, OH or Cl for the preparation of the above class (iii) of the compounds of the formual I; $R^5$ is H, OH or Cl, $R^6$ is H and $R^7$ is OH, $NH_2$ or SH for the preparation of the above class (iv) of the compounds of the formual I; or $R^5$, $R^6$ and $R^7$ are each independently OH, $NH_2$ or SH for the preparation of the above class (v) of the compounds of the formual I to form a compound of the formula III:

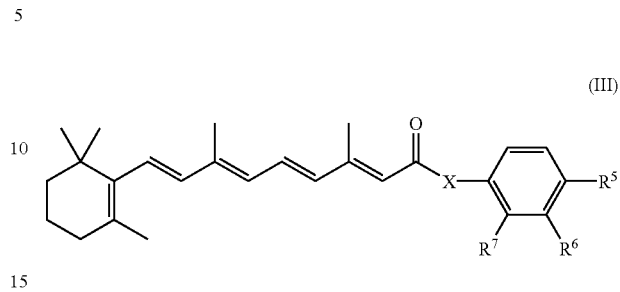

(III)

wherein X, $R^5$, $R^6$ and $R^7$ are the same as defined above, and reacting the compound of the formula III with a compound of the formula IV:

W—Y  (IV)

wherein W is —OH, —SH, —$NH_2$, —COOH, —R($CH_2$)$_m$$CH_3$, —RCOCO($CH_2$)$_m$$CH_3$, —RCO($CH_2$)$_m$CHCH$_3$CH$_3$, —RCO($CH_2$)$_m$NR$^4$CH$_3$, —RCOCHOH($CH_2$)$_m$CH$_3$, —RCOCH$_2$($CH_2$)$_m$CH$_3$, —RCOCH$_2$CHOH ($CH_2$)$_m$CH$_3$, —RCOCH$_2$($CH_2$)$_m$COOH, —RSO$_2$CH$_2$($CH_2$)$_m$CH$_3$, —RPO$_2$(OH)CH$_2$($CH_2$)$_m$CH$_3$ or —RCOCH(NCOCH$_3$)CH$_2$CH$_2$CONH$_2$; and Y is OH or Cl, to form the above compound of the formula I.

Alternatively, the retinoid compound of the formula I according to the present invention can be prepared by reacting a compound of the formula II:

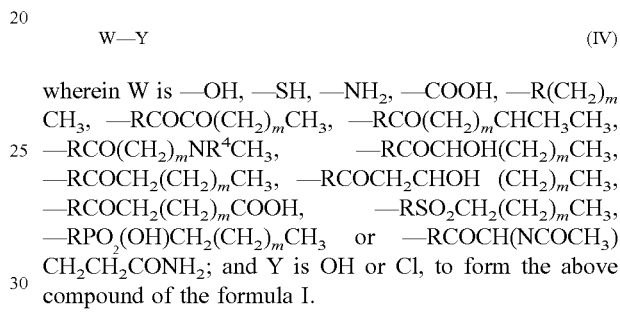

(II)

wherein X, $R^5$, $R^6$ and $R^7$ are the same as defined above with a compound of the formula IV:

W—Y  (IV)

wherein W and Y are the same as defined above, to form a compound of the formula V:

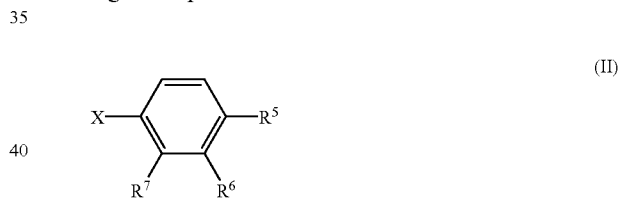

(V)

wherein X, $R^1$, $R^2$ and $R^3$ are the same as defined above and reacting the compound of the formula V with retinoic acid to form the above compound of the formula I.

As a class of the retinoid compounds of the formula I according to the present invention, the compound represented by the formula Ia:

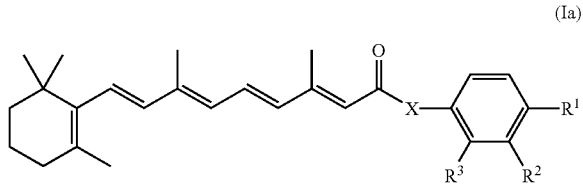

(Ia)

wherein X is OH, $NH_2$ or SH; $R^1$ and $R^3$ are each independently —OH, —SH, —$NH_2$, —COOH, —$R(CH_2)_mCH_3$, —$RCOCO(CH_2)_mCH_3$, —$RCO(CH_2)_mCHCH_3CH_3$, —$RCO(CH_2)_mNR^4CH_3$, —$RCOCHOH(CH_2)_mCH_3$, —$RCOCH_2(CH_2)_mCH_3$, —$RCOCH_2CHOH(CH_2)_mCH_3$, —$RCOCH_2(CH_2)_mCOOH$, —$RSO_2CH_2(CH_2)_mCH_3$, —$RPO_2(OH)CH_2(CH_2)_mCH_3$ or $RCOCH(NHCOCH_3)CH_2CH_2CONH_2$, in which each R is O, NH or S, $R^4$ is H or $C_1$–$C_6$ alkyl, and each m is an integer of 0 to 5; R2 is H can be prepared by reacting a compound of the formula IIIa:

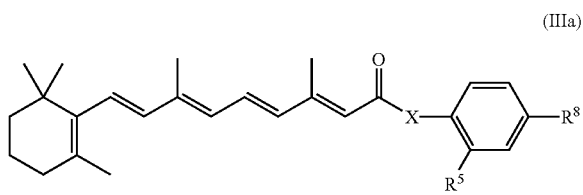

(IIIa)

wherein $R^5$ is OH, $NH_2$ or SH; and $R^8$ is OH or SH with a compound of the formula IV:

W—Y (IV)

wherein W is —$RCOCO(CH_2)_mCH_3$, —$RCO(CH_2)_mCHCH_3CH_3$, —$RCO(CH_2)_mNR^4CH_3$, —$RCOCHOH(CH_2)_m CH_3$, —$RCOCH_2(CH_2)_mCH_3$, —$RCOCH_2CHOH(CH_2)_m CH_3$, —$RCOCH_2(CH_2)_mCOOH$, or $RCOCH(NHCOCH_3)CH_2CH_2CONH_2$; and Y is OH or Cl to form a compound of the formula Ib:

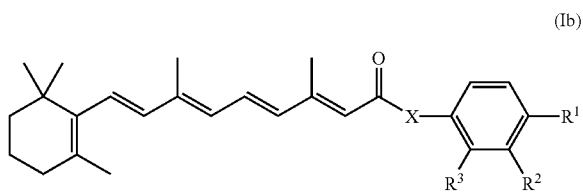

(Ib)

wherein X, $R^1$, $R^2$ and $R^3$ are the same as defined above, and deesterifying the compound of the formula Ib to yield the above compound of the formula Ia.

As another class of the retinoid compounds of the formula (I) according to the present invention, the compound represented by the formula Ic:

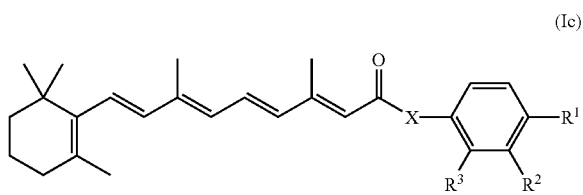

(Ic)

wherein X is O, NH or S; $R^1$ is —OH, —SH, —$NH_2$, —COOH, —$R(CH_2)_mCH_3$, —$RCOCO(CH_2)_mCH_3$, —$RCO(CH_2)_mCHCH_3CH_3$, —$RCO(CH_2)_mNR^4CH_3$, —$RCOCHOH(CH_2)_mCH_3$, —$RCOCH_2(CH_2)_mCH_3$, —$RCOCH_2CHOH(CH_2)_mCH_3$, —$RCOCH_2(CH_2)_mCOOH$, —$RSO_2CH_2(CH_2)_mCH_3$, —$RPO_2(OH)CH_2(CH_2)_mCH_3$ or $RCOCH(NHCOCH_3)CH_2CH_2CONH_2$, in which each R is $CH_2$, O, NH or S, $R^4$ is H or $C_1$–$C_6$ alkyl, and each m is an integer of 0 to 5; $R^2$ is H; and $R^3$ is H, OH or Cl can be prepared by reacting a compound of the formula IIa:

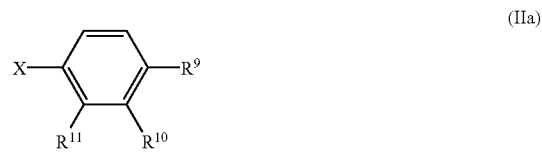

(IIa)

wherein X is the same as defined above; and $R^9$ and $R^{10}$ are each independently —$R(CH_2)_mCH_3$ and $R^{11}$ is H; $R^9$ and $R^{11}$ are each independently —$R(CH_2)_mCH_3$ and $R^{10}$ is H; $R^9$ is —$R(CH_2)_mCH_3$, $R^{10}$ is H and $R^{11}$ is H, OH or Cl; $R^9$ is H, OH or Cl, $R^{10}$ is H and $R^{11}$ is —$R(CH_2)_mCH_3$; or $R^9$, $R^{10}$ and $R^{11}$ are each independently —$R(CH_2)_mCH_3$, in which each R is $CH_2$, O, NH or S and each m is an integer of 0 to 5 with retinoic acid to yield the above compounds of the formula Ic.

Processes for producing the compound of the formula I according to the present invention include binding between aromatic derivatives and retinoic acid, esterification and deesterification. These reactions can be performed under conditions commonly used in the art of the organic chemistry. For example, the reaction of retinoic acid with an aromatic derivative can be performed in the presence of a condensing agent. Useful condensing agents include, but are not limited to, 4-amino N,N'-dicyclohexylcarbodiimide (DCC), 1-(3-dimethylaminopropyl)-3-ethylcarbodiimide hydrochloride (EDCI), N,N'-carbonylimidazol (CDI), N,N'-sulfuryldiimidazol (SDI), dimethylsulfoxide (DMSO) and $SO_2Cl$ (U.S. Pat. No. 5,399,757 and M. K. Dhaon, et al., J. Org. Chem. 1982, 47, 1962–1965). A catalyst used to promote the condensation includes, but is not limited to, N,N'-dimethylaminopyridine (DMAP). The esterification can be carried out using EDCI or DCC (Gibson, F. S., et al., J. Org. Chem, 1994, 59, 7503–7507; and Kulikov, N. V., J. Int. J. Dept. Prot. Res. 1993, 42, 20), N-methylmorphorine (NMM) or triethylamine (TEA) (Torres, J. L., et al., Tetrahedron 1987, 43, 4031–4034). The deesterification can be performed in $K_2CO_3$ and methanol (U.S. Pat. No. 5,863,942). All the foregoing reactions can be performed at room temperature.

In addition to those described above, any bases, condensing agents, catalysts and solvents well known to those skilled in the art can be used in processes of the present invention as long as they do not reversely affect the reactions.

The following reaction schemes 1 to 3 illustrate processes for producing resorcinol derivatives, catechol derivatives and HPR derivatives, all of which belong to the retinoid derivatives according to the present invention.

Reaction Scheme 1.
Preparation Of Resorcinol Derivatives
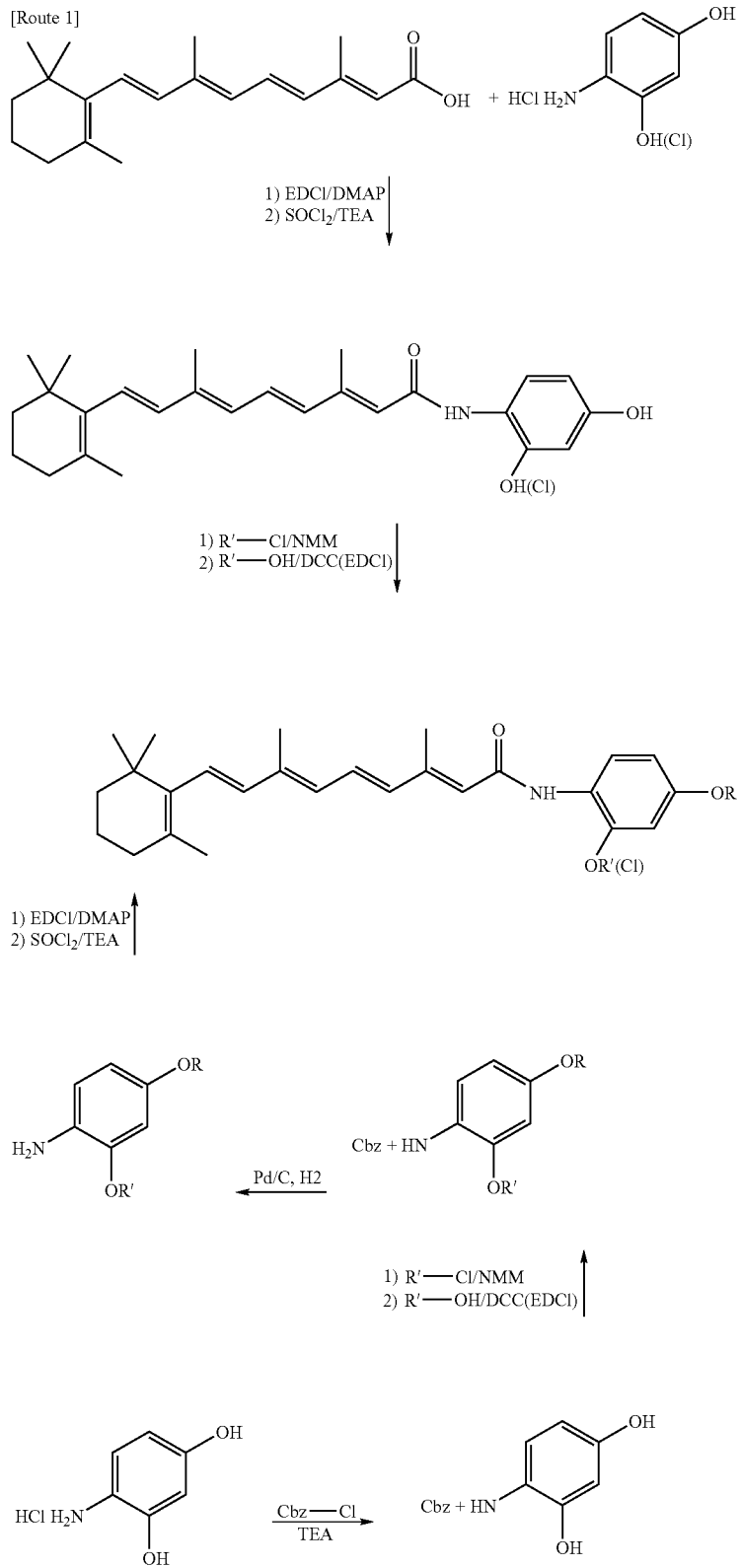

wherein each R is H and each R' is COCOCH$_3$, COCOCH$_2$CH$_3$, CO(CH$_2$)$_n$CH$_3$ in which n is 1, 2 or 3, COCH$_2$N(CH$_3$)$_2$, COCH$_2$CH(OH)CH$_3$ or COCH$_2$CH$_2$COOH; or R and R' are each represently COCOCH$_2$CH$_3$, CO(CH$_2$)$_n$CH$_3$ in which n is 1, 2 or 3 or COCH$_2$N (CH$_3$)$_2$.

[Route 2]

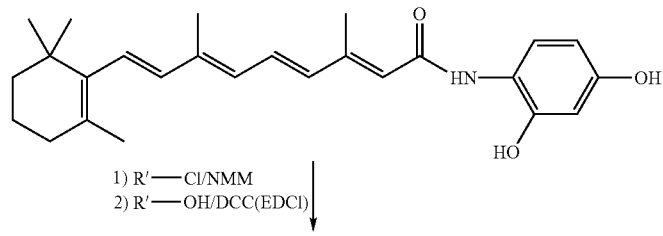

1) R'—Cl/NMM
2) R'—OH/DCC(EDCl)

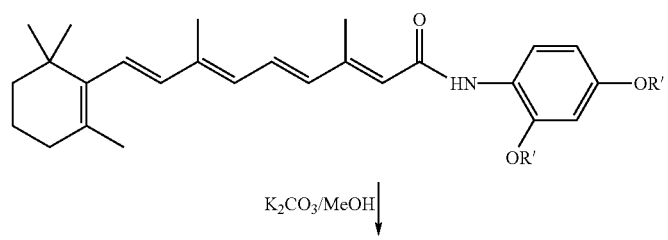

K$_2$CO$_3$/MeOH

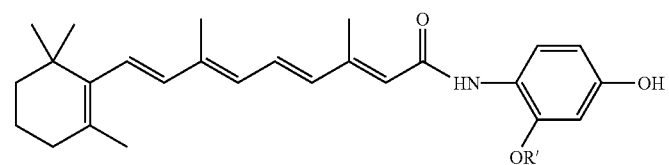

wherein each R' is COCH$_2$CH$_2$CH$_3$, CO(CH$_2$)$_n$CH$_3$ in which n is 1, 2 or 3 or COCH$_2$N (CH$_3$)$_2$.

Reaction Scheme 2.
Preparation Of Catechol Derivatives

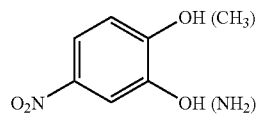

1) R'—Cl/NMM
2) R'—OH/DCC(EDCl)

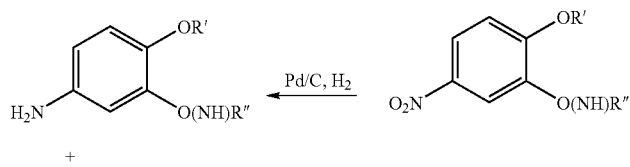

Pd/C, H$_2$

+

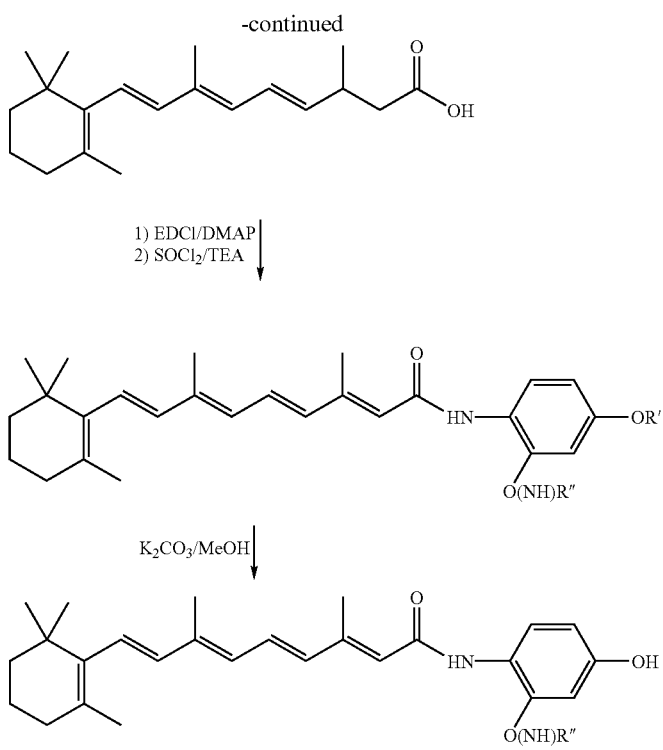

wherein R' is CH₃ and R" is COCH₂CH₂CH₃; R' is COCH₂CH₂CH₃ and R" is COCH₂CH₂CH₃; or R' is H and R" is COCH₂CH₂CH₃.

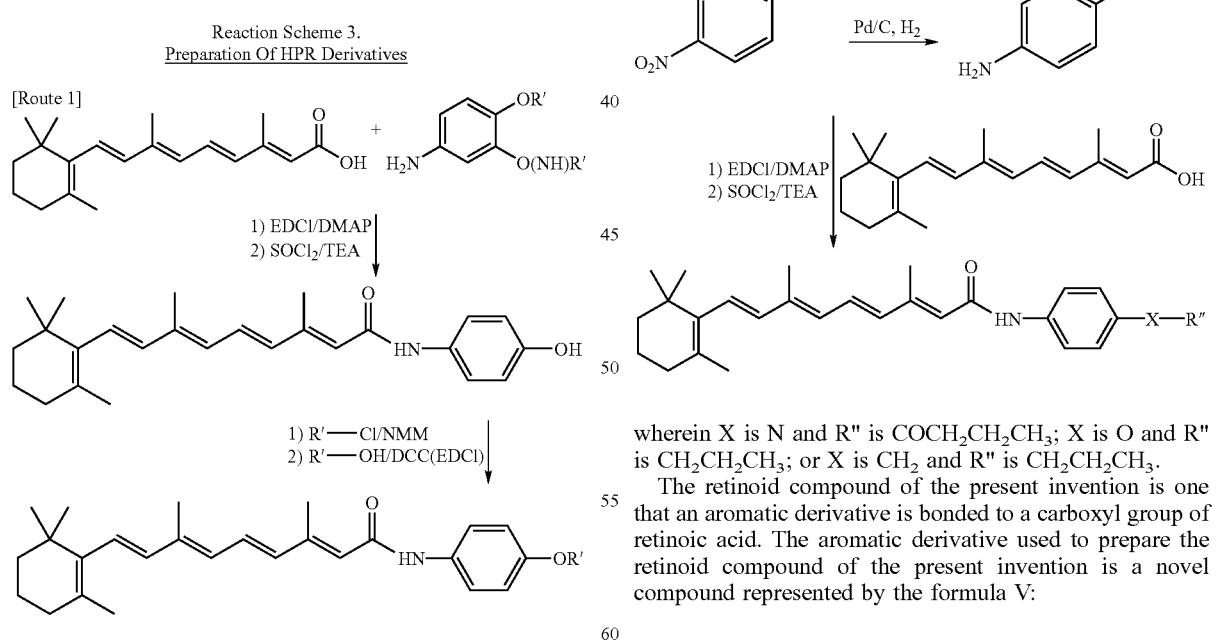

wherein each R' is COCOCH₃, COCOCH₂CH₃, CO(CH₂)$_n$CH₃ in which is n 1, 2 or 3, COCH₂CH(OH)CH₃, COCH₂N(CH₃)₂, CO₂(CH₂)$_n$COOH in which n is an integer of 2 to 6, SO₂(CH₂)$_n$CH₃ in which n is 2 or 3, PO₂(OH)(CH₂)$_n$CH₃ in which n is 2 or 3 or COCH(NHCOCH₃)CH₂CH₂CONH₂.

wherein X is N and R" is COCH₂CH₂CH₃; X is O and R" is CH₂CH₂CH₃; or X is CH₂ and R" is CH₂CH₂CH₃.

The retinoid compound of the present invention is one that an aromatic derivative is bonded to a carboxyl group of retinoic acid. The aromatic derivative used to prepare the retinoid compound of the present invention is a novel compound represented by the formula V:

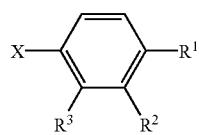

(V)

wherein X is OH, $NH_2$ or SH; (i) $R^1$ and $R^2$, which may be identical or different, are each independently —OH, —SH, —$NH_2$, —COOH, —$R(CH_2)_mCH_3$, —$RCOCO(CH_2)_mCH_3$, —$RCO(CH_2)_mCHCH_3CH_3$, —$RCO(CH_2)_mNR^4CH_3$, —$RCOCHOH(CH_2)_mCH_3$, —$RCOCH_2(CH_2)_mCH_3$, —$RCOCH_2CHOH(CH_2)_mCH_3$, —$RCOCH_2(CH_2)_mCOOH$, —$RSO_2CH_2(CH_2)_mCH_3$, —$RPO_2(OH)CH_2(CH_2)_mCH_3$ or $RCOCH(NHCOCH_3)CH_2CH_2CONH_2$, in which each R is $CH_2$, O, NH or S, $R^4$ is H or $C_1$–$C_6$ alkyl, and each m is an integer of 0 to 5; and $R^3$ is H; (ii) $R^1$ and $R^3$, which may be identical or different, are each independently —OH, —SH, —$NH_2$, —COOH, —$R(CH_2)_mCH_3$, —$RCOCO(CH_2)_mCH_3$, —$RCO(CH_2)_mCHCH_3CH_3$, —$RCO(CH_2)_mNR^4CH_3$, —$RCOCHOH(CH_2)_mCH_3$, —$RCOCH_2(CH_2)_mCH_3$, —$RCOCH_2CHOH(CH_2)_mCH_3$, —$RCOCH_2(CH_2)_mCOOH$, —$RSO_2CH_2(CH_2)_mCH_3$, —$RPO_2(OH)CH_2(CH_2)_mCH_3$ or $RCOCH(NHCOCH_3)CH_2CH_2CONH_2$, in which R, $R^4$ and m are the same as defined above; and $R^2$ is H; (iii) $R^1$ is —OH, —SH, —$NH_2$, —COOH, —$R(CH_2)_mCH_3$, —$RCOCO(CH_2)_mCH_3$, —$RCO(CH_2)_mCHCH_3CH_3$, —$RCO(CH_2)_mNR^4CH_3$, —$RCOCHOH(CH_2)_mCH_3$, —$RCOCH_2(CH_2)_mCH_3$, —$RCOCH_2CHOH(CH_2)_mCH_3$, —$RCOCH_2(CH_2)_mCOOH$, —$RSO_2CH_2(CH_2)_mCH_3$, —$RPO_2(OH)CH_2(CH_2)_mCH_3$ or $RCOCH(NHCOCH_3)CH_2CH_2CONH_2$, in which R, $R^4$ and m are the same as defined above; $R^2$ is H; and $R^3$ is H, OH or Cl; (iv) $R^3$ is —OH, —SH, —$NH_2$, —COOH, —$R(CH_2)_mCH_3$, —$RCOCO(CH_2)_mCH_3$, —$RCO(CH_2)_mCHCH_3CH_3$, —$RCO(CH_2)_mNR^4CH_3$, —$RCOCHOH(CH_2)_mCH_3$, —$RCOCH_2(CH_2)_mCH_3$, —$RCOCH_2CHOH(CH_2)_mCH_3$, —$RCOCH_2(CH_2)_mCOOH$, —$RSO_2CH_2(CH_2)_mCH_3$, —$RPO_2(OH)CH_2(CH_2)_mCH_3$ or $RCOCH(NHCOCH_3)CH_2CH_2CONH_2$, in which R, $R^4$ and m are the same as defined above; $R^2$ is H; and $R^1$ is H, OH or Cl; or (v) $R^1$, $R^2$ and $R^3$, which may be identical or different, are each independently —OH, —SH, —$NH_2$, —COOH, —$R(CH_2)_mCH_3$, —$RCOCO(CH_2)_mCH_3$, —$RCO(CH_2)_mCHCH_3CH_3$, —$RCO(CH_2)_mNR^4CH_3$, —$RCOCHOH(CH_2)_mCH_3$, —$RCOCH_2(CH_2)_mCH_3$, —$RCOCH_2CHOH(CH_2)_mCH_3$, —$RCOCH_2(CH_2)_mCOOH$, —$RSO_2CH_2(CH_2)_mCH_3$, —$RPO_2(OH)CH_2(CH_2)_mCH_3$ or $RCOCH(NHCOCH_3)CH_2CH_2CONH_2$, in which R, $R^4$ and m are the same as defined above. In further aspect, the present invention provides the above compound of the formula V.

The retinoid derivative of the formula I according to the present invention can exist in a form of pharmaceutically acceptable acid or base salts. The term "pharmaceutically acceptable salts", as used herein, refers to salts with a reasonable benefit/risk ratio suitable for use in contact with tissues of human and lower animals without inducing excessive toxicity, irritation, allergy response, and the like within the scope of sound medical judgment. The pharmaceutically acceptable salts are well known in the art. For example, pharmaceutically acceptable salts are explained in detail in S. M. Berge et al., J. Pharmaceutical Sciences, 1977, 66:1.

The acid salts can be prepared in situ during final isolation and purification of the compound of the present invention or separately by reacting a free functionality with a suitable acid. Representative acid addition salts include, but are not limited to, acetates, adipates, alginates, citrates, aspartates, benzoates, benzenesulfonates, bisulfates, butyrates, camphorates, camphosulfonates, digluconates, glycerophosphates, hemisulfates, heptanoates, hexanoates, fumarates, hydrochlorides, hydrobromides, hydroiodides, 2-hydroxyethanesulfonates (isothionates), lactates, maleates, methanesulfonates, nicotinates, 2-naphthalenesulfonates, oxalates, palmitoates, pectinates, persulfates, 3-phenylpropionates, picrates, pivaleates, propionates, succinates, tartrates, thiocyanates, phosphates, glutamates, bicarbonates, p-toluenesulfonates and undecanoates. Also, basic nitrogen-containing groups can be made into quaternary salts, for example, lower alkyl halides such as methyl, ethyl, propyl and butyl chlorides, bromides and iodides; dialkyl sulfates such as dimethyl, diethyl, dibutyl and diamyl sulfates; long-chain halides such as decyl, lauryl, miristyl and stearyl chlorides, bromides and iodides; arylalkyl halides such as benzyl and penethyl bromides, and the like. Water- or oil-soluble and dispersible products are thereby obtained. Examples of acids which can be used to form pharmaceutically acceptable acid addition salts include inorganic acids such as hydrochloric acid, bromic acid, sulfuric acid and phosphoric acid, and organic acids such as oxalic acid, maleic acid, succinic acid and citric acid.

Base addition salts can be prepared by reacting the carboxylic acid moiety with suitable bases (for example, hydroxides, carbonates or bicarbonates of pharmaceutically acceptable metallic cations) or ammonia, or organic primary, secondary or tertiary amines in situ during final isolation and purification of the compound of the present invention. Examples of the pharmaceutically acceptable base salts include, but are not limited to, alkali metal or alkali earth metal salts such as lithium, sodium, potassium, calcium, magnesium and aluminium salts, and non-toxic quaternary ammonia and amine salts such as ammonium, tetramethylammonium, tetraethylammonium, methylammonium, dimethylammonium, trimethylammonium, triethylammonium, diethylammonium and ethylammonium salts. Other representative organic amines useful for formation of the base addition salts include ethyleneamine, ethanolamine, diethanolamine, piperidine, piperazine and the like.

The retinoid derivatives according to the present invention exert activity to kill cancer cells or to prevent proliferation of cancer cells by inducing apoptosis of cancer cells. The apoptosis, naturally programmed death of cells, takes place through activation of genes which triggers apoptosis as programmed by certain exogenous or endogenous factors, unlike necrosis which means pathological cell death. The activation of such genes leads to biosynthesis and digestion of programmed death gene proteins in their own cells, so that cells themselves are induced to commit suicide. The apoptosis is commonly measured by examining DNA fragmentation using a biochemical method. Recent reports have shown that substances inducing apoptosis of tumor cells also may regulate death of tumor cells and effectively prevent various cancers.

The retinoid derivatives according to the present invention exhibit activity to inhibit the activator protein-1 (AP-1). AP-1 is a transcription factor that interacts with TPA responsive element or DNA regulatory sequence known as AP-1 site (Angel, P. et al., Cell 49, 729–739 (1987)). A number of stimuli including tumor promoter TPA and reactive oxygen species regulate the binding of AP-1 to DNA of the promoter region of many intermediate genes controlling inflammation, proliferation and apoptosis (Ryseck, R. P. et al., Nature 334, 535–537 (1988); Angel, P. et al., Biochim. Biophys. Acta 1072, 129–157 (1991); and Muller, J. M. et al., Methods (Orlando) 11, 301–312 (1997)). AP-1 and gene expression controlled by AP-1 have been known to play a critical role in neoplasm transformation, tumor development and metastasis (Bernstein, L. R. et al., Science 244, 566–569 (1989); Barthelman, M. et al., Cancer Res. 58, 711–716 (1998); McDonnell, S. et al., Cancer Metastasis Rev. 9, 305–319 (1990); and Crawford, H. C. et al., Enzyme Protein 49, 20–37 (1996)).

Therefore, the retinoid derivatives according to the present invention are useful in the prevention or treatment of a variety of cancers including, but not limited to: carcinoma such as bladder cancer, breast cancer, intestines cancer, kidney cancer, liver cancer, lung cancer (including small cell lung cancer), brain cancer, esophageal cancer, gall cancer, ovary cancer, pancreas cancer, stomach cancer, cervix cancer, thyroid gland cancer, prostate gland cancer and skin cancer (including squamous cell carcinoma); hematopoietic tumors in the lymphatic system including leukemia, acute lymphocytic leukemia, acute lymphoblastic leukemia, B-cell lymphoma, T-cell lymphoma, Hodgkin lymphoma, non-Hodgkin lymphoma, hairy-cell lymphoma and Burkitts lymphoma; hematopoietic tumors in the marrow system including acute and chronic myeloid leukemia, myelodysplastic syndrome and promyelocytic leukemia; tumors originating from mesenchyme, including fibrosarcoma and rhabdomyosarcoma; tumors in central and peripheral nervous systems, including astrocytoma, neuroblastoma, neuroglioma and schwanoma; and other tumors including melanoma, seminoma, teratoma, osteosarcoma, xeroderma pigmentosum, keratoacanthoma, thyroid follicular carcinoma and Kaposi sarcoma.

The retinamide derivatives according to the present invention can be administered alone or, alternatively, in combination with known cancer treatments such as radiation therapy or chemotherapy regimen (cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), metallomatrixprotease inhibitors, telomerase inhibitors, tyrosine kinase inhibitors, anti-growth factor receptor agents, anti-HER agents, anti-EGFR agents, anti-angiogenesis agents, farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like). As examples, the retinamide derivatives according to the present invention can be administered in combination with at least one chemotherapeutic agent, such as, taxane, taxane derivatives, encapsulated taxanes, CPT-11, camptothecin derivatives, anthracycline glycosides, e.g., doxorubicin, idarubicin, epirubicin, etoposide, navelbine, vinblastine, carboplatin, cisplatin, estramustine, celecoxib, Sugen SU-5416, Sugen SU-6668, Herceptin, and the like, optionally within liposomal formulations thereof.

Where the combination is formulated as a fixed dose, the retinamide derivative compound is used within the dose range described below while other pharmaceutical active ingredients being within the approved dose range. However, where the combination is not appropriate, the retinamide derivative compound of the present invention can be used sequentially along with any known anti-cancer agents.

The retinoid derivative compound according to the present invention can be used in itself or as a pharmaceutical composition in combination with at least one pharmaceutically acceptable carrier. The term "therapeutically effective amount" of the compound of the present invention, as used herein, refers to an amount sufficient for treating a disease in a reasonable benefit/risk ratio so as to be applicable to medical treatment. However, it will be understood that the total daily dose of the compound or composition of the present invention will be determined by physicians within the scope of sound medical judgment. The specific therapeutically effective dose level for any particular patient will depend upon a variety of factors including diseases and severity thereof; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and factors well known in the medical arts. For example, the skilled in the art appreciates that the dose of the compound is determined at a level less than that needed to achieve a desired therapeutic effect and then, gradually increased until the desired effect is achieved.

The retinamide derivatives according to the present invention can be administered by the usual routes, for example, orally, in the form of tablets, capsules, sugar-coated pills or film-coated tablets, solutions or suspensions; rectally, in the form of suppositories; and parenterally, e.g. intramuscularly, or by intravenous and/or intrathecal and/or intraspinal injection or infusion.

The daily effective dose of the retinoid derivatives according to the present invention is preferably 0.75 to 1.0 mg per kg body weight of a patient per day for the first 8 to 16 weeks and, additionally 0.5 to 1.7 mg after 8 weeks, as needed. When administered under these conditions, the retinoid derivatives according to the present invention show a maximum concentration in blood of 0.3 to 0.7 mg/ml. The dose may be suitably varied depending on the age, body weight, general health, sex, severity of disease, diet of the patient, the time of administration, rate of excretion and route of administration.

The retinoid derivatives according to the present invention can be provided as a pharmaceutical composition for a specific dose form combined with pharmaceutically acceptable carriers, diluents or vehicles. The pharmaceutical compositions of the invention are usually formulated following conventional methods and are administered in a pharmaceutically suitable form. For example, the solid oral forms may contain, together with the active compound, diluents, for example, lactose, dextrose, sucrose, cellulose, corn starch or potato starch; lubricants, for example, silica, talc, stearic acid, magnesium or calcium stearate, and/or polyethylene glycols; binding agents, for example, starches, arabic gum, gelatine, methylcellulose, carboxymethylcellulose or polyvinyl pyrrolidone; disaggregating agents, for example, a starch, alginic acid, alginates or sodium starch glycolate; effervescing mixtures; dyestuffs; sweeteners; wetting agents such as lecithin, polysorbates and laurylsulphates; and, in general, pharmacologically inactive substances used in pharmaceutical formulations. These pharmaceutical preparations may be manufactured in a known manner, for example, by means of mixing, granulating, tabletting, sugar-coating, or film-coating processes.

Another mode for oral administration of the retinoid derivatives according to the present invention is examplified as liquid dispersions, typically including syrups, emulsions or suspensions. The suspensions and the emulsions may contain as a carrier, for example, a natural gum, agar, sodium alginate, pectin, methylcellulose, carboxymethylcellulose, or polyvinyl alcohol.

The suspension or solutions for intramuscular injections of the retinoid derivatives according to the present invention may contain, together with the active compound, a pharmaceutically acceptable carrier, e.g. sterile water, olive oil, ethyl oleate, glycols, for example, propylene glycol, and, if desired, a suitable amount of lidocaine hydrochloride. The solutions for intravenous injections or infusions of the retinoid derivatives according to the present invention may contain as a carrier, for example, sterile water, or preferably they may be in the form of sterile, aqueous, isotonic saline solutions or they may contain as a carrier propylene glycol.

The suppositories useful for administration of the retinoid derivatives of the present invention may contain, together with the active compound, a pharmaceutically acceptable carrier, for example, cocoa butter, polyethylene glycol, a polyoxyethylene sorbitan fatty acid ester surfactant or lecithin.

Now, the present invention will be concretely illustrated by the following examples. However, the examples are given only for embodiments of the present invention but not for limitation of the scope of the invention.

EXAMPLE

I. Preparation of Resorcinol Derivative

Example 1

(2E,4E,6E,8E)-[3,7-dimethyl-9-(2,6,6-trimethylcyclohex-1-enyl)-nona-2,4,6,8-tetraenoyl]-(2,4-dihydroxy)phenylamide (KCBG08)

A solution of EDCI (0.076 g, 0.39 mmol) and retinoic acid (0.10 g, 0.33 mmol) in anhydrous DMF (5 mL) was stirred at 0° C. for 0.5 h. To this solution was added a solution of 4-amino resorcinol.HCl (0.063 g, 0.39 mmol) and DMAP (cat.) in anhydrous DMF (5 mL). The resulting mixture was stirred at room temperature for 4 h. The reaction mixture was diluted with EtOAc (30 mL), washed with $H_2O$ (2×30 mL) and concentrated. The crude product was purified by flash column chromatography on silica gel (EtOAc:hexane=1:4) to give (2E,4E,6E,8E)-[3,7-dimethyl-9-(2,6,6-trimethylcyclohex-1-enyl)-nona-2,4,6,8-tetraenoyl]-(2,4-dihydroxy) phenylamide (KCBG08, 0.078 g, 58%) as a yellow solid.

Example 2

(2E,4E,6E,8E)-[3,7-dimethyl-9-(2,6,6-trimethylcyclohex-1-enyl)-nona-2,4,6,8-tetraenoyl]-(2,4-dihydroxy)phenylamide (KCBG08)

A mixture of anhydrous DMF (2 mL) and $SOCl_2$ (0.072 mL, 0.99 mmol) was stirred under argon for 1 h. To the mixture was added a solution of retinoic acid (0.10 g, 0.33 mmol) in anhydrous DMF (2 mL). After stirring at 0° C. for 45 min, the clear deep red retinoyl chloride solution was added dropwise to a cooled solution distilled triethylamine (0.14 mL, 0.99 mmol) and 4-amino resorcinol.HCl (0.10 g, 0.66 mmol) in dry, degassed DMF (2 mL). The reaction was quenched with $NH_4Cl$ (aq.), extracted with EtOAc (30 mL). The extracts were washed with $H_2O$ (2×30 mL) and concentrated. The residue was purified by flash column chromatography on silica gel (EtOAc:hexane=1:4) to give KCBG08 (0.11 mg, 86%) as a yellow solid.

$^1$H-NMR (200 MHz, $CDCl_3$): δ 7.78 (br s, 1H, NH), 6.97 (dd, 1H, J=15.00), 6.76 (d, 1H, J=8.60, Ar—H), 6.09~6.43 (m, 6H), 5.83 (s, 1H), 2.37 (s, 3H), 1.99~2.03 (m, 2H), 1.98 (s, 3H), 1.71 (s 3H), 1.58~1.62 (m, 2H), 1.45~1.47 (m, 2H), 1.02 (s, 6H).

$^{13}$C NMR (100 MHz, $CDCl_3$): δ 166.89, 154.94, 151.98, 149.80, 139.67, 137.64, 137.25, 135.14, 131.06, 130.01, 129.57, 128.65, 123.60, 119.53, 119.01, 107.88, 105.92, 39.57, 34.23, 33.10, 28.95, 21.76, 19.19, 14.15, 13.82, 12.89.

Example 3

(2,4-Dihydroxyphenyl)-carbamic acid benzyl ester (KCBG02)

To a cooled solution (0° C.) of 4-amino resorcinol.HCl (1.0 g, 6.18 mmol) in $H_2O$ (10 mL) was added dropwise aq. NaOH (0.49 g, 12.3 mmol) in $H_2O$ (15 mL). To this mixture were added slowly Cbz-Cl (Carbobenzoxy chloride, 1.06 mL, 7.43 mmol) and NaOH (0.25 g) in $H_2O$ (5 mL). After stirring for 1 h at room temperature, the mixture was extracted with EtOAc (2×50 mL). The organic layer was dried over $MgSO_4$ (10 g), filtrated and concentrated. The residue was purified by flash column chromatography on silica gel (EtOAc:hexane=1:5) to give (2,4-dihydroxyphenyl)-carbamic acid benzyl ester (KCBG02. 1.28 g, 80%).

$^1$H-NMR (200 MHz, $CDCl_3$): δ 8.96 (br s, 1H, OH), 8.46 (br s, 1H), 7.47 (d, 1H, NH), 7.33~7.41 (m, 5H), 6.45 (d, 1H, J=2.50), 6.33 (dd, 1H, J=8.64, 2.50), 5.17 (s, 2H).

Example 4

2-Benzyloxycarbonylamino-5-hydroxyphenylbutanoate (KCBG03) and 2-Benzyloxycarbonylamino-5-butyryloxyphenylbutanoate (KCBG04)

(2,4-Dihydroxyphenyl)-carbamic acid benzyl ester KCBG02 (0.050 g, 0.19 mmol) was dissolved in anhydrous $CH_2Cl_2$ (10 mL), and NMM (N-methyl morpholine, 0.029 ml, 0.29 mmol) was added. To the resulting mixture was added dropwise butyryl chloride (0.029 ml, 0.28 mmol) in anhydrous $CH_2Cl_2$ (2 mL) at 0° C., and stirred for 0.5 h and the reaction was washed with $H_2O$ (2×10 mL). The organic layer was dried over anhydrous $MgSO_4$ and concentrated under reduced pressure. The crude product was purified by flash column chromatography over silica gel (EtOAc:hexane=1:10) to give 2-Benzyloxycarbonylamino-5-hydroxyphenylbutanoate (19 mg, 30%) and 2-Benzyloxycarbonylamino-5-butyryloxyphenylbutanoate (46 mg, 60%).

2-Benzyloxycarbonylamino-5-hydroxyphenylbutanoate $^1$H-NMR (200 MHz, $CDCl_3$): δ 7.55 (d, 1H, J=7.24, NH), 7.37 (m, 5H)1.00 (t, J=7.42, 3H), 6.65 (d, 1H, J=2.74), 6.56 (s, 1H), 6.38 (s, 1H), 5.17 (s, 2H), 2.50 (t, 2H, J=7.35), 1.68~1.76 (m, 2H).

$^{13}$H-NMR (100 MHz $CDCl_3$): δ 171.65, 155.01, 154.89, 135.87, 128.59, 128.38, 127.95, 121.73, 113.62, 109.77, 67.33, 36.00, 18.39, 13.54.

2-Benzyloxycarbonylamino-5-butyryloxyphenylbutanoate $^1$H-NMR (200 MHz, $CDCl_3$): δ 8.03 (d, 1H, J=7.24, NH), 7.39 (m, 5H), 6.97 (s, 1H), 6.93 (d, 1H, J=2.62), 6.68 (s, 1H), 5.18 (s, 2H), 2.52 (m, 4H), 1.66~1.85 (m, 4H), 1.01 (t, J=7.42, 6H).

$^{13}$H-NMR (100 MHz $CDCl_3$): δ 171.73, 170.79, 153.07, 145.93, 140.12, 135.73, 128.60, 128.48, 128.30, 128.25, 127.22, 122.22, 119.09, 115.77, 67.13, 35.94, 35.82, 29.55, 18.19, 13.48, 13.41.

Example 5

2-Amino-5-hydroxyphenylbutanoate (KCBG05)

To a solution of 2-benzyloxycarbonylamino-5-hydroxyphenylbutanoate (KCBG03) (0.07 mg, 0.21 mmol) in MeOH (5 mL) was added Pd/C (10%, 5 mg) at room temperature. After stirring for 20 min under $H_2$, the reaction mixture was filtered and evaporated in vacuo to give 2-amino-5-hydroxyphenylbutanoate (KCBG05, 39 mg, 95%) as a white solid.

$^1$H-NMR (200 MHz, $CDCl_3$+$CD_3OD$): δ 7.18 (d, 1H, J=8.60), 6.41 (d, 1H, J=2.60), 6.32 (dd, 1H, J=8.60, 2.60), 2.36 (t, 2H, J=7.42), 1.66~1.80 (m, 2H), 1.00 (t, J=7.42, 3H).

Example 6

2-Amino-5-butyryloxyphenylbutanoate (KCBG06)

To a solution of 2-benzyloxycarbonylamino-5-butyryloxyphenylbutanoate (KCBG04) KCBG04 (0.05 g, 0.12 mmol) in MeOH (5 mL) was added Pd/C (10%, 4 mg) at room temperature. After stirring for 20 min under $H_2$, the reaction mixture was filtered and evaporated in vacuo to give 2-amino-5-butyryloxyphenyl butanoate (KCBG06, 0.031 g, 96%) as a white solid.

$^1$H-NMR (200 MHz, $CDCl_3$): δ 6.90 (d, 1H, J=8.60), 6.65 (d, 1H, J=2.60), 6.50 (dd, 1H, J=8.60, 2.60), 2.54 (t, 2H, J=7.42), 2.36 (t, 2H, J=7.42), 1.64~1.86 (m, 4H), 0.95~1.07 (m, 6H).

Example 7

2.2-[(2E,4E,6E,8E)-3,7-Dimethyl-9-(2,6,6-trimethyl-cyclohex-1-enyl)-nona-2,4,6,8-tetraenoylamino]-5-hydroxyphenylbutanoate (KCBG10)

To a solution of EDCI (0.023 g, 0.12 mmol) in anhydrous DMF (5 mL) was added a solution of retinoic acid (0.031 g, 0.10 mmol) in anhydrous DMF (5 mL). The mixture was stirred at room temperature for 0.5 h. A solution of 2-amino-5-hydroxy-phenyl butanoate (KCBG05, 0.020 g, 0.12 mmol) and DMAP (cat.) in anhydrous DMF (2 mL) was added to the mixture, and again stirred for 4 h. The reaction was quenched with $NH_4Cl$ (aq.), extracted with EtOAc (2×30 mL). The extracts were washed with $H_2O$ (2×30 mL), dried over anhydrous $Na_2SO_4$, and evaporated. The residue was purified by flash column chromatography over silica gel (EtOAc:hexane=1:6) to give 2-[(2E,4E,6E,8E)-3,7-dimethyl-9-(2,6,6-trimethylcyclohex-1-enyl)-nona-2,4,6,8-tetraenoylamino]-5-hydroxyphenyl butanoate (KCBG10, 0.038 g, 78%) as a yellow solid.

$^1$H-NMR (200 MHz, $CDCl_3$): δ 9.63 (s, 1H, OH), 7.48 (s, 1H, NH), 7.05 (dd, 1H, J=14.90), 6.86 (d, 1H, J=8.60), 6.73 (d, 1H, J=2.50), 6.57 (dd, 1H, J=8.60, 2.50), 6.10~6.35 (m, 4H), 5.86 (s, 1H), 2.54 (t, 2H, J=7.30), 2.41 (s, 3H), 2.01 (br s, 5H), 1.71~1.89 (m, 2H), 1.72 (s, 3H), 1.58~1.62 (m, 2H), 1.45~1.47 (m, 2H), 0.96~1.09 (m, 3H), 1.02 (s, 6H).

$^{13}$C NMR (100 MHz, $CDCl_3$): δ 172.41, 166.90, 152.86, 150.13, 149.19, 140.07, 137.67, 137.17, 134.85, 131.47, 130.11, 129.39, 128.96, 123.96, 122.46, 119.03, 113.29, 112.94, 39.57, 36.18, 34.24, 33.10, 29.68, 28.94, 21.74, 19.18, 18.43 13.83, 13.60, 12.94.

Example 8

2.2-[(2E,4E,6E,8E)-3,7-Dimethyl-9-(2,6,6-trimethyl-cyclohex-1-enyl)-nona-2,4,6,8-tetraenoylamino]-5-hydroxyphenylbutanoate (KCBG10) and

5-Butyryloxy-2-[3,7-dimethyl-9-(2,6,6-trimethylcyclohex-1-enyl)-nona-2,4,6,8-tetraenoylamino]-phenylbutanoate (KCBG09)

To the solution of (2E,4E,6E,8E)-[3,7-dimethyl-9-(2,6,6-trimethylcyclohex-1-enyl)-nona-2,4,6,8-tetraenoyl]-(2,4-dihydroxy)phenylamide (KCBG08) (0.051 g, 0.12 mmol) in anhydrous $CH_2Cl_2$ (15 mL) was added NMM (0.019 g, 0.18 mmol). To the resulting mixture was added dropwise butyryl chloride (0.019 ml, 0.18 mmol) in anhydrous $CH_2Cl_2$ (2 mL) at 0° C., and stirred for 0.5 h and the reaction was washed with $H_2O$ (2×20 mL). The organic layer was dried over anhydrous $MgSO_4$ and concentrated under reduced pressure. The crude product was purified by column chromatography over silica gel (EtOAc:hexane=1:5) to give 2-[(2E,4E,6E,8E)-3,7-dimethyl-9-(2,6,6-trimethyl-cyclohex1-enyl)-nona-2,4,6,8-tetraenoylamino]-5-hydroxy-phenyl butanoate (KCBG10, 24 mg, 40%) and 5-butyryloxy-2-[3,7-dimethyl-9-(2,6,6-trimethyl-cyclohex-1-enyl)-nona-2,4,6,8-tetraenoylamino]-phenyl butanoate (KCBG09, 30 mg, 45%).

Example 9

2.2-[(2E,4E,6E,8E)-3,7-dimethyl-9-(2,6,6-trimethyl-cyclohex-1-enyl)-nona-2,4,6,8-tetraenoylamino]-5-hydroxyphenylbutanoate (KCBG10) and

5-Butyryloxy-2-[3,7-dimethyl-9-(2,6,6-trimethylcyclohex-1-enyl)-nona-2,4,6,8-tetraenoylamino]-phenylbutanoate (KCBG09)

To a solution of EDCI (0.07 g, 0.36 mmol) in anhydrous $CH_2Cl_2$ (15 mL) was added butyric acid (0.033 mL, 0.36 mmol). The solution was stirred at room temperature for 0.5 h. To this mixture were added a solution of (2E,4E,6E,8E)-[3,7-dimethyl-9-(2,6,6-trimethylcyclohex-1-enyl)-nona-2,4,6,8-tetraenoyl]-(2,4-dihydroxy)phenylamide (KCBG08) (0.1 g, 0.24 mmol) and DMAP (cat.) in anhydrous $CH_2Cl_2$ (2 mL), and stirred for 2 h. The reaction was washed with $H_2O$ (2×20 mL), dried over anhydrous $Na_2SO_4$, and evaporated. The residue was purified by flash column chromatography over silica gel (EtOAc:hexane=1:5) to give 2.2-[(2E, 4E,6E,8E)-3,7-dimethyl-9-(2,6,6-trimethylcyclohex-1-enyl)-nona-2,4,6,8-tetraenoylamino]-5-hydroxyphenylbutanoate (KCBG10, 42 mg, 35%) and 5-Butyryloxy-2-[3,7-dimethyl-9-(2,6,6-trimethylcyclohex-1-enyl)-nona-2,4,6,8-tetraenoylamino]-phenylbutanoate (KCBG09, 53 mg, 40%) as a yellow solid.

5-Butyryloxy-2-[3,7-dimethyl-9-(2,6,6-trimethylcyclohex-1-enyl)-nona-2,4,6,8-tetraenoylamino]-phenylbutanoate (KCBG09)

$^1$H-NMR (200 MHz, $CDCl_3$): δ 8.26 (br s, 1H), 7.19 (br s, 1H), 6.93~7.01 (m, 4H), 6.10~6.31 (m, 4H), 5.75 (s, 1H), 2.55 (q, 4H, J=7.35), 2.41 (s, 3H), 2.01 (br s, 5H), 1.71~1.89 (m, 4H), 1.72 (s 3H), 1.58~1.62 (m, 2H), 1.45~1.47 (m, 2H), 0.96~1.09 (m, 6H), 1.02 (s, 6H).

$^{13}$C NMR (100 MHz, $CDCl_3$): δ 171.88, 170.91, 139.47, 137.62, 137.17, 136.76, 135.02, 130.72, 130.55, 130.36, 129.90, 129.37, 128.60, 127.61, 126.13, 119.09, 115.75, 39.48, 36.03, 34.17, 33.01, 29.94, 28.86, 25.88, 25.81, 21.67, 21.00, 19.12, 18.33, 18.26, 13.55, 12.84.

Example 10

2.2-[(2E,4E,6E,8E)-3,7-dimethyl-9-(2,6,6-trimethyl-cyclohex-1-enyl)-nona-2,4,6,8-tetraenoylamino]-5-hydroxyphenylbutanoate (KCBG10)

(2E,4E,6E,8E)-[3,7-dimethyl-9-(2,6,6-trimethylcyclohex-1-enyl)-nona-2,4,6,8-tetraenoyl]-(2,4-dihydroxy)phenylamide (KCBG08) (0.10 g, 0.24 mmol) was dissolved in anhydrous $CH_2Cl_2$ (15 mL), and NMM (0.049 g, 0.49 mmol) was added. To the resulting mixture was added dropwise butyryl chloride (0.050 mL, 0.49 mmol) at 0° C., and the resulting solution was stirred for 0.5 h. Finely ground $K_2CO_3$ (0.30 g) and MeOH (3 mL) was added to the reaction mixture. After stirring for 1 h, the completion of the reaction was confirmed by TLC. The mixture was washed with $CH_2Cl_2$ (30 mL) and $H_2O$ (20 mL). The organic layer was dried over anhydrous $MgSO_4$ and evaporated in vacuo. The residue was purified by flash column chromatography over silica gel (EtOAc:hexane=1:4) to give 2-[(2E,4E,6E,8E]-3,7-dimethyl-9-(2,6,6-trimethylcyclohex-1-enyl)-nona-2,4,6,8-tetraenoylamino)-5-hydroxyphenyl butanoate (KCBG10, 97 mg, 83%) as a yellow solid.

Example 11

2-[(2E,4E,6E,8E)-3,7-dimethyl-9-(2,6,6-trimethylcyclohex-1-enyl)-nona-2,4,6,8-tetraenoylamino]-5-hydroxyphenyl-2-oxopropionate (KCBG22)

To a solution of EDCI (0.046 g, 0.24 mmol) in anhydrous $CH_2Cl_2$ (5 mL) was added a solution of pyruvic acid (0.17 mL, 0.24 mmol) in anhydrous $CH_2Cl_2$ (5 mL). The solution was stirred at room temperature for 0.5 h. To this mixture were added a solution of 2.2-[(2E,4E,6E,8E)-3,7-dimethyl-9-(2,6,6-trimethylcyclohex-1-enyl)-nona-2,4,6,8-tetraenoylamino)-5-hydroxyphenyl butanoate (KCBG10, 0.05 g, 0.12 mmol) and DMAP (cat.) in anhydrous $CH_2Cl_2$ (2 mL), and stirred at room temperature for 1 h. The resulting solution was heated to 30° C. and again stirred for 3 h. The reaction was diluted with EtOAc(30 mL), washed with $H_2O$ (2×30 mL), dried over anhydrous $Na_2SO_4$, and evaporated. The crude compound was purified by flash column chromatography over silica gel (EtOAc:hexane=1:4) to give 2-[(2E,4E,6E,8E)-3,7-dimethyl-9-(2,6,6-trimethylcyclohex-1-enyl)-nona-2,4,6,8-tetraenoylamino]-5-hydroxyphenyl-2-oxopropionate (KCBG22, 0.017 g, 30%) as a pale yellow solid.

$^1$H-NMR (200 MHz, $CDCl_3$): δ 8.83 (s, 1H, OH), 8.10 (d, J=8.70, NH) 7.15 (dd, 1H, J=14.90), 6.67~6.75 (m, 2H), 6.03~6.43 (m, 5H), 5.65 (s, 1H), 2.54 (s, 3H), 2.42 (s, 3H), 2.01 (br s, 5H), 1.72 (s, 3H), 1.58~1.62 (m, 2H), 1.45~1.47 (m, 2H), 1.04 (s, 6H).

$^{13}$C NMR (100 MHz, $CDCl_3$): δ 190.92, 167.03, 158.75, 153.51, 150.28, 148.50, 140.38, 137.66, 137.12, 134.65, 131.83, 130.21, 129.31, 129.16, 124.70, 122.55, 118.61, 112.65, 112.61, 39.57, 34.25, 33.11, 28.94, 26.82, 21.75, 19.18, 13.89, 12.96.

Example 12

2-[(2E,4E,6E,8E)-3,7-dimethyl-9-(2,6,6-trimethylcyclohex-1-enyl)-nona-2,4,6,8-tetraenoylamino]-5-hydroxyphenyl 2-oxobutanoate (KCBG38)

To a solution of EDCI (0.046 g, 0.24 mmol) in anhydrous $CH_2Cl_2$ (5 mL) was added a solution of 2-ketobutyric acid (0.025 g, 0.24 mmol) in anhydrous $CH_2Cl_2$ (5 mL). The solution was stirred at room temperature for 0.5 h. To this mixture were added a solution of 2.2-[(2E,4E,6E,8E)-3,7-dimethyl-9-(2,6,6-trimethylcyclohex-1-enyl)-nona-2,4,6,8-tetraenoylamino]-5-hydroxyphenylbutanoate (KCBG10) (0.05 g, 0.12 mmol) and DMAP (cat.) in anhydrous $CH_2Cl_2$ (2 mL). The resulting solution was stirred at room temperature for 1 h. This solution was heated to 30° C. and again stirred for 3 h. The reaction was diluted with EtOAc (30 mL), washed with $H_2O$ (2×30 mL), dried over $Na_2SO_4$, and evaporated. The crude compound was purified by flash column chromatography over silica gel (EtOAc:hexane=1:4) to give 2-[(2E,4E,6E,E)-3,7-dimethyl-9-(2,6,6-trimethylcyclohex-1-enyl)-nona-2,4,6,8-tetraenoylamino]-5-hydroxyphenyl 2-oxobutanoate (KCBG38, 0.021 g, 35%) as a pale yellow solid.

$^1$H-NMR (200 MHz, $CDCl_3$): δ 9.74 (s, 1H, OH), 7.41 (br s, 1H) 7.15 (dd, 1H, J=14.90), 6.67~6.75 (m, 3H), 6.19~6.33 (m, 4H), 5.87 (s, 1H), 3.01 (q, 2H, J=7.42), 2.44 (s, 3H), 2.01 (br s, 5H), 1.72 (s, 3H), 1.58~1.62 (m, 2H), 1.45~1.47 (m, 2H), 1.17~1.29 (m, 3H), 1.04 (s, 6H).

$^{13}$C NMR (100 MHz, $CDCl_3$): δ 194.19, 166.70, 159.18, 139.98, 138.70, 137.19, 134.98, 131.31, 130.12, 129.42, 128.93, 125.11, 122.15, 119.56, 112.42, 111.75, 39.59, 34.27, 33.12, 33.07, 28.96, 21.77, 19.21, 13.84, 12.96.

Example 13

2-[(2E,4E,6E,8E)-3,7-Dimethyl-9-(2,6,6-trimethylcyclohex-1-enyl)-nona-2,4,6,8-tetraenoylamino]-5-hydroxyphenyl(dimethylamino)acetate (KCBG23)

To a solution of EDCI (0.046 g, 0.24 mmol) in anhydrous $CH_2Cl_2$ (5 mL) was added a solution of N,N-dimethyl glysine (sarcosine, 0.025 g, 0.24 mmol) in anhydrous $CH_2Cl_2$ (5 mL). The solution was stirred at room temperature for 0.5 h. To this mixture were added a solution of 2.2-[(2E,4E,6E,8E)-3,7-dimethyl-9-(2,6,6-trimethylcyclohex-1-enyl)-nona-2,4,6,8-tetraenoylamino]-5-hydroxyphenylbutanoate (KCBG10) (0.051 g, 0.12 mmol) and DMAP (cat.) in anhydrous DMF (2 mL). The resulting solution was stirred at room temperature for 1 h. This solution was heated to 30° C. and again stirred for 3 h. The reaction was diluted with EtOAc (30 mL), washed with $H_2O$ (2×30 mL), dried over $Na_2SO_4$, and evaporated. The crude compound was purified by flash column chromatography over silica gel (EtOAc:hexane=2:1) to give 2-[(2E,4E,6E,8E)-3,7-dimethyl-9-(2,6,6-trimethylcyclohex-1-enyl)-nona-2,4,6,8-tetraenoylamino]-5-hydroxyphenyl(dimethylamino)acetate (KCBG23, 0.045 g, 75%) as a pale yellow solid.

$^1$H-NMR (200 MHz, $CDCl_3$): δ 9.37 (s, 1H, OH), 8.01 (d, NH, J=9.48), 7.12 (dd, 1H, J=14.90), 6.63~6.83 (m, 2H), 6.11~6.40 (m, 5H), 6.00 (s, 1H), 3.05 (s, 2H), 2.40 (s, 3H), 2.30 (s, 6H), 2.03 (br s, 5H), 1.72 (s, 3H), 1.58~1.62 (m, 2H), 1.45~1.47 (m, 2H), 1.04 (s, 6H).

$^{13}$C NMR (100 MHz, $CDCl_3$): δ 169.34, 164.66, 159.67, 154.09, 142.40, 140.92, 137.59, 137.05, 134.32, 132.58, 130.32, 129.43, 129.22, 123.99, 121.83, 115.96, 113.44,

Example 14

2-[(2E,4E,6E,8E)-3,7-dimethyl-9-(2,6,6-trimethylcyclohex-1-enyl)-nona-2,4,6,8-tetraenoylamino]-5-hydroxyphenyl-3-hydroxybutanoate (KCBG39)

To a solution of EDCI (0.046 g, 0.24 mmol) in anhydrous $CH_2Cl_2$ (5 mL) was added a solution of 3-hydroxy butyric acid (0.023 mL, 0.24 mmol) in anhydrous $CH_2Cl_2$ (2 mL). The solution was stirred at room temperature for 0.5 h. To this mixture was added a solution of 2.2-[(2E,4E,6E,8E)-3,7-dimethyl-9-(2,6,6-trimethylcyclohex-1-enyl)-nona-2,4,6,8-tetraenoylamino]-5-hydroxyphenylbutanoate (KCBG10, 0.051 g, 0.12 mmol) and DMAP (cat.) in anhydrous $CH_2Cl_2$ (2 mL). The resulting solution was stirred at room temperature for 1 h, heated to 30° C. and again stirred for 3 h. The reaction was diluted with EtOAc (30 mL), and then the organic layer was washed with $H_2O$ (2×30 mL), dried over $Na_2SO_4$ and evaporated. The crude compound was purified by flash column chromatography over silica gel (EtOAc:hexane=1:1) to give 2-[(2E,4E,6E,8E)-3,7-dimethyl-9-(2,6,6-trimethylcyclohex-1-enyl)-nona-2,4,6,8-tetraenoylamino]-5-hydroxyphenyl-3-hydroxybutanoate (KCBG39, 0.045 g, 73%) as a pale yellow solid.

$^1$H-NMR (200 MHz, $CDCl_3$): δ 8.49 (br s, 1H), 8.17 (br s, 1H), 6.91~7.04 (m, 3H), 6.08~6.32 (m, 4H), 5.82 (s, 1H), 4.27~4.32 (m, 1H), 2.62~2.76 (m, 2H), 2.44 (s, 3H), 2.01 (br s, 5H), 1.72 (s, 3H), 1.58~1.62 (m, 2H), 1.45~1.47 (m, 2H), 1.20~1.31 (m 3H), 1.04 (s, 6H).

$^{13}$C NMR (100 MHz, $CDCl_3$): δ 171.06, 169.23, 150.94, 139.28, 137.66, 137.19, 135.47, 130.39, 129.93, 129.49, 129.00, 128.50, 121.50, 119.31, 116.03, 64.23, 43.78, 42.96, 39.54, 34.21, 33.06, 28.91, 23.28, 22.54, 21.71, 19.16, 13.69, 12.85.

Example 15

2-[(2E,4E,6E,8E)-3,7-dimethyl-9-(2,6,6-trimethylcyclohex-1-enyl)-nona-2,4,6,8-tetraenoylamino]-5-propionyloxyphenylpropionate (KCBG14) and 2-[(2E,4E,6E,8E)-3,7-dimethyl-9-(2,6,6-trimethylcyclohex-1-enyl)-nona-2,4,6,8-tetraenoylamino]-5-hydroxyphenylpropionate (KCBG15)

(2E,4E,6E,8E)-[3,7-dimethyl-9-(2,6,6-trimethylcyclohex-1-enyl)-nona-2,4,6,8-tetraenoyl]-(2,4-dihydroxy)phenylamide (KCBG08) (0.051 g, 0.12 mmol) was dissolved in anhydrous $CH_2Cl_2$ (15 mL), and NMM (0.02 mL, 0.18 mmol) was added. To the resulting mixture was added dropwise propionyl chloride (0.016 mL, 0.18 mmol) at 0° C., and stirred for 0.5 h. The reaction mixture was washed with $H_2O$ (2×20 mL), extracted with $CH_2Cl_2$. The organic layer was dried over $MgSO_4$ and evaporated in vacuo. The residue was purified by column chromatography over silica gel (EtOAc:hexane=1:5) to give 2-[(2E,4E,6E,8E)-3,7-dimethyl-9-(2,6,6-trimethylcyclohex-1-enyl)-nona-2,4,6,8-tetraenoylamino]-5-propionyloxyphenylpropionate (KCBG14, 0.023 g, 35%) and 2-[(2E,4E,6E,8E)-[3,7-dimethyl-9-(2,6,6-trimethylcyclohex-1-enyl)-nona-2,4,6,8-tetraenoylamino]-5-hydroxyphenylpropionate (KCBG15, 0.028 g, 43%) as yellow solids.

2-[(2E,4E,6E,8E)-[3,7-dimethyl-9-(2,6,6-trimethylcyclohex-1-enyl)-nona-2,4,6,8-tetraenoylamino]-5-propionyloxyphenylpropionate (KCBG 14)

$^1$H-NMR (200 MHz, $CDCl_3$): δ 8.24 (bsr, 1H), 7.16 (br s, 1H), 6.94~7.02 (m, 4H), 6.09~6.32 (m, 4H), 5.75 (s, 1H), 2.55 (q, 4H, J=7.38), 2.41 (s, 3H), 2.01 (br s, 5H), 1.72 (s 3H), 1.58~1.62 (m, 2H), 1.45~1.47 (m, 2H), 1.247 (t, 3H, J=7.38), 1.245 (t, 3H, J=7.41), 1.02 (s, 6H).

$^{13}$C NMR (100 MHz, $CDCl_3$): δ 171.98, 170.81, 139.46, 137.60, 137.15, 136.66, 134.92, 130.62, 130.38, 130.38, 129.91, 129.29, 128.78, 127.51, 126.13, 119.09, 115.75, 39.57, 34.23, 33.01, 29.94, 28.86, 25.81, 21.67, 21.00, 19.12, 18.33, 18.26, 13.82, 12.89.

2-[(2E,4E,6E,8E)-[3,7-dimethyl-9-(2,6,6-trimethylcyclohex-1-enyl)-nona-2,4,6,8-tetraenoylamino]-5-hydroxyphenylpropionate $^1$H-NMR (200 MHz, $CDCl_3$): δ 9.58 (s, 1H, OH), 7.40 (s, 1H, NH), 7.05 (dd, 1H, J=14.90), 6.86 (d, 1H, J=8.56), 6.75 (d, 1H, J=2.60), 6.60 (dd, 1H, J=8.60, 2.60), 6.10~6.35 (m, 4H), 5.86 (s, 1H), 2.58 (q, 2H, J=7.35), 2.42 (s, 3H), 2.01 (br s, 5H), 1.72 (s 3H), 1.58~1.62 (m, 2H), 1.45~1.47 (m, 2H), 1.21~1.29 (t, 3H, J=7.44), 1.02 (s, 6H). $^{13}$C NMR (100 MHz, $CDCl_3$): δ 172.69, 165.90, 151.86, 149.11, 148.89, 140.02, 137.66, 137.16, 134.88, 131.40, 130.09, 129.39, 128.93, 123.96, 122.34, 119.14, 113.33, 112.82, 39.55, 34.24, 33.89, 29.88, 28.92, 21.73, 19.25, 19.17, 13.80, 13.71, 12.93.

Example 16

2-[(2E,4E,6E,8E)-[3,7-dimethyl-9-(2,6,6-trimethylcyclohex-1-enyl)-nona-2,4,6,8-tetraenoylamino]-5-(3-methylbutyryloxy)phenyl-3-methylbutanoate (KCBG16)

and 2-[(2E,4E,6E,8E)-[3,7-dimethyl-9-(2,6,6-trimethylcyclohex-1-enyl)-nona-2,4,6,8-tetraenoylamino]-5-hydroxyphenyl-3-methylbutanoate (KCBG17)

(2E,4E,6E,8E)-[3,7-dimethyl-9-(2,6,6-trimethylcyclohex-1-enyl)-nona-2,4,6,8-tetraenoyl]-(2,4-dihydroxy)phenylamide (KCBG08) (0.051 g, 0.12 mmol) was dissolved in anhydrous $CH_2Cl_2$ (15 mL), and NMM (0.020 mL, 0.18 mmol) was added. To the resulting mixture was added dropwise isovaleryl chloride (0.016 mL, 0.18 mmol) at 0° C., and stirred for 0.5 h. The reaction mixture was extracted with $CH_2Cl_2$ and washed with $H_2O$ (2×20 mL). The organic layer was dried over $MgSO_4$ and evaporated in vacuo. The residue was purified by column chromatography over silica gel (EtOAc:hexane=1:5) to give 2-[(2E,4E,6E,8E)-[3,7-dimethyl-9-(2,6,6-trimethylcyclohex-1-enyl)-nona-2,4,6,8-tetraenoylamino]-5-(3-methylbutyryloxy)phenyl-3-methylbutanoate (KCBG16, 0.027 g, 38%) and 2-[(2E,4E,6E,8E)-[3,7-dimethyl-9-(2,6,6-trimethylcyclohex-1-enyl)-nona-2,4,6,8-tetraenoylamino]-5-hydroxyphenyl-3-methylbutanoate (KCBG17, 0.028 g, 45%).

2-[(2E,4E,6E,8E)-[3,7-dimethyl-9-(2,6,6-trimethylcyclohex-1-enyl)-nona-2,4,6,8-tetraenoylamino]-5-(3-methylbutyryloxy)phenyl-3-methylbutanoate $^1$H-NMR (200 MHz, $CDCl_3$): δ 8.24 (br s, 1H), 7.18 (br s, 1H), 6.92~7.02 (m, 4H), 6.09~6.32 (m, 4H), 5.73 (s, 1H),

[continued from previous page] 109.97, 63.12, 55.66, 45.84, 39.53, 34.22, 33.05, 29.15, 28.92, 21.73, 19.14, 14.10, 12.95.

2.42~2.49 (m, 4H), 2.41 (s, 3H), 2.21~225 (m, 2H), 2.01 (br s, 5H), 1.72 (s 3H), 1.58~1.62 (m, 2H), 1.45~1.47 (m, 2H), 1.03~1.08 (m, 12H), 1.02 (s, 6H).

$^{13}$C NMR (100 MHz, CDCl$_3$): δ 171.27, 170.30, 151.33, 140.42, 139.56, 137.68, 137.21, 135.03, 130.90, 130.79, 130.57, 129.98, 129.40, 128.80, 127.72, 122.65, 119.23, 115.78, 43.19, 39.55, 34.24, 33.07, 32.69, 30.02, 29.67, 28.93, 25.90, 25.73, 22.38, 21.73, 21.05, 19.52, 19.18, 17.54, 13.71, 12.89.

2-[(2E,4E,6E,8E)-[3,7-dimethyl-9-(2,6,6-trimethyl-cyclohex-1-enyl)-nona-2,4,6,8-tetraenoylamino]-5-hydroxyphenyl-3-methylbutanoate (KCBG17)

$^1$H-NMR (200 MHz, CDCl$_3$): δ 9.59 (s, 1H, OH), 7.39 (s, 1H, NH), 7.04 (dd, 1H, J=14.90), 6.86 (d, 1H, J=8.56), 6.75 (d, 1H, J=2.60), 6.60 (dd, 1H, J=8.60, 2.60), 6.10~6.35 (m, 4H), 5.86 (s, 1H), 2.39~2.42 (m, 2H), 2.42 (s, 3H), 2.01 (br s, 5H), 1.72 (s, 3H), 1.58~1.62 (m, 2H), 1.45~1.47 (m, 2H), 0.98~1.05 (m, 6H), 1.02 (s, 6H).

$^{13}$C NMR (100 MHz, CDCl$_3$): δ 171.94, 166.89, 153.16, 152.73, 150.15, 149.09, 139.98, 137.67, 137.19, 134.91, 131.37, 130.08, 129.40, 128.91, 124.02, 122.51, 120.54, 119.11, 118.84, 113.23, 112.88, 105.15, 43.31, 43.25, 39.56, 34.24, 33.09, 29.67, 28.94, 25.89, 22.37, 21.74, 19.18, 13.82, 12.93.

Example 17

[(2E,4E,6E,8E)-[3,7-dimethyl-9-(2,6,6-trimethylcyclohex-1-enyl)-nona-2,4,6,8-tetraenoylamino]-5-pentanoyloxyphenylpentanoate (KCBG18) and 2-[(2E,4E,6E,8E)-[3,7-dimethyl-9-(2,6,6-trimethyl-cyclohex-1-enyl)-nona-2,4,6,8-tetraenoylamino]-5-hydroxyphenylpentanoate (KCBG19)

(2E,4E,6E,8E)-[3,7-dimethyl-9-(2,6,6-trimethylcyclohex-1-enyl)-nona-2,4,6,8-tetraenoyl]-(2,4-dihydroxy)phenylamide (KCBG08) (0.051 g, 0.12 mmol) was dissolved in anhydrous CH$_2$Cl$_2$ (15 mL), and NMM (0.020 mL, 0.18 mmol) was added. To the resulting mixture was added dropwise valeryl chloride (0.021 mL, 0.18 mmol) at 0° C., and stirred for 0.5 h. The reaction mixture was extracted with CH$_2$Cl$_2$ and washed with H$_2$O (2×20 mL). The organic layer was dried over MgSO$_4$ and evaporated in vacuo. The residue was purified by column chromatography over silica gel (EtOAc:hexane=1:5) to give 2-[(2E,4E,6E,8E)-[3,7-dimethyl-9-(2,6,6-trimethylcyclohex-1-enyl)-nona-2,4,6,8-tetraenoylamino]-5-pentanoyloxyphenylpentanoate (KCBG18, 0.026 g, 36%) and 2-[(2E,4E,6E,8E)-[3,7-Dimethyl-9-(2,6,6-trimethylcyclohex-1-enyl)-nona-2,4,6,8-tetraenoylamino]-5-hydroxyphenyl pentanoate (KCBG19, 0.028 g, 45%).

[(2E,4E,6E,8E)-[3,7-Dimethyl-9-(2,6,6-trimethylcyclohex-1-enyl)-nona-2,4,6,8-tetraenoylamino]-5-pentanoyloxyphenylpentanoate (KCBG18)

$^1$H-NMR (200 MHz, CDCl$_3$): δ 8.24 (br s, 1H), 7.13 (br s, 1H), 6.93~7.02 (m, 4H), 6.09~6.32 (m, 4H), 5.73 (s, 1H), 2.554 (t, 2H, J=7.43), 2.557 (t, 2H, J=7.44), 2.41 (s, 3H), 2.01 (br s, 5H), 1.79~1.68 (m, 4H), 1.72 (s, 3H), 1.58~1.62 (m, 2H), 1.45~1.47 (m, 2H), 1.02 (s, 6H), 0.88~1.01 (m, 6H).

$^{13}$C NMR (100 MHz, CDCl$_3$): δ 171.99, 171.01, 153.10, 151.22, 139.51, 137.67, 137.21, 135.03, 130.75, 129.95, 129.40, 128.65, 127.70, 120.54, 119.14, 118.76, 115.71, 105.15, 39.54, 34.22, 34.00, 33.06, 28.92, 26.28, 26.92, 26.87, 22.23, 22.19, 21.72, 19.17, 13.71, 13.69, 12.89.

2-[(2E,4E,6E,8E)-[3,7-Dimethyl-9-(2,6,6-trimethyl-cyclohex-1-enyl)-nona-2,4,6,8-tetraenoylamino]-5-hydroxyphenylpentanoate (KCBG19)

$^1$H-NMR (200 MHz, CDCl$_3$): δ 9.61 (s, 1H, OH), 7.52 (s, 1H, NH), 7.05 (dd, 1H, J=14.90), 6.86 (d, 1H, J=8.60), 6.73 (d, 1H, J=2.50), 6.57 (dd, 1H, J=8.60, 2.50), 6.10~6.35 (m, 4H), 5.86 (s, 1H), 2.54 (t, 2H, J=7.40), 2.41 (s, 3H), 2.01 (br s, 5H), 1.71~1.89 (m, 2H), 1.72 (s 3H), 1.58~1.62 (m, 2H), 1.45~1.47 (m, 4H), 1.02 (s, 6H), 0.93~1.03 (m, 3H).

$^{13}$C NMR (100 MHz, CDCl$_3$): δ 172.67, 166.90, 152.78, 150.17, 149.16, 140.02, 137.66, 137.18, 134.89, 131.41, 130.10, 129.39, 128.92, 123.98, 122.51, 119.07, 113.23, 112.90, 39.56, 34.24, 34.09, 33.01, 28.94, 26.97, 22.21, 21.74, 19.18, 13.83, 13.72, 12.94.

Example 18

[(2E,4E,6E,8E)-3,7-Dimethyl-9-(2,6,6-trimethylcyclohex-1-enyl)-2,4,6,8-nonatetraenoyl]-(2-chloro-4-hydroxyphenyl)amide (KCBG27)

To a solution of 4-amino-3-chlorophenol (0.086 g, 0.48 mmol) in anhydrous DMF (5 mL) EDCI (0.092 g, 0.48 mmol) was added. The solution was stirred at room temperature for 0.5 h. To this mixture were added a solution of retinoic acid (0.072 g, 0.24 mmol) in anhydrous CH$_2$Cl$_2$ (10 mL) and DMAP (cat.). The resulting solution was stirred for 1 h, heated to 30° C. and again stirred for 4 h. The reaction was extracted with EtOAc (50 mL), washed with H$_2$O (2×50 mL), dried over Na$_2$SO$_4$ and evaporated. The crude compound was purified by flash column chromatography over silica gel (EtOAc:hexane=1:4) to give [(2E,4E,6E,8E)-3,7-Dimethyl-9-(2,6,6-trimethylcyclohex-1-enyl)-2,4,6,8-nonatetraenoyl]-(2-chloro-4-hydroxy)phenylamide (KCBG027, 0.030 g, 42%)

$^1$H-NMR (200 MHz, CDCl$_3$): δ 7.93 (d, 1H, J=8.56), 7.37 (br s, 1H), 7.05 (dd, 1H, J=14.90), 6.94 (d, 1H, J=2.60), 6.73 (dd, 1H, J=8.80, 2.60), 6.10~6.45 (m, 5H), 5.86 (s, 1H), 2.41 (s, 3H), 2.01 (br s, 5H), 1.72 (s 3H), 1.58~1.62 (m, 2H), 1.45~1.47 (m, 2H), 1.02 (s, 6H).

Example 19

3-Chloro-4-[(2E,4E,6E,8E)-3,7-dimethyl-9-(2,6,6-trimethylcyclohex-1-enyl)-2,4,6,8-nonatetraenoyl]phenylbutanoate (KCBG028)

To the solution of [(2E,4E,6E,8E)-3,7-Dimethyl-9-(2,6,6-trimethylcyclohex-1-enyl)-2,4,6,8-nonatetraenoyl]-(2-chloro-4-hydroxyphenyl)amide (KCBG027) (0.08 g, 0.18 mmol) in anhydrous CH$_2$Cl$_2$ (5 mL) was added NMM (0.024 mL, 0.23 mmol). To the resulting mixture was added dropwise butyryl chloride (0.024 mL, 0.23 mmol) in anhydrous CH$_2$Cl$_2$ (5 mL) at 0° C., and stirred for 0.5 h. The reaction mixture was extracted with EtOAc (50 mL) and washed with H$_2$O (2×30 mL). The organic layer was dried over MgSO$_4$ and evaporated in vacuo. The residue was purified by column chromatography over silica gel (EtOAc: hexane=1:5) to give 3-chloro-4-[(2E,4E,6E,8E)-3,7-dimethyl-9-(2,6,6-trimethylcyclohex-1-enyl)-2,4,6,8-nonatetraenoyl]phenyl butanoate (KCBG28, 0.008 g, 89%).

¹H-NMR (200 MHz, CDCl₃): δ 8.52 (d, 1H, J=8.90), 7.58 (s, 1H), 6.96~7.25 (m, 3H), 6.10~6.35 (m, 4H), 5.84 (s, 1H), 2.54 (t, 2H, J=7.40), 2.41 (s, 3H), 2.01 (br s, 5H), 1.71~1.89 (m, 2H), 1.72 (s 3H), 1.58~1.62 (m, 2H), 1.45~1.47 (m, 2H), 0.96~1.09 (m, 3H), 1.02 (s, 6H).

II. Preparation of Cartechol Derivatives

Example 20

4-Aminobenzene-1,2-diol (KYJ3-018)

To a solution of 4-nitro cartechol (0.052 g, 0.33 mmol) in MeOH (2 mL) was added Pd/C (10%, 0.005 g) at room temperature. After stirring for 30 min under H₂, the reaction mixture was filtered and evaporated in vacuo to give 4-Aminobenzene-1,2-diol (0.048 g, 100%) as a white solid.

Example 21

2-[(2E,4E,6E,8E)-[3,7-dimethyl-9-(2,6,6-trimethyl-cyclohex-1-enyl)-nona-2,4,6,8-tetraenoylamino]-(3,4-dihydroxyphenyl)amide (KYJ3-020)

To a cooled solution (0° C.) of EDCI (0.076 g, 0.39 mmol) in anhydrous DMF (5 mL) was added retinoic acid (0.10 g, 0.33 mmol). The solution was stirred at room temperature for 0.5 h. To this mixture were added a solution of 4-amino cartechol (0.048 g, 0.39 mmol) and DMAP (cat.) in anhydrous DMF (5 mL), and stirred for 4 h at room temperature. The reaction was extracted with EtOAc (30 mL), washed with H₂O (2×30 mL), dried over Na₂SO₄ and evaporated. The crude compound was purified by flash column chromatography over silica gel (EtOAc:hexane=1:4) to give 2-[(2E,4E,6E,8E)-[3,7-dimethyl-9-(2,6,6-trimethylcyclohex-1-enyl)-nona-2,4,6,8-tetraenoylamino]-(3,4-dihydroxyphenyl)amide (KYJ3-020, 0.093 g, 69%).

¹H-NMR (200 MHz, CDCl₃): δ 7.67 (s, 1H), 7.26 (s, 1H), 7.05 (dd, 1H, J=14.90), 6.78 (d, 1H, J=8.50), 6.55 (dd, 1H, J=8.50, 2.50), 6.10~6.35 (m, 4H), 5.81 (s, 1H), 2.36 (s, 3H), 2.01 (br s, 5H), 1.72 (s 3H), 1.58~1.62 (m, 2H), 1.45~1.49 (m, 2H), 1.02 (s, 6H).

¹³C NMR (100 MHz, CDCl₃): δ 171.26, 166.17, 150.29, 144.18, 141.93, 139.42, 137.69, 137.25, 135.01, 130.61, 130.13, 129.96, 129.46, 128.58, 121.13, 114.77, 112.55, 109.13, 60.43, 39.58, 34.24.33.09, 28.94, 21.74, 21.04, 19.20, 14.17, 14.00, 12.89.

Example 22

2-Butyryloxy-5-(2E,4E,6E,8E)-[3,7-dimethyl-9-(2,6,6-trimethylcyclohex-1-enyl)-nona-2,4,6,8-tetraenoylamino]phenylbutanoate (KCBG34) and 5-(2E,4E,6E,8E)-[3,7-dimethyl-9-(2,6,6-trimethylcyclohex-1-enyl)-nona-2,4,6,8-tetraenoylamino]-2-hydroxyphenylbutanoate (KCBG35)

To a solution of KYJ3-020 (0.051 g, 0.12 mmol) in anhydrous CH₂Cl₂ (15 mL) was added NMM (0.019 g, 0.18 mmol). To the resulting mixture was added dropwise butyryl chloride (0.019 mL, 0.18 mmol)) in anhydrous CH₂Cl₂ (5 mL) at 0° C., and stirred for 0.5 h. The reaction mixture was washed with H₂O (2×20 mL). The organic layer was dried over MgSO₄ and evaporated in vacuo. The residue was purified by column chromatography over silica gel (EtOAc:hexane=1:5) to give 2-butyryloxy-5-(2E,4E,6E,8E)-[3,7-dimethyl-9-(2,6,6-trimethylcyclohex-1-enyl)-nona-2,4,6,8-tetraenoylamino]phenylbutanoate (KCBG34, 19 mg, 30%) and 5-(2E,4E,6E,8E)-[3,7-dimethyl-9-(2,6,6-trimethylcyclohex-1-enyl)-nona-2,4,6,8-tetraenoylamino]-2-hydroxyphenylbutanoate (KCBG35, 28 mg, 50%).

Example 23

2-Butyryloxy-5-nitrophenylbutanoate (KYJ2-181A) and 2-Hydroxy-5-nitrophenyl butanoate (KYJ2-181B)

To a solution of 4-nitrocartechol (1.0 g, 6.44 mmol) in anhydrous CH₂Cl₂ (30 mL) was added TEA (triethylamine, 1.34 mL, 9.67 mmol). To the resulting mixture was added dropwise butyryl chloride (1.0 mL, 9.67 mmol)) in anhydrous CH₂Cl₂ (2 mL) at 0° C., and stirred for 0.5 h. The reaction mixture was washed with H₂O (2×30 mL). The organic layer was dried over MgSO₄ and evaporated in vacuo. The residue was purified by column chromatography over silica gel (EtOAc:hexane=1:6) to give 2-butyryloxy-5-nitrophenylbutanoate (KYJ2-181A, 0.58 g, 30%) and 2-hydroxy-5-nitrophenylbutanoate (KYJ2-181B, 1.1 g, 69%).

2-Butyryloxy-5-nitrophenylbutanoate (KYJ2-181A)

¹H-NMR (200 MHz, CDCl₃): δ 8.12~8.16 (m, 2H), 7.38 (d, 1H, J=8.70), 2.56 (t, 4H, J=7.31), 1.73~1.84 (m, 4H), 1.051 (t, 3H, J=7.45), 1.05 (t, 3H, J=7.43).

2-Hydroxy-5-nitrophenylbutanoate (KYJ2-181B)

¹H-NMR (200 MHz, CDCl₃): δ 8.07 (s, 1H), 8.02~8.07 (m, 1H), 7.80~7.83 (m, 1H), 7.03 (d, 1H, J=7.50), 2.65 (t, 2H, J=7.35), 1.77~1.88 (m, 2H), 1.07 (t, 3H, J=7.35).

Example 24

4-Aminocartechol-1,2-dibutyrate (KYJ2-183A)

To a solution of KYJ2-181A (0.15 g, 0.51 mmol) in MeOH (5 mL) was added Pd/C (10%, 0.015 g) at room temperature. After stirring for 0.5 h under H₂ gas, the reaction was filtered and evaporated in vacuo to give 4-aminocartechol-1,2-dibutyrate (KYJ2-183A, 0.13 g, 100%) as a white solid.

Example 25

2-Butyryloxy-5-(2E,4E,6E,8E)-[3,7-dimethyl-9-(2,6,6-trimethylcyclohex-1-enyl)-nona-2,4,6,8-tetraenoylamino]phenylbutanoate (KCBG34).

To a cooled solution (0° C.) of EDCI (0.12 g, 0.61 mmol) in anhydrous DMF (3 mL) was added retinoic acid (0.15 g, 0.51 mmol). The solution was stirred at room temperature for 0.5 h. To this mixture were added a solution of KYJ2-183A (0.13 g, 0.51 mmol) in anhydrous DMF (5 mL) and DMAP (cat.), and stirred for 4 h at room temperature. The reaction was extracted with EtOAc (50 mL), washed with H₂O (2×50 mL), dried over Na₂SO₄ and evaporated. The crude compound was purified by column chromatography over silica gel (EtOAc:hexane=1:5) to give 2-butyryloxy-5-(2E,4E,6E,8E)-[3,7-dimethyl-9-(2,6,6-trimethylcyclohex-1-enyl)-nona-2,4,6,8-tetraenoylamino]phenylbutanoate (KCBG34, 0.20 g, 75%).

¹H-NMR (200 MHz, CDCl₃): δ 7.65 (br s, 1H), 7.45 (br s, 1H), 6.92~7.01 (m, 4H), 6.10~6.31 (m, 4H), 5.72 (s, 1H), 2.40~2.54 (m, 4H), 2.41 (s, 3H), 2.01 (br s, 5H), 1.71~1.82 (m, 4H), 1.72 (s 3H), 1.58~1.62 (m, 2H), 1.45~1.47 (m, 2H), 0.96~1.09 (m, 6H), 1.02 (s, 6H).

$^{13}$C NMR (100 MHz, CDCl$_3$): δ 171.38, 171.32, 165.09, 150.74, 141.91, 139.25, 137.69, 137.25, 136.91, 135.38, 130.38, 129.88, 128.49, 128.49, 123.22, 121.19, 117.30, 114.69, 39.55, 35.82, 34.22, 33.06, 29.65, 28.91, 21.70, 19.18, 18.37, 18.35, 13.65, 13.62, 12.86.

Example 26

5-amino-2-hydroxy-phenylbutanoate(KYJ2-183B)

To a solution of KYJ2-181B (0.10 g, 0.44 mmol) in MeOH (5 mL) was added Pd/C (10%, 0.010 g) at room temperature. After stirring for 30 min under H$_2$ gas, the reaction was filtered and evaporated in vacuo to give 5-amino-2-hydroxyphenylbutanoate (KYJ2-183B, 0.086 g, 100%) as a white solid.

Example 27

5-(2E,4E,6E,8E)-[3,7-dimethyl-9-(2,6,6-trimethylcyclohex-1-enyl)-nona-2,4,6,8-tetraenoylamino]-2-hydroxyphenylbutanoate (KCBG35)

To a cooled solution (0° C.) of EDCI (0.12 g, 0.61 mmol) in anhydrous DMF (3 mL) was added retinoic acid (0.13 g, 0.44 mmol). The solution was stirred at room temperature for 0.5 h. To this mixture were added a solution of 4-aminocartechol-2-butyrate (KYJ2-183B, 0.086 g, 0.44 mmol) in anhydrous DMF (5 mL) and DMAP (cat.), and stirred for 4 h at room temperature. The reaction was extracted with EtOAc (50 mL), washed with H$_2$O (2×50 mL), dried over Na$_2$SO$_4$ and evaporated. The crude compound was purified by column chromatography over silica gel (EtOAc:hexane=1:5) to give 5-(2E,4E,6E,8E)-[3,7-dimethyl-9-(2,6,6-trimethylcyclohex-1-enyl)-nona-2,4,6,8-tetraenoylamino]-2-hydroxyphenylbutanoate (KCBG35, 0.14 g, 68%).

$^1$H-NMR (200 MHz, CDCl$_3$): δ 7.58 (br s, 1H), 7.48 (br s, 1H), 6.83~7.01 (m, 3H), 6.60 (d, 1H, J=8.80), 6.10~6.31 (m, 4H), 5.81 (s, 1H), 2.57 (t, 2H, J=7.35), 2.41 (s, 3H), 2.01 (br s, 5H), 1.71~1.89 (m, 2H), 1.72 (s 3H), 1.58~1.62 (m, 2H), 1.45~1.47 (m, 2H), 1.02 (s, 6H), 1.01~1.08 (m, 3H).

$^{13}$C NMR (100 MHz, CDCl$_3$): δ 171.78, 164.98, 148.41, 138.39, 139.34, 137.17, 136.95, 135.52, 135.46, 129.44, 129.33, 127.86, 122.29, 122.17, 110.36, 108.33, 35.54, 33.89, 32.72, 28.61, 21.42, 18.85, 18.11, 18.06, 13.34, 13.24, 12.54.

Example 28

2-Butyrylamino-4-nitrophenylbutanoate (KYJ3-007A) and

2-Amino N-(2-hydroxy-5-nitrophenyl)butyramide (KYJ3-007B)

To a solution of 2-amino-4-nitrophenol (1.01 g, 6.48 mmol) in anhydrous CH$_2$Cl$_2$ (30 mL) was added TEA (triethylamine, 1.35 mL, 9.72 mmol). To the resulting mixture was added dropwise butyryl chloride (0.95 mL, 9.72 mmol) in anhydrous CH$_2$Cl$_2$ (5 mL) at 0° C., and stirred for 0.5 h. The reaction mixture was washed with H$_2$O (2×30 ml). The organic layer was dried over MgSO$_4$ and evaporated in vacuo. The residue was purified by column chromatography over silica gel (EtOAc:hexane=1:4) to give 2-butyrylamino-4-nitrophenylbutanoate (KYJ3-007A, 0.70 g, 36.8%) and 2-amino N-(2-hydroxy-5-nitrophenyl)butyramide (KYJ3-007B, 0.91 g, 63%).

Example 29

2-Butyrylamino-4-nitrophenylbutanoate (KYJ3-007A)

To a solution of 2-amino-4-nitrophenol (0.51 g, 3.24 mmol) in anhydrous CH$_2$C$_2$ (20 mL) was added TEA (triethylamine, 1.81 mL, 12.96 mmol). To the resulting mixture was added dropwise butyryl chloride (1.23 mL, 12.96 mmol) in anhydrous CH$_2$Cl$_2$ (5 mL) at 0° C., and stirred for 0.5 h. The reaction mixture was washed with H$_2$O (2×30 mL). The organic layer was dried over MgSO$_4$ and evaporated in vacuo. The crude product was recrystallized from EtOAc:hexane (1:3) to give 2-butyrylamino-4-nitrophenylbutanoate (KYJ3-007A, 0.90 g, 95%) as a white needle.

$^1$H-NMR (200 MHz, CDCl$_3$): δ 9.23 (br s, 1H), 8.00 (dd, 1H, J=9.01, 2.82), 7.34 (d, 2H, J=9.01), 2.66 (t, 2H, J=7.33), 2.39 (t, 2H, J=7.33), 1.71~1.88 (m, 4H), 1.055 (t, 3H, J=7.34), 1.053 (t, 3H, J=7.33).

$^{13}$C NMR (100 MHz, CDCl$_3$): δ 171.13, 170.19, 145.34, 144.18, 130.58, 122.42, 119.15, 117.31, 39.48, 36.06, 18.71, 18.33, 13.62, 13.55.

Example 30

2-Amino N-(2-hydroxy-5-nitrophenyl)butyramide (KYJ3-007B)

To a solution of 2-amino-4-nitrophenol 1,2-dibutyrate (KYJ3-007A, 0.5 g) in anhydrous CH$_2$C$_2$ (5 mL) and MeOH (2 mL) was added finely ground K$_2$CO$_3$ (0.5 g) at the temperature of from 0° C. to 10° C. After stirring for 0.5 h, the reaction was extracted with CH$_2$Cl$_2$ (30 mL), and washed with H$_2$O (20 ml). The organic layer was dried over MgSO$_4$ and evaporated in vacuo. The crude product was recrystallized from EtOAc/hexane(1:3) to give 2-amino N-(2-hydroxy-5-nitrophenyl)butyramide (KYJ3-007B, 0.34 g, 89%) as a pale brown solid.

$^1$H-NMR (200 MHz, CDCl$_3$): δ 8.91 (br s, 1H), 8.80 (br s, 1H), 7.81~7.87 (m, 1H), 6.97 (dd, 1H, J=8.80, 0.88), 2.43 (t, 2H, J=7.28), 1.68~1.79 (m, 2H), 1.00 (t, 3H, J=7.24).

$^{13}$C NMR (100 MHz, CDCl$_3$): δ 174.56, 154.85, 149.02, 135.07, 125.72, 122.95, 120.06, 118.06, 115.55, 114.09, 111.16, 38.76, 19.08, 13.59.

Example 31

4-Amino-2-butyrylaminophenylbutanoate (KYJ3-056)

To a solution of KYJ3-007A (2.21 g, 7.47 mmol) in anhydrous CH$_2$Cl$_2$ (2 mL) and MeOH (10 mL) was added Pd/C (10%, 0.15 g)at room temperature. After stirring for 0.5 h under H$_2$ gas, the reaction was filtered and evaporated in vacuo to give 4-amino-2-butyrylaminophenylbutanoate (KYJ3-056, 1.97 g, 100%) as a pale brown oil.

Example 32

2-Butyrylamino-4-(2E,4E,6E,8E)-[3,7-dimethyl-9-(2,6,6-trimethylcyclohex-1-enyl)-nona-2,4,6,8-tetraenoylamino]-phenylbutanoate (KCBG42)

To a cooled solution (0° C.) of retinoic acid (2.24 g, 7.45 mmol) in anhydrous DMF (5 mL) was added EDCI (1.71 g, 8.94 mmol). The solution was stirred at room temperature for 0.5 h. To this mixture were added a solution of KYJ3-056 (1.97 g, 7.45 mmol) in anhydrous DMF (5 mL) and DMAP (cat.), and stirred for 4 h at room temperature. The reaction was extracted with EtOAc (100 mL), washed with $H_2O$ (2×100 mL), dried over $Na_2SO_4$, and evaporated. The crude compound was purified by column chromatography over silica gel (EtOAc:hexane=1:5) to give 2-butyrylamino-4-(2E,4E,6E,8E)-[3,7-dimethyl-9-(2,6,6-trimethylcyclohex-1-enyl)-nona-2,4,6,8-tetraenoylamino]phenylbutanoate (KCBG42, 2.43 g, 68%) as a yellow solid.

$^1$H-NMR (200 MHz, $CDCl_3$): δ 7.89 (d, 2H, J=6.85), 7.54 (d, 1H, J=8.75), 7.35 (br s, 1H), 6.90~7.03 (m, 3H), 6.10~6.31 (m, 4H), 5.74 (s, 1H), 2.54 (t, 2H, J=7.32), 2.41 (s, 3H), 2.31 (t, 2H, J=7.44), 2.01 (br s, 5H), 1.71~1.82 (m, 4H), 1.72 (s 3H), 1.58~1.62 (m, 2H), 1.45~1.47 (m, 2H), 0.96~1.09 (m, 6H), 1.02 (s, 6H).

$^{13}$C NMR (100 MHz, $CDCl_3$): δ 171.74, 171.60, 165.23, 150.34, 139.03, 137.70, 137.39, 137.32, 136.51, 135.59, 130.13, 129.84, 129.60, 129.39, 128.34, 122.22, 121.50, 116.98, 115.23, 39.56, 39.30, 36.03, 34.23, 33.07, 28.93, 21.72, 19.20, 19.02, 18.45, 13.70, 13.65, 13.62, 12.86.

Example 33

N-(5-Amino-2-hydroxyphenyl)butyramide (KYJ3-057)

To a solution of KYJ3-007B (2.02 g, 9.00 mmol) in anhydrous $CH_2Cl_2$ (2 mL) and MeOH (10 mL) was added Pd/C (10%, 0.15 g) at room temperature. After stirring for 4 h under $H_2$ gas, the reaction was filtered and evaporated in vacuo N-(5-amino-2-hydroxyphenyl)butyramide (KYJ3-057, 1.56 g, 89%) as a pale brown solid.

Example 34

(2E,4E,6E,8E)-[3,7-dimethyl-9-(2,6,6-trimethylcyclohex-1-enyl)-nona-2,4,6,8-tetraenoylamino]-(3-butyrylamino-4-hydroxy)phenylamide (KCBG41)

To a cooled solution (0° C.) of retinoic acid (2.39 g, 7.98 mmol) in anhydrous DMF (5 mL) was added EDCI (1.83 g, 9.57 mmol). The solution was stirred at room temperature for 0.5 h. To this mixture were added a solution of KYJ3-057 (1.56 g, 7.98 mmol) in anhydrous DMF (5 mL) and DMAP (cat.), and stirred for 4 h at room temperature. The reaction was extracted with EtOAc (100 mL), washed with $H_2O$ (2×100 mL), dried over $Na_2SO_4$, and evaporated. The crude compound was purified by column chromatography over silica gel (EtOAc:hexane=1:5) to give (2E,4E,6E,8E)-[3,7-dimethyl-9-(2,6,6-trimethylcyclohex-1-enyl)-nona-2,4,6,8-tetraenoylamino]-(3-butyrylamino-4-hydroxy)phenylamide (KCBG41, 2.23 g, 59%).

$^1$H-NMR (200 MHz, $CDCl_3$): δ 7.72 (bs, 1H), 7.20 (bs, 1H), 7.12 (dd, 1H, J=14.9), 6.90 (d, 1H, J=8.7), 6.12~6.43 (m, 6H), 6.00 (s, 1H), 2.41 (s, 3H), 2.32 (t, 2H, J=7.44), 2.01 (bs, 5H), 1.72 (s 3H), 1.58~1.76 (m, 4H), 1.45~1.47 (m, 2H), 1.02 (s, 6H), 0.95~1.01 (t, 3H, J=7.38).

$^{13}$C NMR (100 MHz, $CDCl_3$): δ 171.02, 165.21, 156.63, 144.56, 140.91, 137.60, 137.04, 134.36, 132.56, 132.10, 130.54, 130.32, 129.42, 129.20, 122.48, 116.02, 110.36, 108.17, 39.77, 39.54, 34.22, 33.09, 28.92, 21.72, 19.15, 18.92, 14.13, 13.63, 12.95.

Example 35

[(2E,4E,6E,8E)-3,7-dimethyl-9-(2,6,6-trimethyl-1-cyclohexenyl)-2,4,6,8-nonatetraenoyl]-(3-hydroxy-4-methoxyphenyl)amide (KCBG025)

To a solution of 5-amino-2-methoxyphenol (0.066 g, 0.48 mmol)) in anhydrous DMF (10 mL) was added EDCI (0.092 g, 0.48 mmol). The solution was stirred at room temperature for 0.5 h. To this mixture were added a solution of retinoic acid (0.072 g, 0.24 mmol) in anhydrous $CH_2Cl_2$ (10 mL) and DMAP (cat.), stirred for 1 h at room temperature and heated to 30° C. for 4 h. The reaction was extracted with EtOAc (50 mL), washed with $H_2O$ (2×50 mL), dried over $Na_2SO_4$, and evaporated. The crude compound was purified by column chromatography over silica gel (EtOAc:hexane=1:4) to give [(2E,4E,6E,8E)-3,7-dimethyl-9-(2,6,6-trimethyl-1-cyclohexenyl)-2,4,6,8-nonatetraenoyl]-(3-hydroxy-4-methoxyphenyl)amide (KCBG25, 0.054 g, 54%).

$^1$H-NMR (200 MHz, $CDCl_3$): δ 7.04~7.07 (m, 2H), 7.05 (dd, 1H, J=14.90), 6.79 (d, 1H, J=8.64), 6.10~6.30 (m, 4H), 5.77 (s, 1H), 3.86 (s, 3H), 2.41 (s, 3H), 2.01 (br s, 5H), 1.72 (s 3H), 1.58~1.62 (m, 2H), 1.45~1.47 (m, 2H), 1.02 (s, 6H).

$^{13}$C NMR (100 MHz, $CDCl_3$): δ 150.32, 145.73, 139.18, 137.72, 135.34, 130.29, 129.91, 129.55, 128.58, 127.69, 127.00, 121.33, 110.85, 107.13, 56.20, 39.58, 34.25, 33.10, 28.96, 21.76, 19.22, 18.19, 13.60, 12.90.

Example 36

5-[(2E,4E,6E,8E)-3,7-dimethyl-9-(2,6,6-trimethyl-1-cyclohexenyl)-2,4,6,8-nonatetraenoyl]-amino-2-methoxyphenylbutanoate (KCBG26)

To a solution of 5-amino-(N-retinyl)-2-methoxyphenol (0.10 g, 0.25 mmol) in anhydrous $CH_2Cl_2$ (5 mL) was added NMM (0.033 mL, 0.31 mmol). To the resulting mixture was added dropwise butyryl chloride (0.032 mL, 0.31 mmol) in anhydrous $CH_2Cl_2$ (5 mL) at 0° C., and stirred for 0.5 h. The reaction mixture was extracted with EtOAc (50 mL), and washed with $H_2O$ (2×30 mL). The organic layer was dried over $MgSO_4$ and evaporated in vacuo. The crude product was purified by column chromatography over silica gel (EtOAc:hexane=1:5) to give 5-[(2E,4E,6E,8E)-3,7-dimethyl-9-(2,6,6-trimethyl-1-cyclohexenyl)-2,4,6,8-nonatetraenoyl]-amino-2-methoxyphenyl butanoate (KCBG26, 0.097 g, 79%).

$^1$H-NMR (200 MHz, $CDCl_3$): δ 7.42 (br s, 1H), 7.31 (br s, 1H), 7.15~7.25 (m, 1H), 7.05 (dd, 1H, J=14.90), 6.85 (d, 1H, J=8.64), 6.10~6.35 (m, 4H), 5.70 (s, 1H), 2.57 (t, 2H, J=7.35), 2.41 (s, 3H), 2.01 (br s, 5H), 1.71~1.89 (m, 2H), 1.72 (s 3H), 1.58~1.62 (m, 2H), 1.45~1.47 (m, 2H), 0.96~1.09 (m, 3H), 1.02 (s, 6H).

$^{13}$C NMR (100 MHz, $CDCl_3$): δ 172.21, 164.95, 150.24, 147.44, 139.37, 139.13, 137.68, 137.25, 135.42, 131.81, 130.20, 129.88, 129.52, 128.41, 121.28, 117.69, 115.30, 112.34, 50.96, 39.54, 35.83, 34.22, 33.06, 28.91, 25.86, 21.72, 21.06, 18.49, 13.57, 12.86.

III. Preparation Of HPR Derivatives

Example 37

(2E,4E,6E,8E)-[3,7-dimethyl-9-(2,6,6-trimethylcyclohex-1-enyl)-nona-2,4,6,8-tetraenoylamino]-4-hydroxyphenylamide (HPR)

To a solution of retinoic acid (1.01 g, 3.33 mmol)) in anhydrous DMF (5 mL) was added EDCI (0.76 g, 3.99 mmol). The solution was stirred at room temperature for 0.5 h. To this mixture were added a solution of 4-amino phenol (0.43 g, 3.99 mmol) in anhydrous DMF (5 mL) and DMAP (cat.), and stirred for 4 h at room temperature. The reaction was extracted with EtOAc (50 mL), washed with $H_2O$ (2×50 mL), dried over $Na_2SO_4$, and evaporated. The crude compound was purified by column chromatography over silica gel (EtOAc:hexane=1:4) to give (2E,4E,6E,8E)-[3,7-dimethyl-9-(2,6,6-trimethylcyclohex-1-enyl)-nona-2,4,6,8-tetraenoylamino]-4-hydroxyphenylamide (HPR, 1.01 g, 78%).

Example 38

(2E,4E,6E,8E)-[3,7-dimethyl-9-(2,6,6-trimethylcyclohex-1-enyl)-nona-2,4,6,8-tetraenoylamino]-4-hydroxyphenylamide (HPR)

A mixture of anhydrous DMF (2 mL) and $SOCl_2$ (0.072 mL, 0.99 mmol) was stirred under argon for 1 h. To the solution was added retinoic acid (0.10 g, 0.33 mmol) in anhydrous DMF (2 mL). After stirring at 0° C. for 45 minutes in subdued light, the clear deep red retinoyl chloride solution was added dropwise to a cooled solution of triethylamine (0.14 mL, 0.99 mmol) and 4-aminophenol (0.10 g, 0.66 mmol) in dry, degassed DMF (2 mL). This solution was added dropwise to the solution previously prepared. The resulting solution was stirred for 1 h while being kept at 0° C. The reaction was quenched with $NH_4Cl$ (aq.), extracted with EtOAc (30 mL). The extracts were washed with $H_2O$ (2×30 mL), dried over $Na_2SO_4$, and evaporated. The residue was purified by column chromatography over silica gel (EtOAc:hexane=1:4) to give (2E,4E,6E,8E)-[3,7-dimethyl-9-(2,6,6-trimethylcyclohex-1-enyl)-nona-2,4,6,8-tetraenoylamino]-4-hydroxyphenylamide (HPR, 0.12 g, 96%) as a yellow solid.

Example 39

N-(4-Amino-phenyl)butyramide (KYJ3-006-2)

To a solution of 1,4-phenylenediamine (0.5 g, 4.62 mmol) in anhydrous $CH_2Cl_2$ (15 mL) was added NMM (0.51 mL, 4.62 mmol). To the resulting mixture was added dropwise butyryl chloride (0.45 mL, 4.62 mmol) in anhydrous $CH_2Cl_2$ (5 mL) at 0° C., and stirred for 0.5 h. The reaction mixture was extracted with $CH_2Cl_2$ (20 mL) and washed with $H_2O$ (20 mL). The organic layer was dried over $MgSO_4$ and evaporated in vacuo. The residue was purified by column chromatography over silica gel (EtOAc:hexane=1:3) to give N-(4-aminophenyl)butyramide (KYJ3-006-2, 0.31 g, 36%) as a colorless oil.

$^1$H NMR (200 MHz, $CDCl_3$): δ 7.28 (d, 2H, J=8.60), 7.09 (br s, 1H), 6.65 (d, 2H, J=8.60), 2.30 (t, 2H, J=7.44), 1.75 (q, 2H, J=7.45), 1.00 (t, 3H, J=7.44).

$^{13}$C NMR (100 MHz, $CDCl_3$): δ 171.03, 143.08, 129.29, 121.98, 115.36, 39.45, 19.15, 13.75

Example 40

(2E,4E,6E,8E)-[3,7-dimethyl-9-(2,6,6-trimethylcyclohex-1-enyl)-nona-2,4,6,8-tetraenoylamino]-(4-butyrylamino)phenylamide (KCBG40)

To a cooled solution (0° C.) of retinoic acid (0.50 g, 1.68 mmol) in anhydrous DMF (5 mL) was added EDCI (0.38 g, 2.01 mmol), and stirred for 0.5 h at room temperature. To the reaction mixture were added a solution of KYJ3-006-2 (0.30 g, 1.68 mmol) in anhydrous DMF (5 mL) and DMAP (cat.). After stirring for 4 h at room temperature, the reaction was extracted with EtOAc (30 mL), washed with $H_2O$ (2×30 mL), dried over $Na_2SO_4$, and evaporated. The crude compound was purified by column chromatography over silica gel (EtOAc:hexane=1:5) to give (2E,4E,6E,8E)-[3,7-dimethyl-9-(2,6,6-trimethylcyclohex-1-enyl)-nona-2,4,6,8-tetraenoylamino]-(4-butyrylamino)phenylamide (KCBG40, 0.46 g, 60%).

Example 41

(2E,4E,6E,8E)-[3,7-dimethyl-9-(2,6,6-trimethylcyclohex-1-enyl)-nona-2,4,6,8-tetraenoylamino]-(4-butyrylamino)phenylamide (KCBG40)

To a solution of 4-nitro aniline (1.01 g, 7.23 mmol) in anhydrous $CH_2Cl_2$ (20 mL) was added NMM (0.95 mL, 8.68 mmol). To the reaction mixture was added dropwise butyryl chloride (1.00 mL, 8.68 mmol) at 0° C. After stirring for 0.5 h, the reaction was extracted with $CH_2Cl_2$ (20 mL), washed with $H_2O$ (30 mL), dried over $Na_2SO_4$, and evaporated in vacuo to give N-(4-Nitrophenyl)butyramide (1.50 g, 100%) as a white solid.

To a solution of 4-nitro aniline-1-butyrate (1.50 g, 7.20 mmol) in MeOH (10 mL) and $CH_2Cl_2$ (2 mL) was added Pd/C (10%, 0.12 g) at room temperature. After stirring for 3 h under $H_2$ gas, the reaction was filtered and evaporated in vacuo to give N-(4-aminophenyl)butyramide (1.28 g, 100%) as a pale brown solid.

To a cooled solution (0° C.) of retinoic acid (2.16 g, 7.20 mmol) in anhydrous DMF (5 mL) was added EDCI (1.65 g, 8.64 mmol) in anhydrous DMF (2 mL) and stirred for 0.5 h at room temperature. To the reaction mixture were added a solution of N-(4-aminophenyl)butyramide (1.28 g, 7.20 mmol) in anhydrous DMF (5 mL) and DMAP (cat.). After stirring for 4 h at room temperature, the reaction was extracted with EtOAc (100 mL), washed with $H_2O$ (2×100 mL), dried over $Na_2SO_4$, and evaporated. The crude compound was purified by column chromatography over silica gel (EtOAc:hexane=1:5) to give (2E,4E,6E,8E)-[3,7-dimethyl-9-(2,6,6-trimethylcyclohex-1-enyl)-nona-2,4,6,8-tetraenoylamino]-(4-butyrylamino)phenylamide (KCBG40, 2.09 g, 63%).

$^1$H-NMR (200 MHz, $CDCl_3$): δ 7.39~7.49 (m, 4H), 7.12 (dd, 1H, J=14.90), 6.90 (d, 1H, J=8.70), 6.09~6.35 (m, 4H), 5.91 (s, 1H), 2.39 (s, 3H), 2.32 (t, 2H, J=7.45), 2.01 (br s, 5H), 1.72 (s 3H), 1.58~1.76 (m, 4H), 1.45~1.47 (m, 2H), 1.02 (s, 6H), 0.95~1.01 (t, 3H, J=7.45).

$^{13}$C NMR (100 MHz, $CDCl_3$): δ 171.70, 139.25, 137.69, 137.26, 135.35, 130.36, 129.93, 129.52, 128.50, 120.95, 120.70, 39.57, 39.38, 34.24, 33.08, 28.94, 21.74, 19.20, 19.08, 13.75, 13.69, 12.89.

Example 42

4-[(2E,4E,6E,8E)-3,7-dimethyl-9-(2,6,6-trimethyl-1-cyclohexenyl)-2,4,6,8-nonatetraenoyl]aminophenyl-2-oxopropanoate (KCBG45)

To a solution of pyruvic acid (0.017 mL, 0.24 mmol) in anhydrous CH$_2$Cl$_2$ (5 mL) was added EDCI (0.047 g, 0.24 mmol) in anhydrous CH$_2$Cl$_2$ (2 mL) and stirred for 0.5 h at room temperature. To the reaction mixture were added HPR (0.047 g, 0.12 mmol) in anhydrous CH$_2$Cl$_2$ (2 mL) and DMAP (cat.). After stirring for 1 h at room temperature and heated to 30° C. for 3 h, the reaction was extracted with EtOAc (30 mL), washed with H$_2$O (2×30 mL), dried over Na$_2$SO$_4$, and evaporated. The crude compound was purified by column chromatography over silica gel (EtOAc:hexane=1:4) to give 4-[(2E,4E,6E,8E)-3,7-dimethyl-9-(2,6,6-trimethyl-1-cyclohexenyl)-2,4,6,8-nonatetraenoyl]aminophenyl-2-oxopropanoate (KCBG45, 0.028 g, 52%).

$^1$H NMR (200 MHz, CDCl$_3$): δ 7.60 (d, 2H, J=8.90 Hz), 7.13 (d, 2H, J=8.90 Hz), 7.01 (dd, 1H, J=14.80 Hz), 6.09~6.32 (m, 4H), 5.78 (s, 1H), 2.59 (s, 3H), 2.43 (s, 3H), 2.01 (br s, 5H), 1.72 (s, 3H), 1.56~1.68 (m, 2H), 1.44~1.49 (m, 2H), 1.03 (s, 6H).

$^{13}$C NMR (100 MHz, CDCl$_3$): δ 191.03, 158.98, 151.30, 145.86, 139.56, 137.68, 137.21, 136.71, 135.98, 135.07, 130.76, 130.00, 129.43, 128.67, 121.39, 120.62, 39.55, 34.24, 33.08, 29.68, 28.94, 26.82, 21.74, 19.18, 13.73, 12.91.

MS: m/z(%)=69(100), 109(92), 149 (95), 201(25), 255 (128), 391(28), 461(16, M$^+$).

Example 43

4-[(2E,4E,6E,8E)-3,7-dimethyl-9-(2,6,6-trimethyl-1-cyclohexenyl)-2,4,6,8-nonatetraenoyl]aminophenyl-2-oxobutanoate (KCBG47)

To a solution of 2-ketobutyric acid (0.025 g, 0.24 mmol) in anhydrous CH$_2$Cl$_2$ (5 mL) was added EDCI (0.046 g, 0.24 mmol) in anhydrous CH$_2$Cl$_2$ (2 mL) and stirred for 0.5 h at room temperature. To the reaction mixture were added a solution of HPR (0.047 g, 0.12 mmol) in anhydrous CH$_2$Cl$_2$ (2 mL) and DMAP (cat.). After stirring for 1 h at room temperature and heated to 30° C. for 3 h, the reaction was extracted with EtOAc (30 mL), washed with H$_2$O (2×30 mL), dried over Na$_2$SO$_4$, and evaporated. The crude compound was purified by column chromatography over silica gel (EtOAc:hexane=1:4) to give 4-[(2E,4E,6E,8E)-3,7-dimethyl-9-(2,6,6-trimethyl-1-cyclohexenyl)-2,4,6,8-nonatetraenoyl]aminophenyl-2-oxobutanoate (KCBG47, 0.028 g, 50%).

$^1$H NMR (200 MHz, CDCl$_3$): δ 7.60 (d, 2H, J=8.90 Hz), 7.13 (d, 2H, J=8.90 Hz), 7.01 (dd, 1H, J=14.8 Hz), 6.09~6.32 (m, 4H), 5.78 (s, 1H), 2.98 (q, 2H, J=7.2 Hz), 2.42 (s, 3H), 2.01 (br s, 5H), 1.72 (s, 3H), 1.56~1.68 (m, 2H), 1.44~1.49 (m, 2H), 1.20 (t, 3H, J=7.20 Hz), 1.03 (s, 6H).

$^{13}$C NMR (100 MHz, CDCl$_3$): δ 194.14, 159.32, 151.30, 139.55, 137.67, 137.21, 136.66, 135.06, 130.75, 129.99, 129.43, 128.66, 125.45, 121.46, 120.58, 39.55, 34.24, 33.08, 33.02, 28.93, 21.74, 19.87, 13.72, 12.90, 11.17.

MS: m/z(%)=69(93), 109(100), 119 (65), 161(69), 202 (42), 255(28), 391(55), 475(18, M$^+$).

Example 44

4-(4-[(2E,4E,6E,8E)-3,7-dimethyl-9-(2,6,6-trimethyl-1-cyclohexenyl)-2,4,6,8-nonatetraenoyl]aminophenoxy)-4-oxobutanoic acid (KCBG32)

To a solution of N,N-dimethyl glysine (sarcosine, 0.025 g, 0.24 mmol) in anhydrous CH$_2$Cl$_2$ (5 mL) was added EDCI (0.046 g, 0.24 mmol) in anhydrous CH$_2$Cl$_2$ (2 mL) and stirred for 0.5 h at room temperature. To the reaction mixture were added a solution of HPR (0.047 g, 0.12 mmol) in anhydrous CH$_2$Cl$_2$ (2 mL) and DMAP (cat.). After stirring for 1 h at room temperature and heated to 30° C. for 3 h, the reaction was extracted with EtOAc (30 mL), washed with H$_2$O (2×30 mL), dried over Na$_2$SO$_4$, and evaporated. The crude compound was purified by column chromatography over silica gel (EtOAc:hexane=2:1) to give 4-(4-[(2E,4E,6E,8E)-3,7-dimethyl-9-(2,6,6-trimethyl-1-cyclohexenyl)-2,4,6,8-nonatetraenoyl]aminophenoxy)-4-oxobutanoic acid (KCBG32, 0.043 g, 75%).

$^1$H NMR (200 MHz, CDCl$_3$): δ 7.55 (d, 2H, J=8.70 Hz), 7.05 (d, 2H, J=8.70 Hz), 7.01 (dd, 1H, J=14.80 Hz), 6.09~6.31 (m, 4H), 5.78 (s, 1H), 2.44 (s, 6H), 2.42 (s, 3H), 2.01 (br s, 5H), 1.72 (s, 3H), 1.56~1.68 (m, 2H), 1.44~1.49 (m, 2H), 1.03 (s, 6H).

$^{13}$C NMR (100 MHz, CDCl$_3$): δ 169.31, 150.78, 146.16, 139.29, 137.65, 137.23, 136.10, 135.22, 130.46, 130.13, 129.89, 129.47, 128.49, 122.14, 121.76, 121.09, 120.63, 115.74, 60.19, 45.20, 39.52, 34.20, 33.05, 29.65, 28.91, 21.73, 19.71, 13.66, 12.87.

MS: m/z(%)=58(100), 69(6), 149(8), 476(73, M$^+$).

Example 45

4-[(2E,4E,6E,8E)-3,7-dimethyl-9-(2,6,6-trimethyl-1-cyclohexenyl)-2,4,6,8-nonatetraenoyl]aminophenyl-3-hydroxybutanoate (KCBG37)

To a solution of 3-hydroxy butyric acid (0.023 mL, 0.24 mmol) in anhydrous CH$_2$Cl$_2$ (5 mL) was added EDCI (0.046 g, 0.24 mmol) in anhydrous CH$_2$Cl$_2$ (2 mL) and stirred for 0.5 h at room temperature. To a solution of reaction mixture were added HPR (0.047 g, 0.12 mmol) in anhydrous CH$_2$Cl$_2$ (2 mL) and DMAP (cat.). After stirring for 1 h at room temperature and heated to 30° C. for 3 h, the reaction was extracted with EtOAc (30 mL), washed with H$_2$O (2×30 mL), dried over Na$_2$SO$_4$, and evaporated. The crude compound was purified by column chromatography over silica gel (EtOAc:hexane=1:1) to give 4-[(2E,4E,6E,8E)-3,7-dimethyl-9-(2,6,6-trimethyl-1-cyclohexenyl)-2,4,6,8-nonatetraenoyl]aminophenyl-3-hydroxybutanoate (KCBG37, 0.035 g, 62%).

$^1$H NMR (200 MHz, CDCl$_3$): δ 7.56 (d, 2H, J=8.70 Hz), 7.25 (br s, 1H), 6.93~7.06 (m, 3H), 6.09~6.32 (m, 4H), 5.78 (s, 1H), 4.31~4.40 (m, 1H), 2.68~2.81 (m, 2H), 2.43 (s, 3H), 2.01 (br s, 5H), 1.72 (s, 3H), 1.56~1.68 (m, 2H), 1.44~1.49 (m, 3H), 1.20~1.38 (m, 2H), 1.03 (s, 6H).

$^{13}$C NMR (100 MHz, CDCl$_3$): δ 171.20, 148.29, 138.39, 137.20, 136.80, 136.63, 135.27, 129.34, 129.17, 127.81, 121.86, 121.23, 121.08, 120.65, 120.58, 119.91, 63.67, 43.23, 33.76, 32.59, 28.50, 22.62, 22.56, 21.29, 19.18, 18.72, 13.15, 12.43.

MS: m/z(%)=58(100), 69(77), 109(77), 119 (64), 161 (56), 201(33), 255(32), 391(23), 477(28, M$^+$).

Example 46

4-[(2E,4E,6E,8E)-3,7-dimethyl-9-(2,6,6-trimethyl-1-cyclohexenyl)-2,4,6,8-nonatetraenoyl]aminophenyl-1-propanesulfonate (KCBG44)

To the solution of HPR (0.10 g, 0.25 mmol) in anhydrous $CH_2Cl_2$ (10 mL) was added NMM (0.033 mL, 0.31 mmol). To a solution of resulting mixture was added dropwise 1-propane sulfonyl chloride (0.034 mL, 0.31 mmol) in anhydrous $CH_2Cl_2$ (5 mL) at 0° C., and stirred for 2 h at room temperature. The reaction mixture was washed with $H_2O$ (2×30 mL). The organic layer was dried over $MgSO_4$ and evaporated in vacuo. The residue was purified by column chromatography over silica gel (EtOAc:hexane=1:3) to give 4-[(2E,4E,6E,8E)-3,7-dimethyl-9-(2,6,6-trimethyl-1-cyclohexenyl)-2,4,6,8-nonatetraenoyl]aminophenyl-1-propanesulfonate (KCBG44, 0.095 g, 75%).

$^1$H NMR (200 MHz, $CDCl_3$): δ 7.59 (d, 2H, J=8.90 Hz), 7.18~7.27 (m, 3H), 7.01 (dd, 1H, J=14.80 Hz), 6.09~6.31 (m, 4H), 5.78 (s, 1H), 3.22 (d, 2H, J=7.80 Hz), 2.41 (s, 3H), 1.95~2.06 (m, 7H), 1.72 (s, 3H), 1.56~1.68 (m, 2H), 1.44~1.49 (m, 2H), 1.10 (t, 3H, J=7.30 Hz), 1.03 (s, 6H).

$^{13}$C NMR (100 MHz, $CDCl_3$): δ 165.30, 151.24, 144.66, 139.52, 137.64, 137.41, 137.17, 135.07, 130.72, 129.97, 129.41, 128.64, 122.47, 120.90, 120.77, 51.82, 39.54, 34.21, 33.09, 28.91, 21.70, 19.16, 17.26, 13.72, 12.87, 12.81.

MS: m/z(%)=69(14), 108(100), 123 (12), 215(13), 267 (6), 497(50, M$^+$).

Example 47

4-[(2E,4E,6E,8E)-3,7-dimethyl-9-(2,6,6-trimethyl-1-cyclohexenyl)-2,4,6,8-nonatetraenoyl]aminophenyl-1-butanesulfonate (KCBG43)

To a solution of HPR (0.10 g, 0.25 mmol) in anhydrous $CH_2Cl_2$ (10 mL) was added NMM (N-methyl morpholine, 0.033 mL, 0.31 mmol). To the resulting mixture was added dropwise 1-butane sulfonyl chloride (0.039 mL, 0.31 mmol) in anhydrous $CH_2Cl_2$ (5 mL) at 0° C., and stirred for 2 h at room temperature. The reaction mixture was washed with $H_2O$ (2×30 mL). The organic layer was dried over $MgSO_4$ and evaporated in vacuo. The residue was purified by column chromatography over silica gel (EtOAc:hexane=1:3) to give 4-[(2E,4E,6E,8E)-3,7-dimethyl-9-(2,6,6-trimethyl-1-cyclohexenyl)-2,4,6,8-nonatetraenoyl]aminophenyl-1-butanesulfonate (KCBG43, 0.095 g, 73%).

$^1$H NMR (200 MHz, $CDCl_3$): δ 7.57 (d, 2H, J=8.90 Hz), 7.53 (br s, 1H), 7.18 (d, 2H, J=8.90 Hz), 7.01 (dd, 1H, J=14.80 Hz), 6.09~6.31 (m, 4H), 5.80 (s, 1H), 3.22 (d, 2H, J=7.80 Hz), 2.41 (s, 3H), 1.87~2.01 (m, 7H), 1.72 (s, 3H), 1.56~1.68 (m, 2H), 1.44~1.49 (m, 4H), 1.01 (s, 6H), 0.97 (t, 3H, J=7.30 Hz).

$^{13}$C NMR (100 MHz, $CDCl_3$): δ 165.23, 151.38, 144.71, 139.58, 137.66, 137.37, 137.19, 135.05, 130.80, 130.00, 129.41, 128.69, 122.52, 120.86, 120.70, 49.95, 39.54, 34.23, 33.07, 28.92, 25.36, 21.73, 21.39, 19.17, 13.73, 13.45, 12.89.

MS: m/z(%)=69(16), 108(100), 136(12), 204(10), 229(7), 511(70 M$^+$).

Example 48

4-[(2E,4E,6E,8E)-3,7-dimethyl-9-(2,6,6-trimethyl-1-cyclohexenyl)-2,4,6,8-nonatetraenoyl]aminophenyl propyl hydrogen phosphate (KCBG48)

To a solution of propanol (0.8 mL, 10.0 mmol) in anhydrous $CH_2Cl_2$ (10 mL) was added $POCl_3$ (3.0 mL, 32.0 mmol) dropwise at 0° C. After stirring at 0° C. for 1 h, the mixture was refluxed for 5 h and then followed by vacuum distillation (bp 38~42° C./0.2 torr) to afford propyl dichlorophosphate.

To a cooled solution of propyl dichlorophosphate (1 eq.) in anhydrous $CH_2Cl_2$ (5 mL) were added HPR (0.1 g, 0.33 mmol) in anhydrous $CH_2Cl_2$ (5 mL) and TEA (0.11 mL, 0.83 mmol). After stirring for 1 h, $H_2O$ (2 mL) was added. The mixture stirred for 2 h at room temperature, and quenched with $NH_4Cl$ (aq. 20 mL). The aqueous layer was extracted with $CH_2Cl_2$ (2×10 mL), and the combined organic layers were washed with $H_2O$ (20 mL), dried over $Na_2SO_4$, and concentrated. The residue was purified by column chromatography over silica gel (EtOAc:hexane=1:3) to afford 4-[(2E,4E,6E,8E)-3,7-dimethyl-9-(2,6,6-trimethyl-1-cyclohexenyl)-2,4,6,8-nonatetraenoyl]aminophenyl propyl H phosphate (0.12 g, 73%) as a yellow solid.

$^1$H NMR (400 MHz, $CDCl_3$): δ 7.56 (d, 2H, J=7.80 Hz), 7.39 (br s, 1H), 7.15 (d, 2H, J=8.70 Hz), 7.01 (dd, 1H, J=14.80 Hz), 6.12~6.30 (m, 4H), 5.79 (s, 1H), 4.28 (m, 2H), 2.41 (s, 3H), 2.02 (br s, 5H), 1.79~1.83 (m, 2H), 1.72 (s, 3H), 1.60~1.63 (m, 2H), 1.45~1.48 (m, 2H), 1.02 (s, 6H), 0.96~1.00 (m, 3H).

$^{13}$C NMR (100 MHz, $CDCl_3$): δ 166.19, 151.73, 145.59, 139.51, 137.69, 137.22, 136.89, 135.13, 130.70, 129.99, 129.44, 128.65, 121.12, 120.85, 120.80, 72.15, 72.08, 39.58, 34.24, 33.09, 28.94, 23.29, 21.74, 19.20, 13.72, 12.91.

MS: m/z(%)=58(34), 108(100), 119 (41), 159(71), 202 (25), 225(18), 391(38), 513(66, M$^+$).

Example 49

Butyl-(4-[(2E,4E,6E,8E)-3,7-dimethyl-9-(2,6,6-trimethyl-1-cyclohexenyl)-2,4,6,8-nonatetraenoyl]aminophenyl) hydrogen phosphate (KCBG49)

To a solution of butanol (0.98 mL, 10.0 mmol) in anhydrous $CH_2Cl_2$ (10 mL) was added dropwise $POCl_3$ (3.0 mL, 32.0 mmol) at 0° C. After stirring at 0° C. for 1 h, the mixture was refluxed for 5 h and then followed by vacuum distillation to afford butyl dichlorophosphate.

To a cooled solution of butyl dichlorophosphate (1 eq.) in anhydrous $CH_2Cl_2$ (5 mL) were added HPR (0.1 g, 0.33 mmol) in anhydrous $CH_2Cl_2$ (5 mL) and TEA (0.11 mL, 0.83 mmol). After stirring for 1 h, $H_2O$ (2 mL) was added. The mixture stirred for 2 h at room temperature, and quenched with $NH_4Cl$ (aq. 20 mL). The aqueous layer was extracted with $CH_2Cl_2$ (2×10 mL), and the combined organic layers were washed with $H_2O$ (20 mL), dried over $Na_2SO_4$, and concentrated. The residue was purified by column chromatography over silica gel (EtOAc:hexane=1:3) to afford butyl-(4-[(2E,4E,6E,8E)-3,7-dimethyl-9-(2,6,6-trimethyl-1-cyclohexenyl)-2,4,6,8-nonatetraenoyl]aminophenyl) hydrogen phosphate (KCBG49, 0.12 g, 71%) as a yellow solid.

$^1$H NMR (400 MHz, $CDCl_3$): δ 7.89 (br s, 1H), 7.55 (d, 2H, J=7.80 Hz), 7.15 (d, 2H, J=8.70 Hz), 6.99 (dd, 1H, J=14.80 Hz), 6.12~6.29 (m, 4H), 5.84 (s, 1H), 4.32 (m, 2H), 2.41 (s, 3H), 2.02 (br s, 5H), 1.74~1.81 (m, 2H), 1.72 (s, 3H), 1.60~1.63 (m, 2H), 1.41~1.48 (m, 4H), 1.03 (s, 6H), 0.97 (t, 3H, J=7.30 Hz).

$^{13}$C NMR (100 MHz, CDCl$_3$): δ 165.29, 150.83, 144.89, 139.29, 137.66, 137.21, 136.69, 135.30, 130.43, 129.92, 129.48, 128.57, 120.99, 120.69, 120.64, 70.52, 70.44, 39.54, 34.22, 33.06, 31.74, 31.67, 28.91, 21.71, 19.17, 18.53, 13.67, 13.43, 12.87.

MS: m/z(%)=69(46), 108(83), 119(30), 201(20), 255(15), 391(14), 527(42, M$^+$).

Example 50

4-(4-[(2E,4E,6E,8E)-3,7-dimethyl-9-(2,6,6-trimethyl-1-cyclohexenyl)-2,4,6,8-nonatetraenoyl]aminophenoxy)-4-oxobutanoic acid (KCBG50)

To a solution of succinic acid (0.028 g, 0.24 mmol) in anhydrous CH$_2$Cl$_2$ (5 mL) was added EDCI (0.046 g, 0.24 mmol) in anhydrous CH$_2$Cl$_2$ (2 mL) and stirred for 0.5 h at room temperature. To a solution of reaction mixture were added HPR (0.047 g, 0.12 mmol) in anhydrous CH$_2$Cl$_2$ (5 mL) and DMAP (cat.). After stirring for 1 h at room temperature and heating to 30° C. for 3 h, the reaction was extracted with EtOAc (30 mL), washed with H$_2$O (2×30 mL), dried over Na$_2$SO$_4$, and evaporated. The crude compound was purified by column chromatography over silica gel (EtOAc:hexane=2:1) to give 4-(4-[(2E,4E,6E,8E)-3,7-dimethyl-9-(2,6,6-trimethyl-1-cyclohexenyl)-2,4,6,8-nonatetraenoyl]aminophenoxy)-4-oxobutanoic acid (KCBG50, 0.042 g, 72%).

$^1$H NMR (200 MHz, CDCl$_3$): δ 7.40~7.50 (br s, 2H), 6.99~7.04 (m, 3H), 6.09~6.30 (m, 4H), 5.79 (s, 1H), 4.40~4.55 (br s, 1H), 2.82~2.84 (m, 4H), 2.40 (s, 3H), 2.00 (br s, 5H), 1.72 (s, 3H), 1.56~1.68 (m, 2H), 1.44~1.49 (m, 2H), 1.03 (s, 6H).

$^{13}$C NMR (100 MHz, CDCl$_3$): δ 174.52, 171.23, 159.32, 146.16, 139.55, 137.60, 137.19, 135.57, 130.75, 129.80, 129.53, 128.21, 121.65, 120.36, 39.89, 34.14, 33.01, 29.32, 29.06, 28.97, 28.87, 21.67, 19.12, 13.55, 12.81.

MS: m/z(%)=58(100), 69(22), 105(9), 135 (8), 161(8), 391(7), 491(35, M$^+$).

Example 51

4-(4-[(2E,4E,6E,8E)-3,7-dimethyl-9-(2,6,6-trimethyl-1-cyclohexenyl)-2,4,6,8-nonatetraenoyl]aminophenoxy)-oxo-hexanedioic acid (KCBG51)

To a solution of adipic acid (0.071 g, 0.48 mmol) in anhydrous CH$_2$Cl$_2$ (10 mL) was added EDCI (0.092 g, 0.48 mmol) in anhydrous CH$_2$Cl$_2$ (2 mL) and stirred for 0.5 h at room temperature. To a solution of reaction mixture were added HPR (0.094 g, 0.24 mmol) in anhydrous CH$_2$Cl$_2$ (10 mL) and DMAP (cat.). After stirring for 1 h at room temperature and heating to 30° C. for 4 h, the reaction was extracted with EtOAc (50 mL), washed with H$_2$O (2×50 mL), dried over Na$_2$SO$_4$, and evaporated. The crude compound was purified by column chromatography over silica gel (EtOAc:hexane=2:1) to give 4-(4-[(2E,4E,6E,8E)-3,7-dimethyl-9-(2,6,6-trimethyl-1-cyclohexenyl)-2,4,6,8-nonatetraenoyl]aminophenoxy)-oxo-hexanedioic acid (KCBG51, 0.062 g, 51%).

$^1$H NMR (200 MHz, CDCl$_3$+CD$_3$OD): δ 7.57~7.61 (m, 2H), 6.99~7.04 (m, 3H), 6.09~6.30 (m, 4H), 5.88 (s, 1H), 2.40~2.58 (m, 2H), 2.40 (s, 3H), 2.33~2.40 (m, 2H), 2.00 (br s, 5H), 1.72 (s, 3H), 1.56~1.78 (m, 4H), 1.44~1.49 (m, 2H), 1.03 (s, 6H).

$^{13}$C NMR (100 MHz, CDCl$_3$): δ 175.60, 172.04, 146.39, 139.09, 137.70, 137.28, 136.42, 135.53, 130.16, 129.89, 129.57, 128.41, 121.80, 120.48, 34.25, 34.01, 33.68, 33.08, 28.95, 24.37, 24.31, 21.75, 21.06, 19.20, 14.19, 13.66, 12.90.

Example 52

4-[(2E,4E,6E,8E)-3,7-dimethyl-9-(2,6,6-trimethylcyclohex-1-enyl)-nona-2,4,6,8-tetraenoylamino]phenyl-2-acetylamino-4-carbamoylbutanoate (KCBG52)

To a solution of N-acetyl glutamine (0.090 g, 0.48 mmol) in anhydrous DMF (5 mL) was added EDCI (0.092 g, 0.48 mmol) in anhydrous CH$_2$Cl$_2$ (2 mL) and stirred for 0.5 h at room temperature. To a solution of reaction mixture were added HPR (0.094 g, 0.24 mmol) in anhydrous CH$_2$Cl$_2$ (10 mL) and DMAP (cat.). After stirring for 1 h at room temperature and heating to 30° C. for 4 h, the reaction was extracted with EtOAc (50 mL), washed with H$_2$O (2×50 mL), dried over Na$_2$SO$_4$, and evaporated. The crude compound was purified by column chromatography over silica gel (EtOAc:hexane=2:1) to give 4-[(2E,4E,6E,8E)-3,7-dimethyl-9-(2,6,6-trimethylcyclohex-1-enyl)-nona-2,4,6,8-tetraenoylamino]phenyl-2-acetylamino-4-carbamoylbutanoate (KCBG52, 0.069 g, 48%).

$^1$H NMR (200 MHz, CDCl$_3$+CD$_3$OD): δ 7.86 (br s, 1H), 7.57~7.61 (m, 2H) 6.99~7.04 (m, 3H), 6.09~6.30 (m, 4H), 5.89 (s, 1H), 4.63~4.67 (m, 1H), 2.40 (s, 3H), 2.25~2.40 (m, 4H), 2.04 (s, 3H), 2.01 (br s, 5H), 1.72 (s, 3H), 1.56~1.78 (m, 4H), 1.44~1.49 (m, 2H), 1.03 (s, 6H).

$^{13}$C NMR (100 MHz, CDCl$_3$): δ 174.67, 170.98, 170.78, 170.71, 165.37, 149.85, 145.84, 138.86, 137.50, 137.09, 136.81, 135.41, 129.93, 129.70, 129.40, 128.20, 125.76, 121.72, 121.38, 120.42, 60.19, 52.15, 34.06, 33.60, 32.90, 31.47, 28.77, 27.11, 25.79, 25.70, 22.72, 21.57, 20.87, 19.02, 14.00, 13.48, 12.71.

Example 53

4-(4-[(2E,4E,6E,8E)-3,7-dimethyl-9-(2,6,6-trimethyl-1-cyclohexenyl)-2,4,6,8-nonatetraenoyl]aminophenoxy)-oxo-heptanedioic acid (KCBG53)

To a solution of pimelic acid (0.076 g, 0.48 mmol) in anhydrous CH$_2$Cl$_2$ (10 mL) was added EDCI (0.092 g, 0.48 mmol) in anhydrous CH$_2$Cl$_2$ (10 mL) and stirred for 0.5 h at room temperature. To a solution of reaction mixture were added HPR (0.094 g, 0.24 mmol) in anhydrous CH$_2$Cl$_2$ (10 mL) and DMAP (cat.). After stirring for 1 h at room temperature and heating to 30° C. for 4 h, the reaction was extracted with EtOAc (50 mL), washed with H$_2$O (2×50 mL), dried over Na$_2$SO$_4$, and evaporated. The crude compound was purified by column chromatography over silica gel (EtOAc:hexane=2:1) to 4-(4-[(2E,4E,6E,8E)-3,7-dimethyl-9-(2,6,6-trimethyl-1-cyclohexenyl)-2,4,6,8-nonatetraenoyl]aminophenoxy)-oxo-heptanedioic acid (KCBG53, 0.069 g, 54%).

$^1$H NMR (200 MHz, CDCl$_3$+CD$_3$OD): δ 7.50~7.57 (m, 2H), 6.92~7.03 (m, 3H), 6.09~6.30 (m, 4H), 5.77 (s, 1H), 2.56 (t, 2H, J=7.44), 2.42 (s, 3H), 2.35~2.41 (m, 2H), 2.00 (br s, 5H), 1.72 (s, 3H), 1.56~1.77 (m, 6H), 1.44~1.49 (m, 4H), 1.03 (s, 6H).

$^{13}$C NMR (100 MHz, CDCl$_3$): δ 175.87, 172.25, 150.12, 139.06, 137.70, 137.27, 135.54, 130.13, 129.88, 129.57, 128.39, 121.79, 120.48, 34.10, 33.88, 33.08, 28.95, 28.54, 24.59, 24.53, 21.75, 19.20, 13.65, 12.90.

Example 54

4-(4-[(2E,4E,6E,8E)-3,7-dimethyl-9-(2,6,6-trimethyl-1-cyclohexenyl)-2,4,6,8-nonatetraenoyl]aminophenoxy)-oxo-octanedionic acid (KCBG54)

To a solution of suberic acid (0.083 g, 0.48 mmol) in anhydrous $CH_2Cl_2$ (10 mL) was added EDCI (0.092 g, 0.48 mmol) in anhydrous $CH_2Cl_2$ (10 mL) and stirred for 0.5 h at room temperature. To a solution of reaction mixture were added HPR (0.094 g, 0.24 mmol) in anhydrous $CH_2Cl_2$ (10 mL) and DMAP (cat.). 0.5 h at room temperature were added HPR (0.094 g, 0.24 mmol) in anhydrous $CH_2Cl_2$ (10 mL) and DMAP (cat.). After stirring for 1 h at room temperature and heating to 30° C. for 4 h, the reaction was extracted with EtOAc (50 mL), washed with $H_2O$ (2×50 mL), dried over $Na_2SO_4$, and evaporated. The crude compound was purified by column chromatography over silica gel (EtOAc:hexane=2:1) to give 4-(4-[(2E,4E,6E,8E)-3,7-dimethyl-9-(2,6,6-trimethyl-1-cyclohexenyl)-2,4,6,8-nonatetraenoyl]aminophenoxy)-oxo-octanedionic acid (KCBG54, 0.072 g, 55%).

$^1$H NMR (200 MHz, $CDCl_3$+$CD_3OD$): δ 7.56~7.61 (m, 2H), 6.98~7.03 (m, 3H), 6.09~6.30 (m, 4H), 5.88 (s, 1H), 2.54 (t, 2H, J=7.38), 2.42 (s, 3H), 2.31 (t, 2H, J=7.40), 2.00 (br s, 5H), 1.72 (s, 3H), 1.56~1.77 (m, 8H), 1.44~1.49 (m, 8H), 1.03 (s, 6H).

$^{13}$C NMR (100 MHz, $CDCl_3$): δ 176.03, 172.35, 150.21, 139.09, 137.70, 137.28, 135.51, 130.17, 129.89, 129.57, 128.41, 121.80, 120.49, 34.25, 34.00, 33.09, 28, 28.75, 24.71, 21.75, 19.20, 13.66, 12.90.

Example 55

[(2E,4E,6E,8E)-3,7-dimethyl-9-(2,6,6-trimethyl-1-cyclohexenyl)-2,4,6,8-nonatetraenoyl]-(4-butylphenyl)amide (KCBG055)

To a solution of retinoic acid (0.050 g, 0.16 mmol) in anhydrous $CH_2Cl_2$ (5 mL) was added EDCI (0.038 g, 0.19 mmol) in anhydrous $CH_2Cl_2$ (2 mL) and stirred for 0.5 h at room temperature. To a solution of reaction mixture were added 4-butyl aniline (0.026 mL, 0.16 mmol) in anhydrous $CH_2Cl_2$ (5 mL) and DMAP (cat.). After stirring for 2 h at room temperature, the reaction was extracted with EtOAc (30 mL), washed with $H_2O$ (2×30 mL), dried over $Na_2SO_4$, and evaporated. The crude compound was purified by column chromatography over silica gel (EtOAc:hexane=1:5) to give [(2E,4E,6E,8E)-3,7-dimethyl-9-(2,6,6-trimethyl-1-cyclohexenyl)-2,4,6,8-nonatetraenoyl]-(4-butylphenyl)amide (KCBG055, 0.039 g, 55%).

$^1$H-NMR (200 MHz, $CDCl_3$): δ 7.47 (d, 2H, J=8.90), 7.09~7.15 (m, 3H), 7.05 (dd, 1H, J=14.90), 6.10~6.35 (m, 4H), 5.79 (s, 1H), 2.56 (t, 2H, J=7.80), 2.41 (s, 3H), 2.01 (br s, 5H),1.72 (s 3H), 1.45~1.68 (m, 6H), 1.25~1.42 (m, 2H), 1.02 (s, 6H), 0.87~0.99 (m, 3H).

$^{13}$C NMR (100 MHz, $CDCl_3$): δ 164.55, 148.04, 138.14, 137.25, 137.17, 136.97, 136.00, 130.10, 129.68, 129.33, 128.34, 127.42, 122.77, 118.98, 34.23, 33.83, 33.20, 32.58, 28.78, 21.67, 21.50, 18.70, 13.75, 13.22, 12.56.

Example 56

[(2E,4E,6E,8E)-3,7-dimethyl-9-(2,6,6-trimethyl-1-cyclohexenyl)-2,4,6,8-nonatetraenoyl]-(4-butoxyphenyl)amide (KCBG056)

To a solution of retinoic acid (0.050 g, 0.16 mmol) in anhydrous $CH_2Cl_2$ (5 mL) was added EDCI (0.038 g, 0.19 mmol) in anhydrous $CH_2Cl_2$ (2 mL) and stirred for 0.5 h at room temperature. To a solution of reaction mixture were added 4-butoxy aniline (0.027 mL, 0.16 mmol) in anhydrous $CH_2Cl_2$ (5 mL) and DMAP (cat.). After stirring for 2 h at room temperature, the reaction was extracted with EtOAc (30 mL), washed with (2×30 mL), dried over $Na_2SO_4$, and evaporated. The crude compound was purified by column chromatography over silica gel (EtOAc:hexane=1:6) to give [(2E,4E,6E,8E)-3,7-dimethyl-9-(2,6,6-trimethyl-1-cyclohexenyl)-2,4,6,8-nonatetraenoyl]-(4-butoxyphenyl)amide (KCBG56, 0.048 g, 65%).

$^1$H-NMR (200 MHz, $CDCl_3$): δ 7.45 (d, 2H, J=8.90), 7.26 (br s, 1H), 7.05 (dd, 1H, J=14.90), 6.84 (d, 2H, J=8.80), 6.10~6.30 (m, 4H), 5.79 (s, 1H), 3.93 (t, 2H, J=7.38), 2.41 (s, 3H), 2.01 (br s, 5H), 1.72 (s 3H), 1.58~1.74 (m, 4H), 1.42~1.53 (m, 4H), 1.02 (s, 6H), 0.92~0.96 (m, 3H).

$^{13}$C NMR (100 MHz, $CDCl_3$): δ 164.29, 154.47, 147.74, 138.05, 137.25, 136.97, 136.05, 132.58, 130.11, 129.55, 129.32, 127.38, 122.83, 120.40, 114.35, 67.18, 33.83, 32.58, 30.79, 28.78, 21.50, 18.73, 13.69, 13.20, 12.56.

Example 57

4-(4-[(2E,4E,6E,8E)-3,7-dimethyl-9-(2,6,6-trimethyl-1-cyclohexenyl)-2,4,6,8-nonatetraenoyl]aminophenyl-butanoate (KCBG60)

Phenyl butylate (0.47 mL, 5.11 mmol), dicyclohexylcarbodiimide (1.58 g, 7.66 mmole) and dichloromethane (50 mL) were placed in a reactor and stirred for 30 min in an ice bath. To the resulting solution was added 4-HPR (1.00 g, 2.55 mmol) and then 4-(dimethylamino) pyridine (0.31 g, 2.55 mmol) and stirred for 1.5 h at room temperature.

The mixture was concentrated under reduced pressure to remove the solvent. The residue was added to ethyl acetate. The resulting solution was filtered to remove DCC and DCC-urea and washed with water (2×100 mL) and then brine (100 mL). The organic layer was concentrated over magnesium sulfate in vacuum to remove the solvent. The crude product was purified by column chromatography with EtOAc:dichloromethane:hexane (1:1:6) to give 4-(4-[(2E, 4E,6E,8E)-3,7-dimethyl-9-(2,6,6-trimethyl-1-cyclohexenyl)-2,4,6,8-nonatetraenoyl]aminophenyl-butanoate (KCBG60, 72%) as a yellow solid.

m.p.=146~148° C., U.V.=λmax(ε): 369

$^1$H-NMR (400 MHz, $CDCl_3$): δ 7.56 (d, 2H, J=7.8, 15, 18-ArH), 7.19 (s, 1H, 14-NH), 7.04 (d, 2H, J=8.8, 16, 17-ArH), 7.00 (dd, 1H, J=15.1 and 11.7, 10-CH), 6.30 (s, 1H, 6-CH), 6.26 (s, 1H, 11-CH), 6.16 (s, 1H, 9-CH), 6.13 (d, 1H, J=4.9, 7-CH), 5.78 (s, 1H, 13-CH), 2.53 (t, 2H, J=7.3, 19-$CH_2$), 2.42 (s, 3H, 12-$CH_3$), 2.03 (t, 2H, J=5.9, 4-$CH_2$), 2.01 (s, 3H, 8-$C_3$), 1.78 (sext, 2H, J=7.3, 20-$CH_3$), 1.72 (s, 3H, 5-$CH_3$), 1.62 (m, 2H, 3-$CH_2$), 1.47 (m, 2H, 2-$CH_2$), 1.04 (t, 3H, J=7.3, 21-$CH_3$), 1.03 (s, 6H, 1-$CH_3$).

$^{13}$C NMR (100 MHz, $CDCl_3$): δ 172.21, 165.01, 150.48, 146.53, 139.12, 137.60, 137.14, 135.85, 135.16, 130.30, 129.77, 129.39, 128.39, 121.77, 121.07, 120.61, 39.69, 36.26, 34.33, 33.18, 29.03, 21.83, 21.79, 19.33, 18.54, 13.85, 13.79, 13.74, 13.02, 12.96.

Example 58

4-(4-[(2E,4E,6E,8E)-3,7-dimethyl-9-(2,6,6-trimethyl-1-cyclohexenyl)-2,4,6,8-nonatetraenoyl]aminophenoxy)-4-oxobutanoic acid (KCBG50), sodium salt (KCBG57)

To a solution of KCBG50 (0.1 g, 0.20 mmol) in anhydrous EtOAc (10 mL) and acetone (2 mL) was added sodium 2-ethylhexanoic acid (0.04 g, 0.24 mmol) and heated slightly. The resulting mixture was stirred at room temperature until salting out. After stirring for 1 h, the reaction mixture was filtered, washed with EtOAc (20 mL) and dried to give 4-(4-[(2E,4E,6E,8E)-3,7-dimethyl-9-(2,6,6-trimethyl-1-cyclohexenyl)-2,4,6,8-nonatetraenoyl]aminophenoxy)-4-oxobutanoic acid, sodium salt (KCBG57, 0.099 g, 95%).

$^1$H NMR (200 MHz, CD$_3$OD): δ 7.40~7.50 (br s, 2H), 6.99~7.04 (m, 3H), 6.09~6.30 (m, 4H), 5.79 (s, 1H), 4.40~4.55 (br s, 1H), 2.82~2.84 (m, 4H), 2.40 (s, 3H), 2.00 (br s, 5H), 1.72 (s, 3H), 1.56~1.68 (m, 2H), 1.44~1.49 (m, 2H), 1.03 (s, 6H).

$^{13}$C NMR (100 MHz, CD$_3$OD): δ 174.52, 171.23, 159.32, 146.16, 139.55, 137.60, 137.19, 135.57, 130.75, 129.80, 129.53, 128.21, 121.65, 120.36, 39.89, 34.14, 33.01, 29.32, 29.06, 28.97, 28.87, 21.67, 19.12, 13.55, 12.81.

Example 59

4-[(2E,4E,6E,8E)-3,7-dimethyl-9-(2,6,6-trimethylcyclohex-1-enyl)-nona-2,4,6,8-tetraenoylamino]phenyl-2-acetylamino-4-carbamoylbutanoate (KCBG52) hydrochloride (KCBG58)

To a solution of KCBG52 (0.2 g, 0.35 mmol) in anhydrous acetone (3 mL) and MeOH (0.5 mL) was added 2.0M-HCl solution(0.2 mL, in diethyl ether). The resulting mixture was stirred at room temperature until salting out. After adding Et$_2$O (20 mL) and stirring for additional 1 h, the reaction mixture was filtered, washed with Et$_2$O (20 mL) and dried to give 4-[(2E,4E,6E,8E)-3,7-dimethyl-9-(2,6,6-trimethylcyclohex-1-enyl)-nona-2,4,6,8-tetraenoylamino]phenyl-2-acetylamino-4-carbamoylbutanoate hydrochloride (KCBG58, 0.19 g, 92%).

$^1$H NMR (200 MHz, CDCl$_3$+CD$_3$OD): δ 7.86 (br s, 1H), 7.57~7.61 (m, 2H) 6.99~7.04 (m, 3H), 6.09~6.30 (m, 4H), 5.89 (s, 1H), 4.63~4.67 (m, 1H), 2.40 (s, 3H), 2.25~2.40 (m, 4H), 2.04 (s, 3H), 2.01 (br s, 5H), 1.72 (s, 3H), 1.56~1.78 (m, 4H), 1.44~1.49 (m, 2H), 1.03 (s, 6H).

$^{13}$C NMR (100 MHz, CDCl$_3$): δ 174.67, 170.98, 170.78, 170.71, 165.37, 149.85, 145.84, 138.86, 137.50, 137.09, 136.81, 135.41, 129.93, 129.70, 129.40, 128.20, 125.76, 121.72, 121.38, 120.42, 60.19, 52.15, 34.06, 33.60, 32.90, 31.47, 28.77, 27.11, 25.79, 25.70, 22.72, 21.57, 20.87, 19.02, 14.00, 13.48, 12.71.

Experimental Example 1

Effect of Retinoid Derivatives on Proliferation of Various Cancer Cells

The effects of test compounds on proliferation of various cancer cells was examined by 3-(4,5-dimethylthiazol-2-yl)-2,5-diphenyltetrazolium bromide (MTT, Sigma) assay in a dose dependent manner. In the MTT assay, colon, liver, cervix, ovary, and breast cancer cell lines were treated with test compounds at various concentrations. Living cancer cells reduce MTT to dark blue MTT formazan that would be measured by absorbance.

The novel retinoid derivative compounds prepared according to the present invention was used as test compounds, while N-retinyl-4-aminophenol (HPR) and All-trans-retinoic acid (ATRA) were used as control. Colon cancer cells, HCT116, DLD-1 and HT29, cervix cancer cells, HeLa and CaSki, ovary cancer cells, SKOV-3, 2774 and OVCAR-3, liver cancer cells, SK-Hep-1, PLCPRF5 and HepG2, and breast cancer cells, ZR75-1 and MDA-MB 231 were seeded at an initial density of 3000 cells per well in 96-well plates. After attachment of cells to the walls of the wells, the medium containing fresh retinoid was treated with various concentrations (0.5 μM, 1 μM, 2.5 μM, 5 μM, 10 μM) for 48 hours. 50 μl of MTT solution (2 mg/ml in PBS) was added to to cell culture media. The reaction micture was incubated at 37° C. in a 5% CO$_2$ atmosphere for 4 hours. The supernatant was removed and 150 μl of DMSO was added. The optical density was measured spectrophotometrically at 550 nm. FIG. 1 shows the absorbances of cell culture media treated with the retinoid derivatives KCBG 8, 9, 10, 11 or 41 according to the present invention and the control compound HPR. For other retinoid derivatives according to the present invention, absorbances were measured by this procedure and IC$_{50}$ values, concentrations required for 50% growth inhibition, were determined. The results are shown in Table 1 and Table 2 below.

TABLE 1

Activities of various retinoid derivatives in colon cancer cells

| Compound | (IC$_{50}$:μM) |
|---|---|
| ATRA | 20 |
| HPR | 6–8 |
| KCBG08 | >100 |
| KCBG09 | 10–20 |
| KCBG10 | 3 |
| KCBG15 | 8 |
| KCBG22 | 6 |
| KCBG23 | 3.5 |
| KCBG32 | 5 |
| KCBG34 | 3 |
| KCBG35 | 2 |
| KCBG38 | 2 |
| KCBG39 | 3 |
| KCBG40 | 0.6 |
| KCBG41 | 0.3 |
| KCBG42 | 7 |
| KCBG43 | 4 |
| KCBG45 | 7 |
| KCBG47 | 1.8 |
| KCBG50 | 5.5 |
| KCBG51 | 4.5 |
| KCBG52 | 7 |
| KCBG53 | 6.5 |
| KCBG54 | 3.5 |

TABLE 2

Activities of retinoid derivatives KCBG10 and KCBG41, HPR and ATRA in various cancer cells (IC$_{50}$: μM)

| Cancer cells | | ATRA | HPR | KCBG10 | KCBG41 |
|---|---|---|---|---|---|
| Colon cancer | HCT116 | 20 | 6–8 | 3 | 1.4 |
| | DLD-1 | 20 | 9 | 6 | 1.5 |
| | HT29 | 18 | 8 | 6 | 1.2 |
| Uterine cancer | HeLa | 5 | 3 | 0.5 | 3 |
| | CaSki | 20 | 2 | 0.5 | 3 |
| Ovarian cancer | SKOV-3 | >100 | 2 | 0.5 | 3 |
| | 2774 | >100 | 30 | 8 | 2.5 |
| | OVCAR-3 | >100 | 8 | 0.8 | 3.7 |

TABLE 2-continued

Activities of retinoid derivatives KCBG10 and KCBG41, HPR and ATRA in various cancer cells (IC$_{50}$: μM)

| Cancer cells | | ATRA | HPR | KCBG10 | KCBG41 |
| --- | --- | --- | --- | --- | --- |
| Liver cancer | SK-Hep-1 | >500 | >100 | 4.5 | 0.8 |
| | PLCPRF5 | >500 | 20 | 12 | ND |
| | HepG2 | >500 | >100 | >100 | >100 |
| Breast cancer | ZR75-1 | >500 | 15 | 2 | 4.1 |
| | MDA-MB-231 | >100 | 10 | 3.5 | 3.3 |
| | MCF-7 | ND | 7 | 1.3 | 5.5 |

*ND: not determined

As shown in tables, all the retinoid derivatives did not show anti-cancer activity in liver cancer HepG cells. In other cells, ATRA showed very a low anti-cancer activity while HPR, known to have the highest activity at present, had IC$_{50}$ of 3 to 20 μM, KCBG10 have 0.5 to 12 μM and KCBG 41 had 0.8 to 5.5 μM. The derivatives showed differences in their activities between cells. Particularly, it was shown that KCBG10 was more effective on women cancer such as cervix cancer, ovary cancer and breast cancer and KCBG41 was more effective on colon cancer and liver cancer. From these results, it was noted that the retinoid derivatives KCBG10 and KCBG41 have anti-proliferation effects on cancer cells significantly superior to HPR and ATRA but different from cells to cells.

Experimental Example 2

Figure 2:
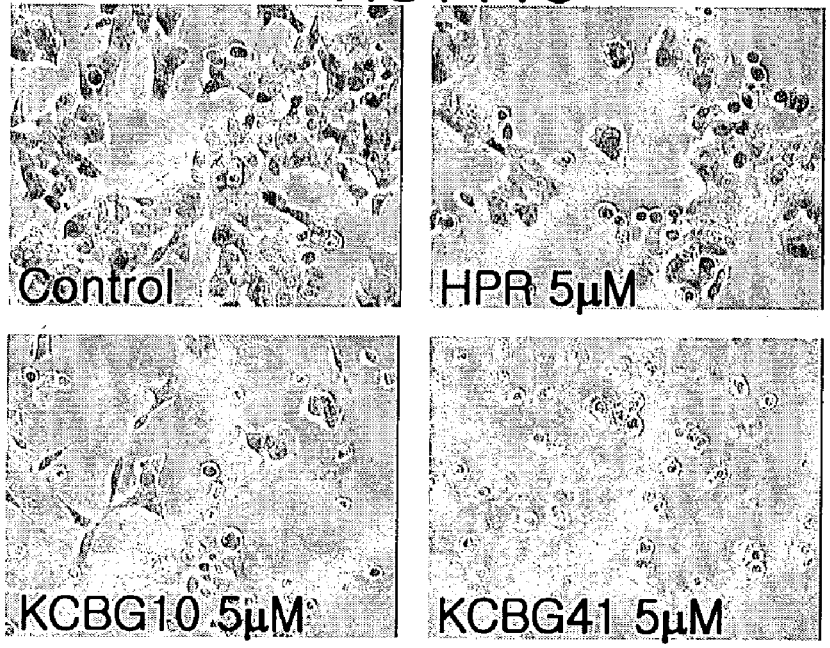
FIG. 2 is the optically microscopic photographs (200×) of colon cancer cells HCT116 and breast cancer cells MCF-7 48 hours after being treated with the respective retinoid derivatives at a concentration of 5 μM. These show the effects of the retinoid derivatives on the morphologies of cancer cells.
Figure 2:
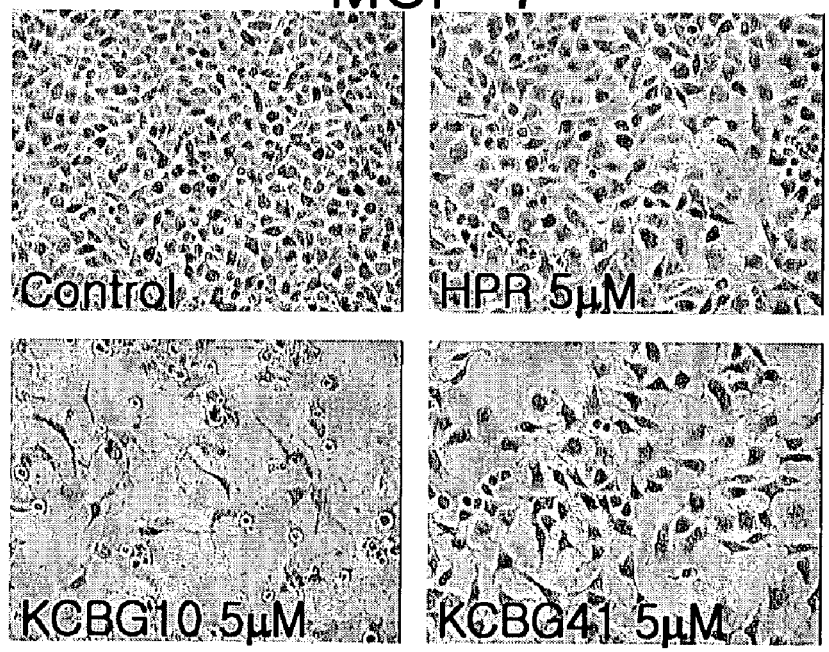

Both colon cancer HCT116 cells and breast cancer MCF-7 cells were treated with 5 μM of the retinoid derivatives KCBG10 and KCBG41 for 48 hours, and photographed by optical microscope (×200). As a control compound, HPR was used at the same concentration. The results are shown in FIG. 2. In FIG. 2, the control represents non-treated cells.

From the results, the cell lines treated with KCBG10 and KCBG41 according to the present invention shows significant reductions in the number of viable cancer cells compared to the conventional anti-cancer compound HPR. Also, judging from morphologies of dying cells it was believed that the reduction of the cell number is attributed to apoptosis. Further, similarly to the results of effects on the proliferation of cancer cells examined in Example 1, KCBG10 kills MCF-7 cells much more than other derivatives at the same concentration and KCBG41 is more effective on HCT116 than other derivatives at the same concentration. These results demonstrate that the compounds of the present invention have more excellent anti-cancer effect than HPR and functions differently according to the kind of cancer cells.

Experimental Example 3

Effects of Retinoid Derivatives Inducing Apoptosis

In order to determine the mechanism by which the retinoid derivatives according to the present invention inhibit the proliferation of cancer cells, changes of cancer cells by test compounds, KCBG10 and KCBG41, including KCBG40 for comparison were examined. As control compounds, DMSO and HPR were used. Colon cancer HCT116 cells in which KCBG 41 is effective and breast cancer MCF-7 cells in which KCBG10 is effective were used for comparison of functional differences.

3-1) Biochemical DNA Fragmentation Assay

Figure 3:
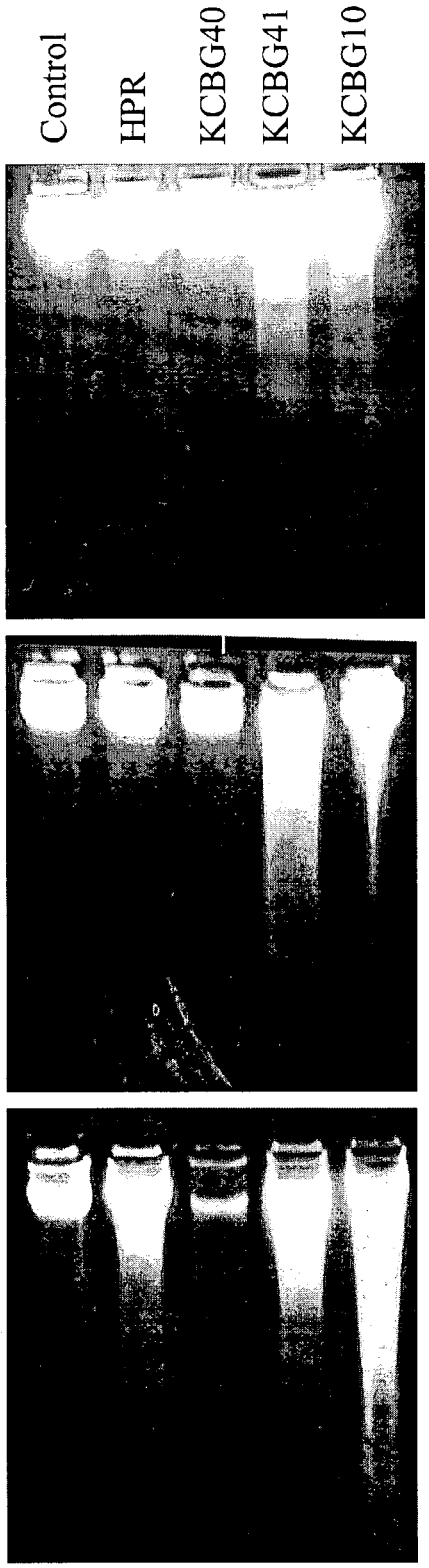
FIG. 3 is the electrophoretic results of chromosomal DNAs derived from colon cancer cells HCT116 and MCF-7 48 hours after being treated with the respective retinoid derivatives at a concentration of 5 μM for induction of apoptosis. The results show that the retinoid derivatives of the present invention resulted in ladder-shaped DNA bands that are due to DNA fragmentation.
Figure 3:
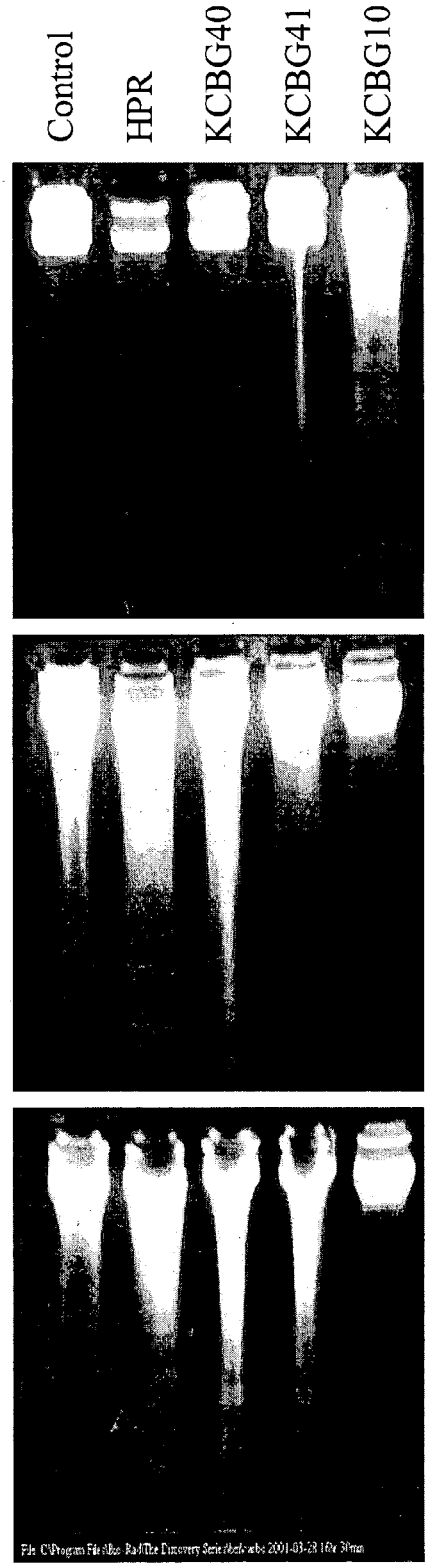

After treated with each retinoid derivative at various concentrations (2.5, 5.0, 10 μM) for 48 hours, HCT116 or MCF-7 cells were poured in 1 mL of PBS and centrifuged at a rate of 13,000 rpm at 4° C. for 1 min. The resulting cell pellets were resuspended in 700 μl of lysis buffer (500 mM Tris, 100 mM EDTA, 0.5% SDS) containing 17.5 μl of proteinase K (20 mg/ml), and incubated on 55° C. water bath for 3 hours. The lysates were mixed with 700 μl of phenol solution while slowly stirring and centrifuged at 12,000 rpm for 5 min. The supernatants were separated and extracted with phenol once more. The supernatants were mixed with 600 μl of 100% ethanol and 60 μl of 3M NaOAc (pH 7.0) and left at −20° C. for 2 hours. The supernatants were removed by centrifugation at 12,000 rpm for 10 min to obtain pellets. After 70% ethanol washing and drying, DNA pellet was resuspended in 100 μl of TE (Tris-EDTA) buffer and treated with RNase A. The obtained samples were electrophoresed for 2 hours at 75 V on 1.8% agarose gels. The recovered DNA was stained with ethidium bromide and visualized by UV light to exhibit DNA ladder. The control groups treated with DMSO (expressed as C in FIG. 3) and HPR at 0.01% did not show any DNA ladder while the DNA band of the ladder shape caused by DNA fragmentation was well detected, when the cells were treated with KCBG10 and KCBG41 of the present invention (FIG. 3). Also, similarly to the result from the effect on the cell proliferation, KCBG10 at a low concentration showed DNA fragmentation in MCF-7 cells and KCBG41 at a similar concentration showed DNA fragmentation in HCT116 cells.

3-2) Cell Biological Assay

Figure 4:
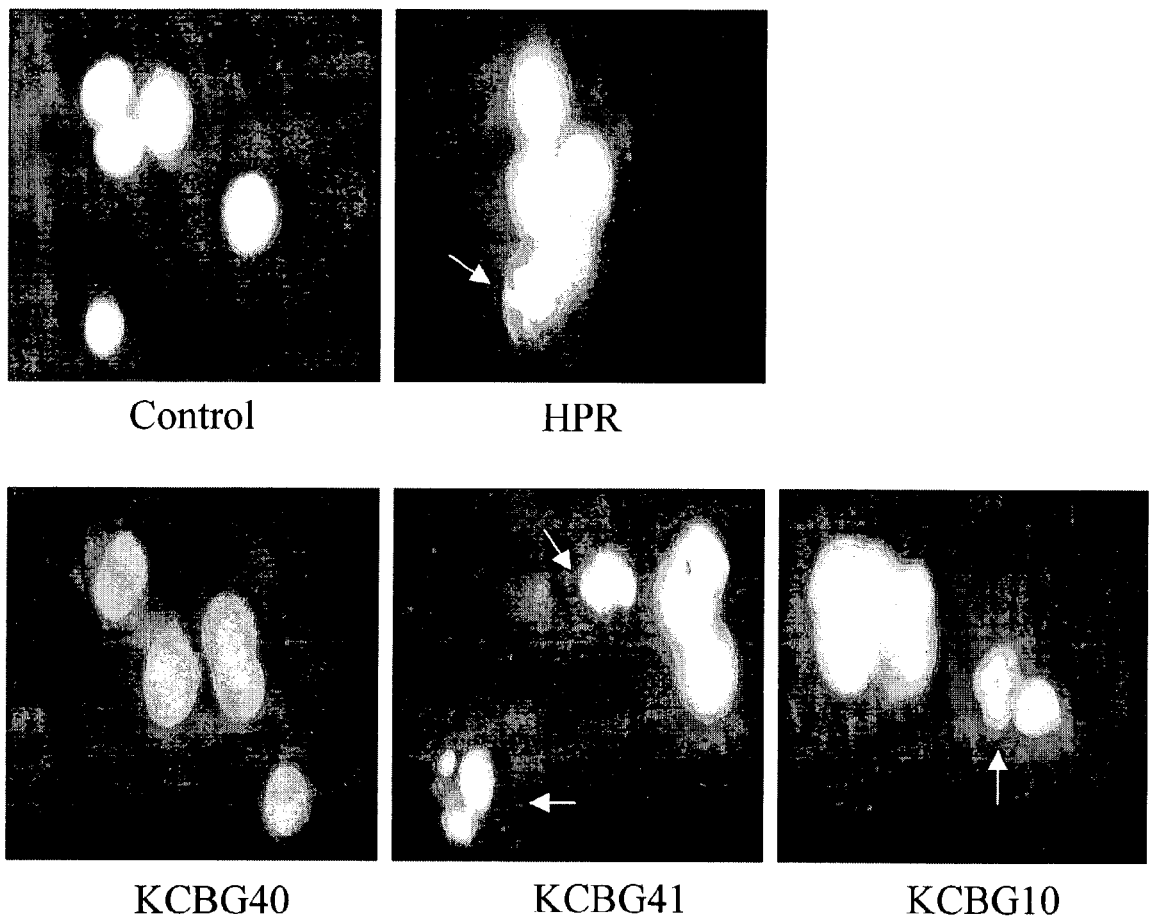
FIG. 4 is the microscopic photographs of nuclei in colon cancer cells HCT116 stained by DAPI 36 hours after being treated with the respective retinoid derivatives at a concentration of 5 μM, showing nuclear condensation and fragmentation.
Figure 5:
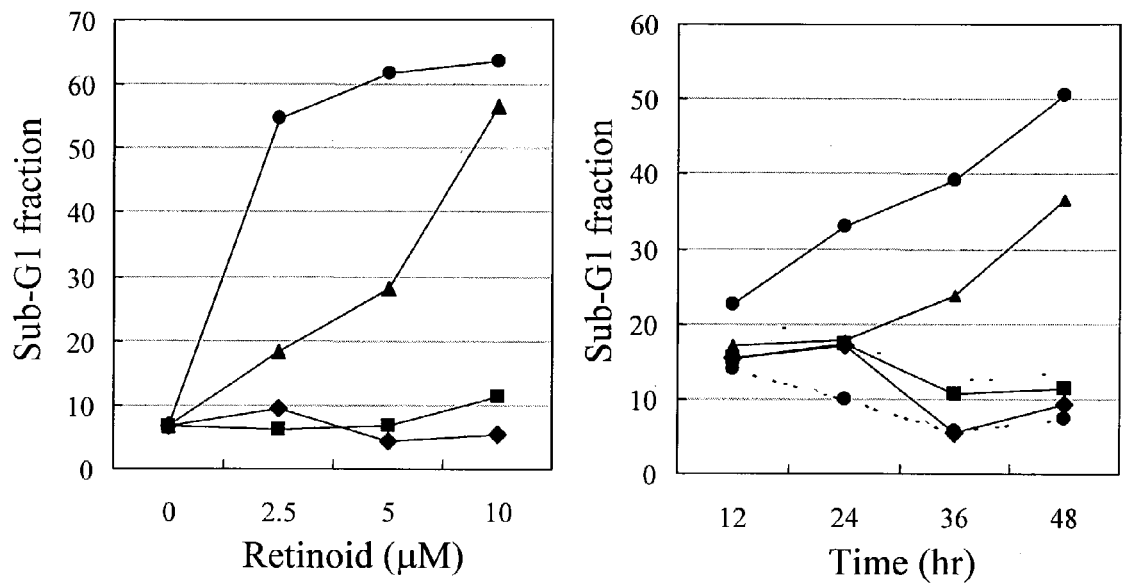
FIG. 5 is the quantitative results of the sub-G1 contents, as measured by an FACS analysis, in colon cancer cells HCT116 and breast cancer cells MCF-7 to which the respective retinoid derivatives were treated at a concentration of 5 μM, showing the apoptosis levels of cancer cells.
Figure 5:
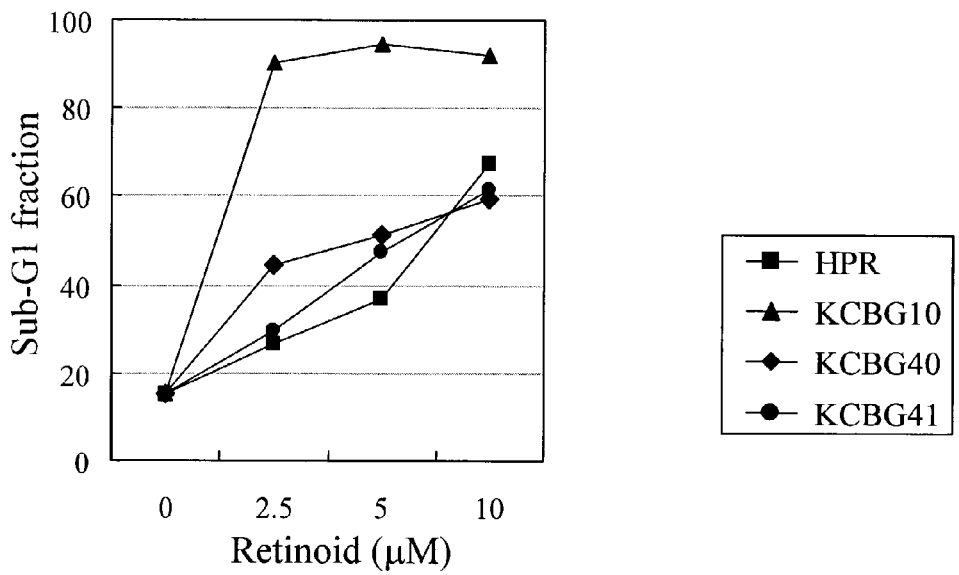
Figure 6:
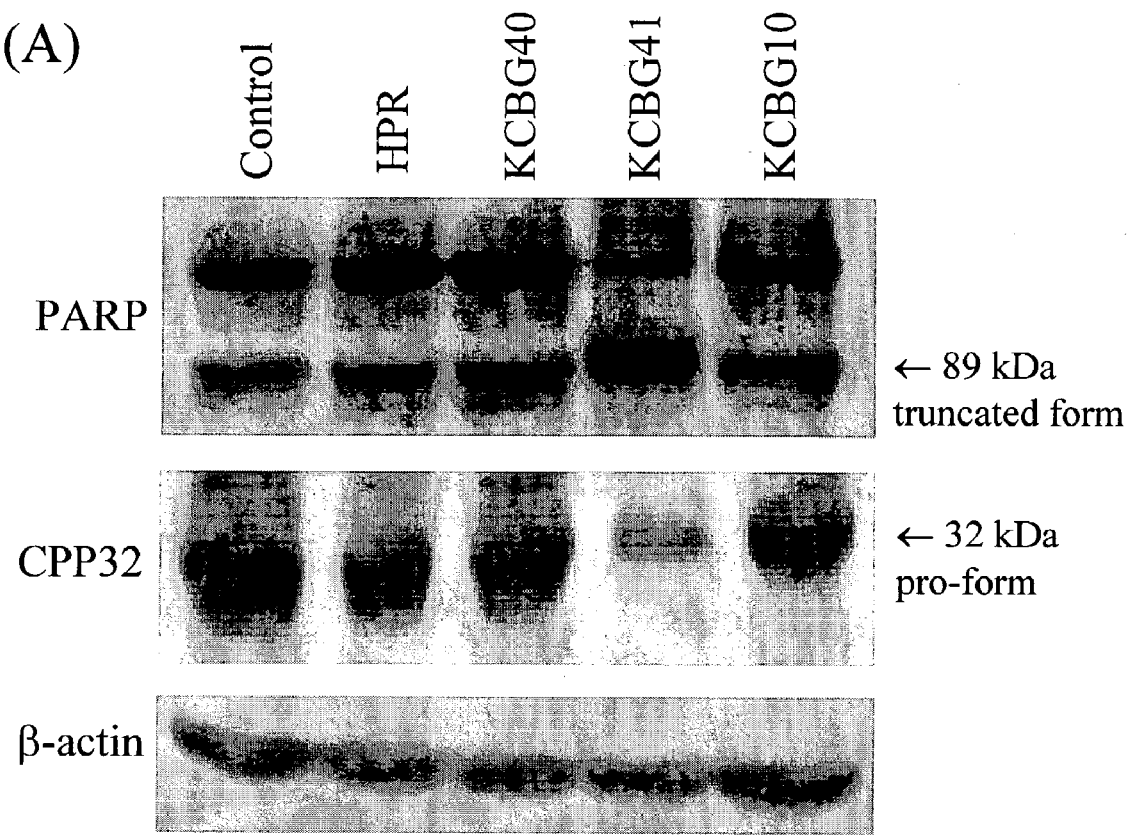
FIG. 6 is the cleavage results of PARP and CPP-32, by a Western blotting analysis, derived from colon cancer cells HCT 116 to which the respective retinoid derivatives were treated.
Figure 6:
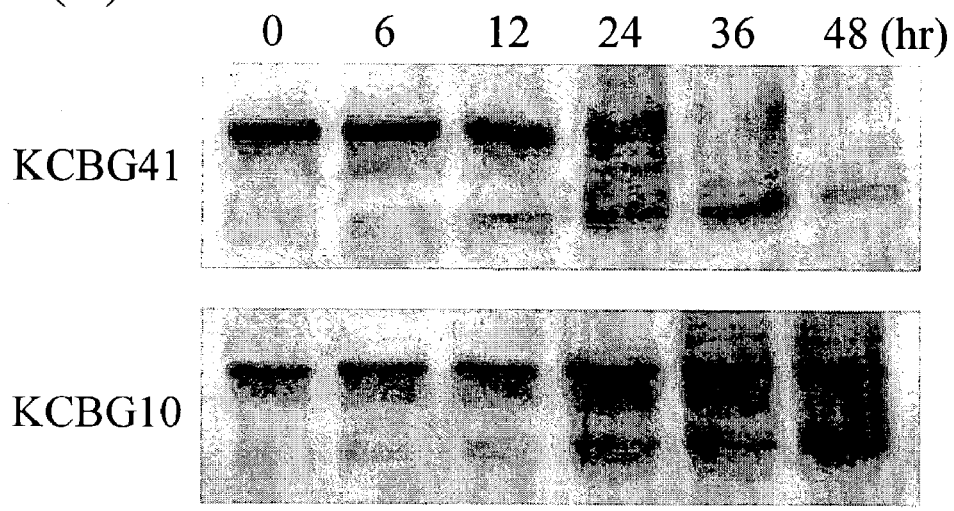

By DAPI (4,6-diamidino-2-phenylindole) staining assay for staining DNA in cellular nucleus, nuclear condensation and fragmentation, characteristic features of apoptosis, were observed. HCT116 cells treated with HPR, KCBG10, KCBG40 and KCBG41 at a concentration of 5 μM for 36 h largely showed nuclear fragmentation (FIG. 4). In FIG. 4, the control represents non-treated cells. The sub-G1 DNA contents of colon cancer HTC116 cells and breast cancer MCF-7 cells were measured by FACS (Fluorescence-Activated Cell Sorter) assay to quantify the apoptosis (FIG. 5). Finally, in order to further characterize the apoptosis observed in retinoid derivative-treated cells, the cleavage of apoptosis-related proteins, including PARP (poly(ADP-ribose)polymerase) and CPP32 (caspase-3) by Western blotting. KCBG10 and KCBG41 at 5 μM concentration induced the cleavage of the proteins (FIG. 6A). PARP cleavage occurred in a time-dependent manner, in parallel with the induction of apoptosis (FIG. 6B). C in FIG. 6 represents the result of Western blotting of non-treated cells.

These results suggest that the retinoid derivatives according to the present invention have effects inhibiting the proliferation of cancer cells by inducing apoptosis of cancer cells and such anti-proliferation effects on cancer cells of the retinoid derivatives according to the present invention is mainly due to the induction of apoptosis.

Experimental Example 4

Effect of Retinoid Derivatives on Retinoid Receptors

Figure 7:
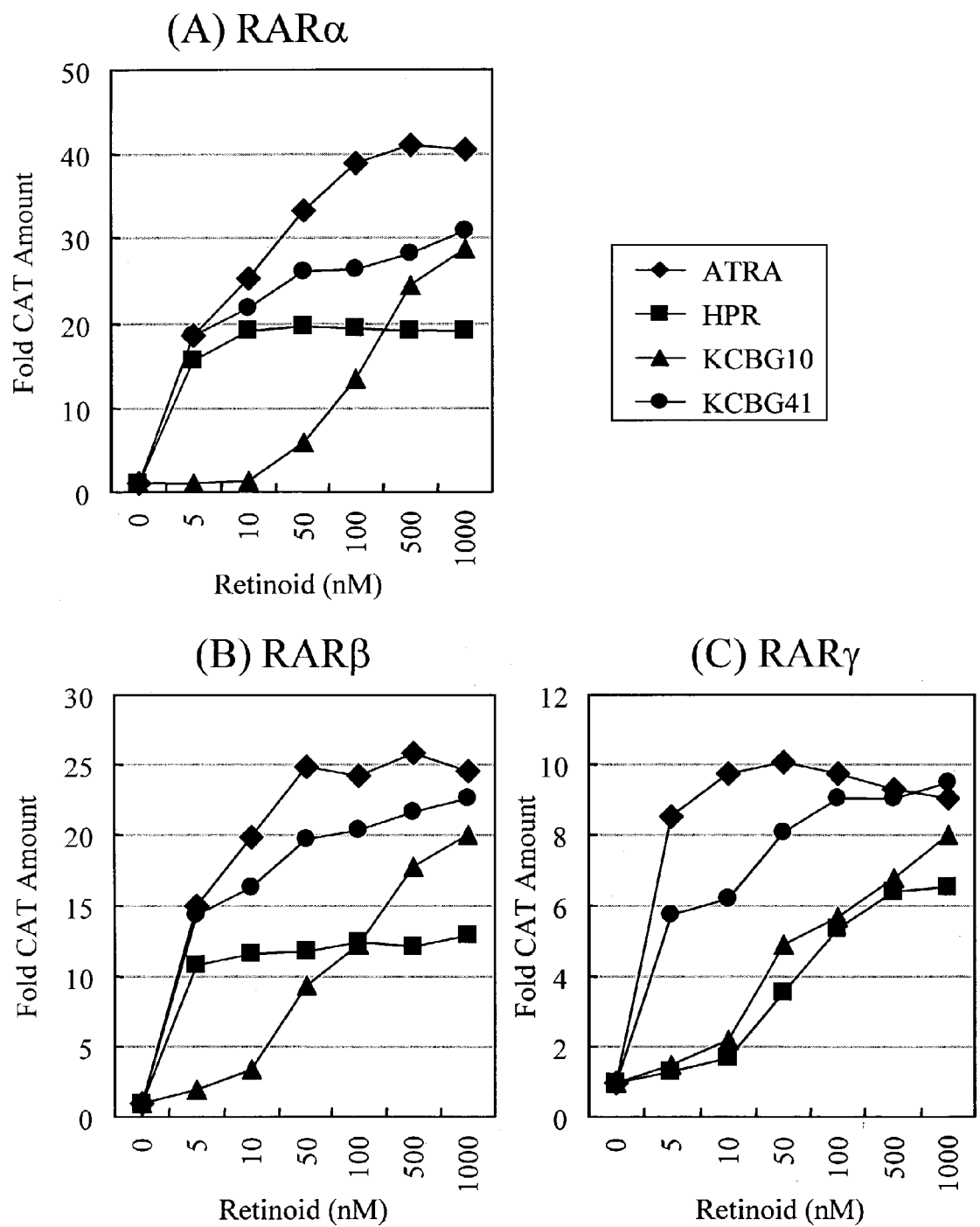
FIG. 7 shows the effects of the retinoid derivatives on retinoid receptors as the results of a CAT ELISA analysis.

In order to demonstrate the effect of the retinoid derivcatives of the present invention on activities of retinoid receptors, cells were cotransfected with expression vectors of respective receptor subfamilies and a reporter gene. As the reporter gene, chloramphenicol acetyltransferase (CAT) gene was used. Transfection was carried out by the activated-dendrimer method using SuperFect (QIAGEN), according to the protocol suggested by the manufacturer. The colon cancer cells were plated at $10^6$ in 6-well. At next day, the mixture of DNA (2 μg) and SuperFect reagent was added to the cells. After overnight transfection, the media were exchanged with fresh media containing retinoid at various concentrations for 24 hours and washed with cold 1×PBS. The cells were collected, suspended in 100 μl of 0.25M Tris-HCl (pH 7.6) and lysed by 3 freezing-thawing cycles. After centrifugation (12,000×g, 10 min, 4° C.), 100 μl of the supernatant was recovered. 10 μl of the recovered supernatant was tested for activity of β-galactosidase according to standard prosedures (Sambrook et al., 1989) and 50 μl of the recovered supernatant were tested for activity of the reporter by the CAT ELISA (Boeringer Mannheim, Germany) method. The obtained data for activity of the reporter was normalized with respect to β-gal activity for comparison. The cells were treated with retinoid derivatives KCBG10 and KCBG41, as the test compounds, and ATRA and HPR, as the control comounds at 1 μM and compared for expression levels of the CAT enzyme. The results are shown in FIG. 7.

Activities of KCBG10 and KCBG41 were compared to those of ATRA (Al-trans retinoic acid) and HPR. As the concentration increased, KCBG41 shows activity at a level of about 50% of ATRA and HPR in three RAR subfamilies (retinoic acid receptors: RARα, RARβ, RARγ). KCBG10 did not have activity at a low concentration but showed an increase of activity as the concentration increased. Since the great side effects of ATRA is due to absence of specificity to the RAR subfamilies or high activity to them, it is presumed that HPR has relatively low side effects. It is presumed that KCBG41 has side effects at a level of 50% of ATRA and HPR and KCBG10 has similar to or less than that of HPR.

Experimental Example 5

Effect of Retinoid Derivatives Inhibiting AP-1

Figure 8:
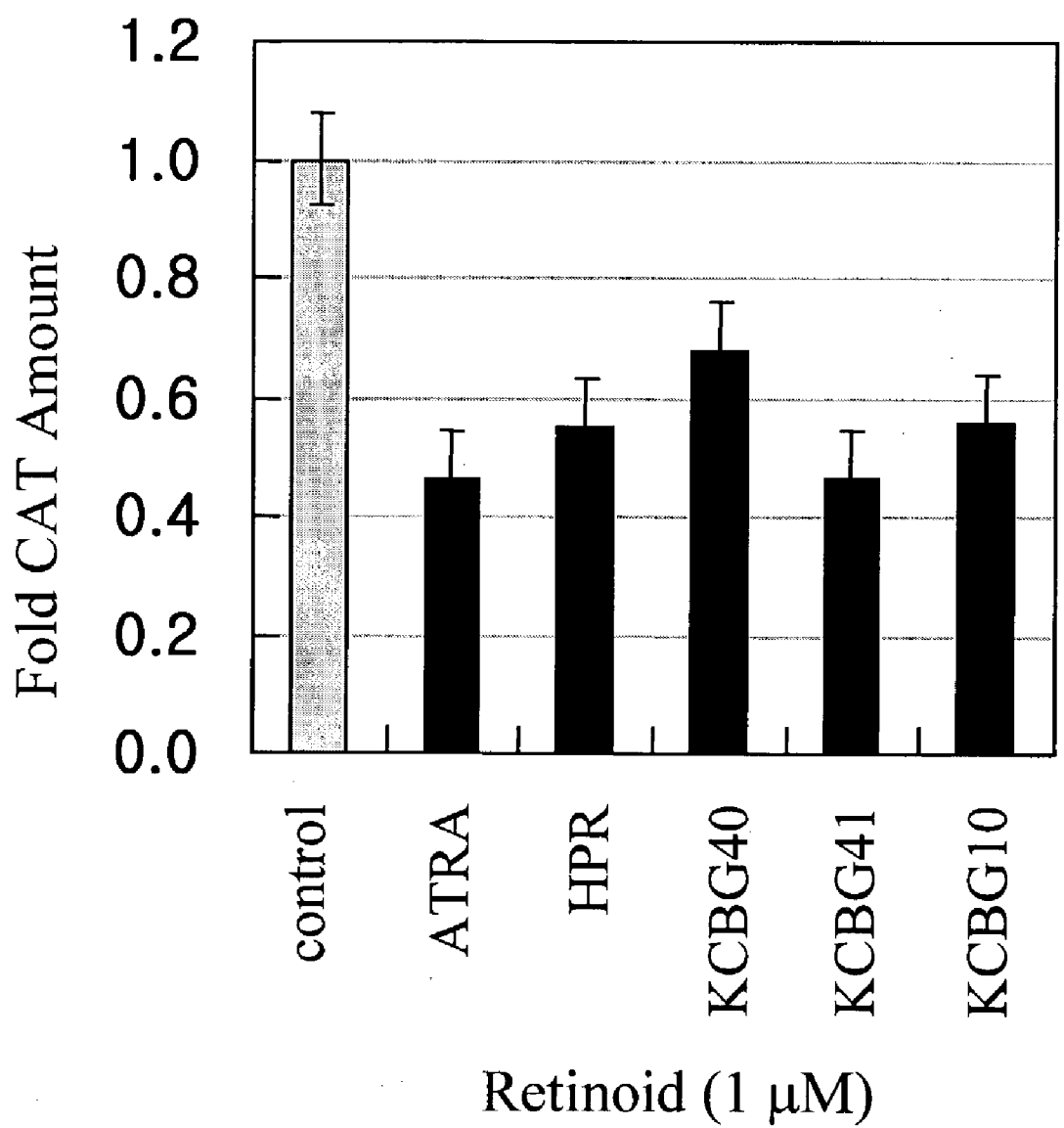
FIG. 8 shows the effects of the retinoid derivatives on AP-1 activity as the results of an ELISA analysis.

In order to see whether the retinoid derivatives according to the present invention directly suppressed AP-1, like the existing retinoids, cells were cotransfected with expression vectors of respective receptor subfamilies, c-Jun, a component of AP-1, and a reporter gene. As the reporter gene, the CAT enzyme gene with a site recognizing AP-1 of collagenase was used. The cells were treated with retinoid derivatives KCBG10, KCBG40 and KCBG41 as test compounds and DMSO, HPR and ATRA (retinoic acid) as control compounds at 1 μM and compared for expression levels of the CAT enzyme. The results are shown in FIG. 8.

KCBG10 and KCBG41 of the present invention suppressed AP-1 activity similar extents (50%) of the conventional ATRA and HPR. From these results, it is noted that KCBG10 and KCBG41 maintain the AP-1 suppressing effects.

Experimental Example 6

Effect of Retinoid Derivatives Inhibiting Metastasis and Filtration of Cancer

Figure 9:
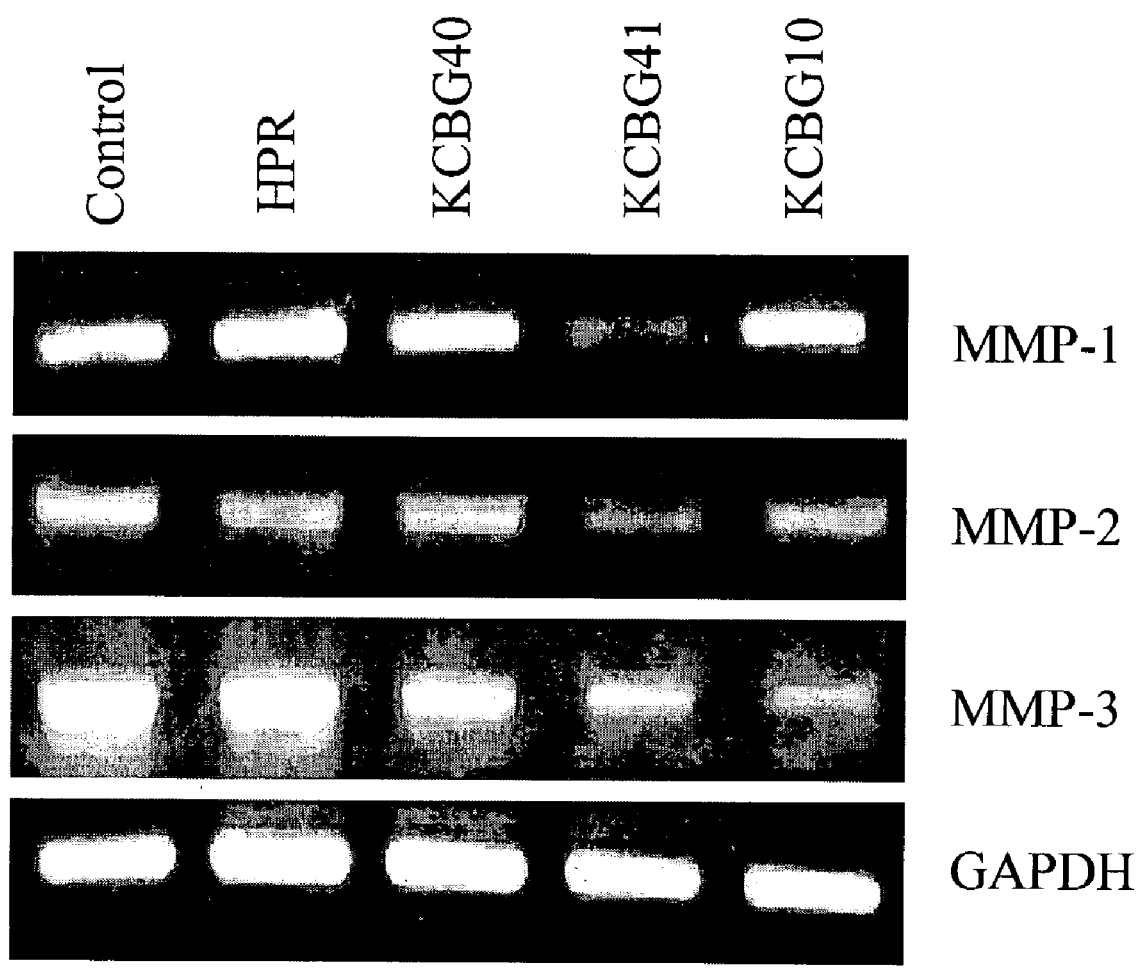
FIG. 9 shows the inhibitory effects of the retinoid derivatives on cancer metastasis and infiltration as the results of RT-PCR.

Previously, it was shown that the synthetic retinoid derivatives inhibit the transcriptional activity of AP-1. Also, it is well known that MMP (matrix metalloproteinase), a main target gene of AP-1 is involved in metastasis of cancer cells. Therefore, the inhibitive effects of the retinoid derivatives on metastasis of cancer was examined by RT-PCR analysis. Colon cancer HCT116 cells were treated with 1 μM retinoid for 36 hours. RNA was isolated from the cells and mRNA expression levels of MMP-1, -2 and -3 were analyzed by RT-PCR. For MMP-1 and MMP-2, HPR and KCBG40 affected very little, while KCBG10 weakly and KCBG41 strongly inhibited their expression. As the control, GAPDH was used and it was confirmed that its expression was not affected by retinoid. Meanwhile, the expression level of MMP-3 was affected weakly by KCBG40, intermediately by KCBG41 but strongly by KCBG10 (FIG. 9). From these results, it was noted that KCBG10 and KCBG41 regulate expressions of MMPs according to their kinds.

Accordingly, it is possible for KCBG10 and KCBG41 of the present invention to inhibit metastasis and invasion of cancer cells much more than the conventional retinoids.

Experimental Example 7

Effect of KCBG60 on Proliferation of Cancer Cell

In order to confirm the effects of KCBG60 on proliferation of cancer cells, colon cancer cells and liver cancer cells were treated with KCBG60 and precursors thereof, ATRA, 4-HPR, and phenyl butyrate at various concentrations and stained with trypan blue that permeates selectively in dead cells. Surviving cells, which had not be stained by trypan blue were counted and the results are shown in Table 3 as relative surviving cells (%).

TABLE 3

Effects of KCBG60 and precursors thereof on proliferation of cancer cells

| | HCT116 | | | | | DLD-1 | | | | | SK-HEP-1 | | | | |
|---|---|---|---|---|---|---|---|---|---|---|---|---|---|---|---|
| μM | 0 | 0.5 | 1 | 5 | 10 | 0 | 0.5 | 1 | 5 | 10 | 0 | 0.5 | 1 | 5 | 10 |
| RA | 100 | 95 | 92 | 85 | 78 | 100 | 110 | 105 | 103 | 70 | 100 | 105 | 103 | 89 | 70 |
| B | 100 | 103 | 103 | 95 | 90 | 100 | 105 | 103 | 102 | 92 | 100 | 102 | 103 | 95 | 87 |
| HPR | 100 | 91 | 70 | 45 | 13 | 100 | 94 | 85 | 63 | 28 | 100 | 90 | 73 | 45 | 15 |
| KCBG60 | 100 | 90 | 75 | 45 | 10 | 100 | 95 | 85 | 60 | 30 | 100 | 90 | 75 | 48 | 10 |

RA: ATRA, B: phenyl butylate

When colon cancer HCT116 cells were treated with 10 μM ATRA and phenyl butyrate, the inhibition of proliferation was as low as 10 to 30%. On the other hand, KCBG60 began to inhibit proliferation at 0.5 μM and to more than 90% at 10 μM. In colon cancer DLD-1 cells and liver cancer SK-Hep-1 cells, similar data were obtained.

Ii is found from the above results, that KCBG60 exerts the inhibitory effects against proliferation of cancer cell.

Experimental Example 8

Effects of KCBG60 Inducing Apoptosis

It is presumed that the effects of KCBG60 inhibiting the cell proliferation is due to the induction of apoptosis and the interception of cell division. In order to determine the mechanism by which KCBG60 inhibit the proliferation of cancer cells, morphological change by KCBG60 and its precursors were observed.

Figure 10:
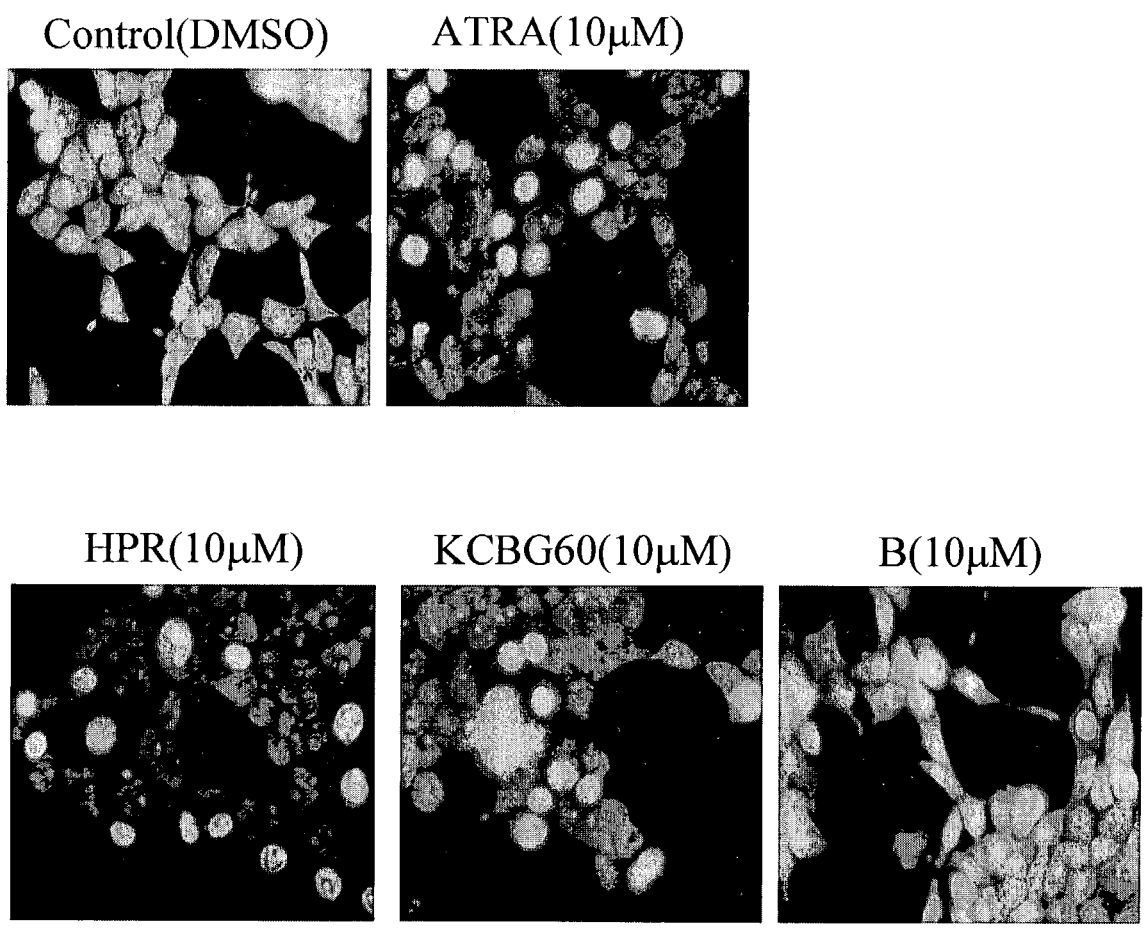
FIG. 10 shows cancer cells that were treated with KCBG60 or precursors thereof and double stained with acridine orange and ethidium bromide acridin.

Cells were treated with KCBG60 and its precursors, ATRA, HPR and phenyl butylate at a concentration of 10 μM for 96 hours and double stained with acridine orange and ethidium bromide (FIG. 10). When treated with 0.01% DMSO or phenyl butyrate, cells remained normal green color, indicating survival of most cells. In contrast, when treated with 10 μM of KCBG60, cells were stained with orange color, indicative of apoptosis upon which the staining reagent permeated the cells. Therefore, the anti-proliferation effect of KCBG60 is due to the induction of apoptosis.

Figure 11:
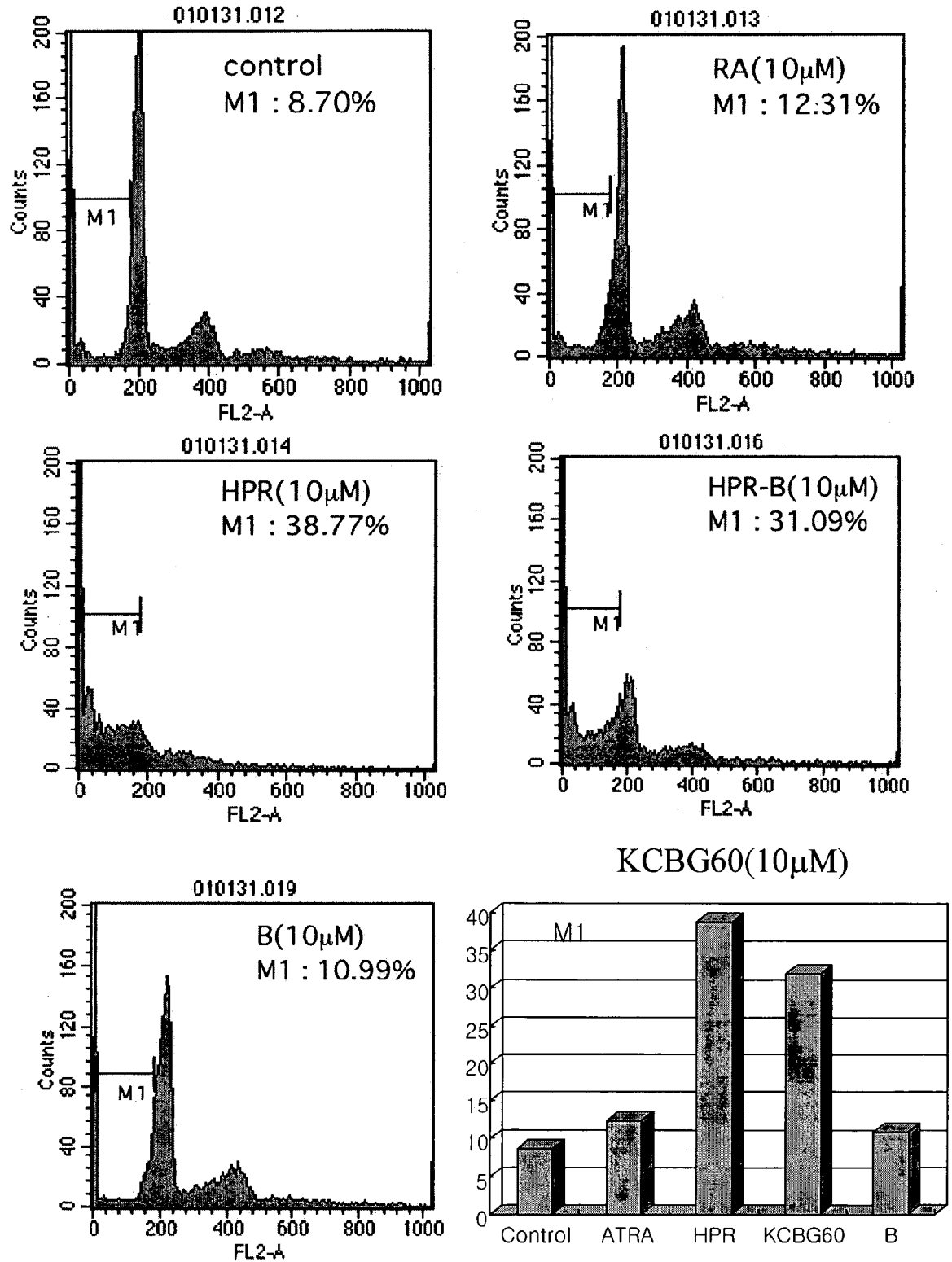
FIG. 11 is the results of FACS analysis of cancer cells to which KCBG60 or precursors thereof were treated.

In order to quantitatively determine the levels of apoptosis, the cells treated with the same conditions as above were subjected to FACS analysis to measure DNA contents (FIG. 11). Upon comparing the relative rate of dead cells having a DNA content of 2N or less, the KCBG60-treated group and HPR-treated group showed much higher rates than other groups.

Figure 12:
FIG. 12 is the results of DAPI staining of cancer cells to which KCBG60 or precursors thereof were treated.
Figure 12:
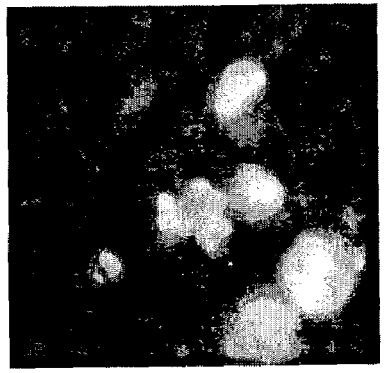
Figure 12:
Figure 12:
Figure 12:
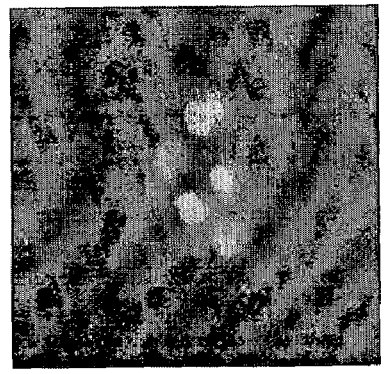

Meanwhile, HPR which is a precursor during the synthesis process of KCBG60 is known to induce apoptosis. Considering that the cells aggregated into small spherical mass upon treatment with KCBG60, KCBG60 is expected to induce apoptosis. In order to confirm apoptosis induced by KCBG60 once again, KCBG60-treated HCT116 cells were stained with DAPI and observed for nuclear condensation, an indicative of apoptosis (FIG. 12). When treated with 0.01% DMSO and phenyl butylate, nuclei were observed normal. In contrast, cells treated with KCBG60 and retinoid derivatives known to induce apoptosis showed small spots, indicating nuclear condensation.

Figure 13:
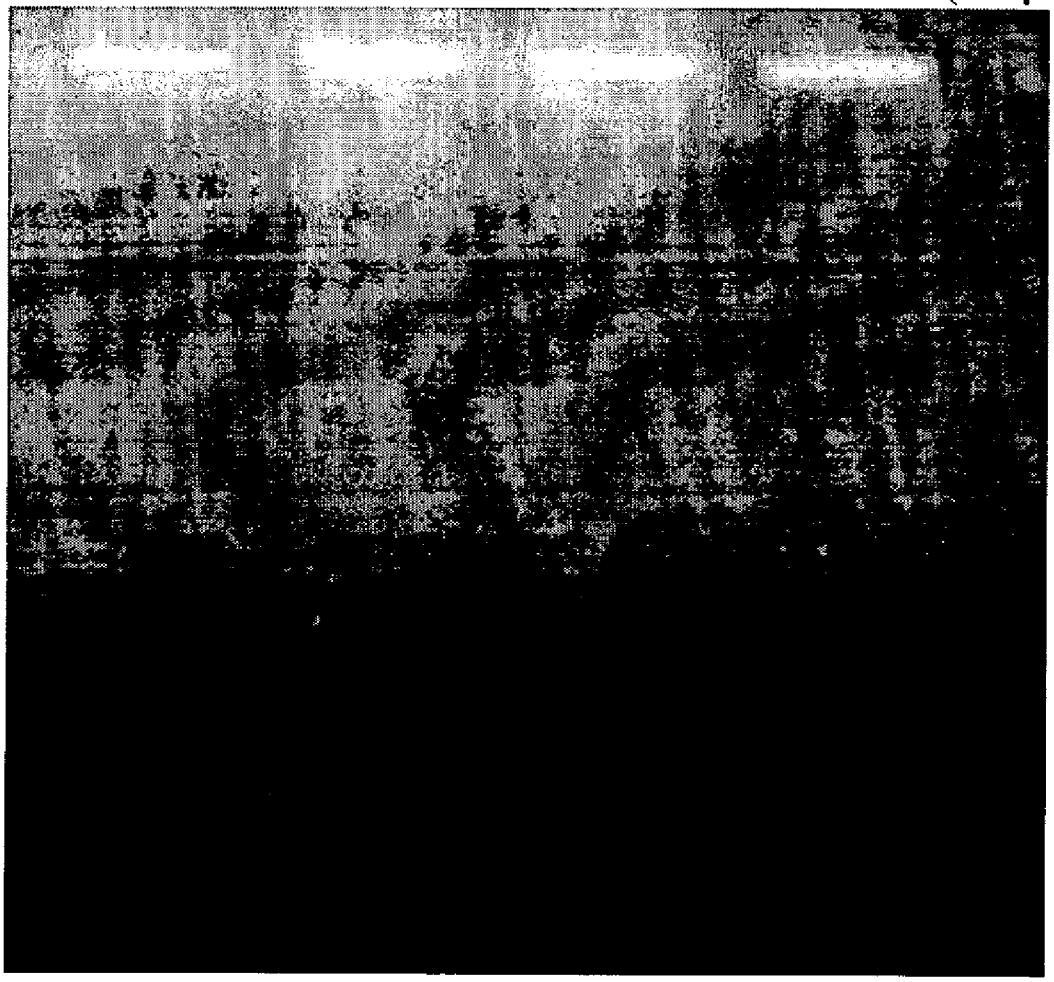
FIG. 13 shows the fragmentation levels of chromosomal DNAs in cancer cells to which KCBG60 or precursors thereof were treated.

In order to confirm the above results, DNA was separated from the cells treated as above and examined for DNA fragmentation by agarose gel electrophoresis (FIG. 13). Treatment with 0.01% DMSO and pheny butylate did not induce any fragmentation of chromosomal DNA. In contrast, DNA ladder caused by fragmentation of chromosomal DNA was detected, when the cells were treated with KCBG60 and ATRA.

From these results, it was noted that KCBG60 of the present invention inhibits proliferation by apoptosis of cancer cells.

Experimental Example 9

Effect of KCBG60 on Retinoid Receptor Activity

In order to confirm the effect of KCBG60 according to the present invention on retinoid receptor activity, cells were cotransfected with expression vectors of receptor subfamilies and reporter genes. As the reporter gene, chloramphenicol acetyltransferase (CAT) with a transcription control site reactive to respective receptors was used. The transfected cells were treated with KCBG60 and its precursors, ATRA, HPR and phenyl butylate at 1 μM and measured for the expression levels of CAT enzyme (Table 4). As RA (retinoic acid), all-trans RA (ATRA) was used for RAR receptors and 9-cis RA was used for RXR receptors.

TABLE 4

Effects of KCBG60 and its precursors on activities of retinoid receptors

| | RARα | | RARβ | | RARγ | | RXRα | | RXRβ | | RXRγ | |
|---|---|---|---|---|---|---|---|---|---|---|---|---|
| | − | + | − | + | − | + | − | + | − | + | − | + |
| Control | 1.0 | 1.0 | 1.0 | 1.0 | 1.0 | 1.0 | 1.0 | 1.0 | 1.0 | 1.0 | 1.0 | 1.0 |
| RA | 17.3 | 66.7 | 17.3 | 65.2 | 14.1 | 49.3 | 2.6 | 11.5 | 1.2 | 15.6 | 1.8 | 21.3 |
| HPR | 9.9 | 30.4 | 9.1 | 25.3 | 4.5 | 24.8 | 1.0 | 1.5 | 0.6 | 1.4 | 1.3 | 1.5 |
| KCBG60 | 0.7 | 1.1 | 0.8 | 1.0 | 0.6 | 1.9 | 0.9 | 1.3 | 0.5 | 1.1 | 1.2 | 1.4 |
| B | 0.7 | 0.8 | 0.7 | 0.9 | 0.8 | 1.1 | 1.1 | 1.2 | 0.5 | 1.1 | 1.1 | 1.2 |

HPR, which is known to function by a receptor-independent mechanism, showed about 50% activity of ATRA for all 3 RARs. In contrast, the KCBG60-treated group showed activity as low as the control and phenyl butylate-treated group. In the transcriptional activity for RXR type receptors, similar results were obtained.

These results indicate that KCBG60, different from the conventional retinoids, has almost no activity for RARs and RXRs and thus could be less related with side effects.

Experimental Example 10

Effect of KCBG60 Inhibiting AP-1 Activity

In order to see whether KCBG60 of the present invention directly suppressed AP-1, like the existing retinoids, cells were cotransfected with expression vectors of respective receptor subfamilies, c-Jun, a component of AP-1, and a reporter gene. As the reporter gene, the CAT enzyme gene with a site recognizing AP-1 of collagenase was used. The cells were treated with KCBG60 and its precursors, ATRA, HPR and phenyl butylate at 1 μM and compared for expression levels of the CAT enzyme (Table 5).

TABLE 5

Effects of KCBG60 and its precursors on activity of AP-1(c-Jun)

| | −c-Jun/−RARα | +c-Jun/−RARα | +c-Jun/+RARα |
|---|---|---|---|
| Control | 1.0 | 5.0 | 5.0 |
| RA | 0.6 | 3.5 | 2.0 |
| HPR | 0.7 | 3.7 | 2.2 |
| HPR-B | 0.6 | 3.6 | 2.4 |
| B | 1.0 | 4.7 | 5.3 |

As shown in Table 5, KCBG60 repressed AP-1 activity to similar extents (about 50%) of ATRA or HPR. Phenyl butylate, not related with AP-1 activity, did not affect as expected.

From these results, it is noted that KCBG60 of the present invention maintain the AP-1 repressing effects.

Experimental Example 11

Effect of KCBG60 on Metastasis and Invasion of Cancer

Figure 14:
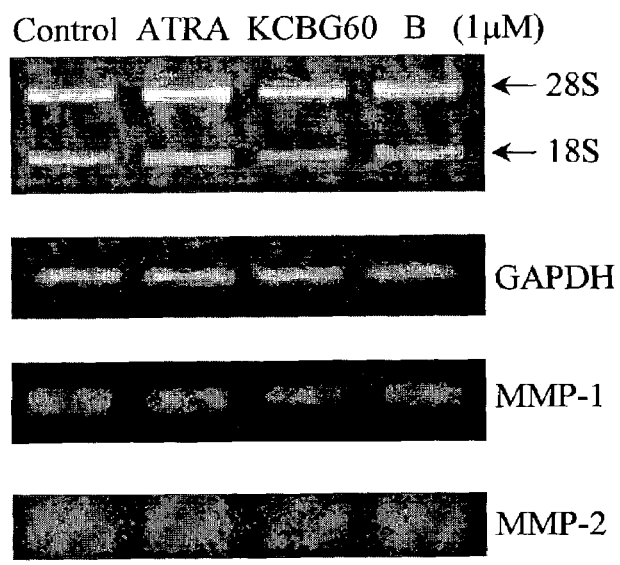
FIG. 14 shows the expression levels of MMP in cancer cells to which KCBG60 or its precursor were treated.
Figure 14:
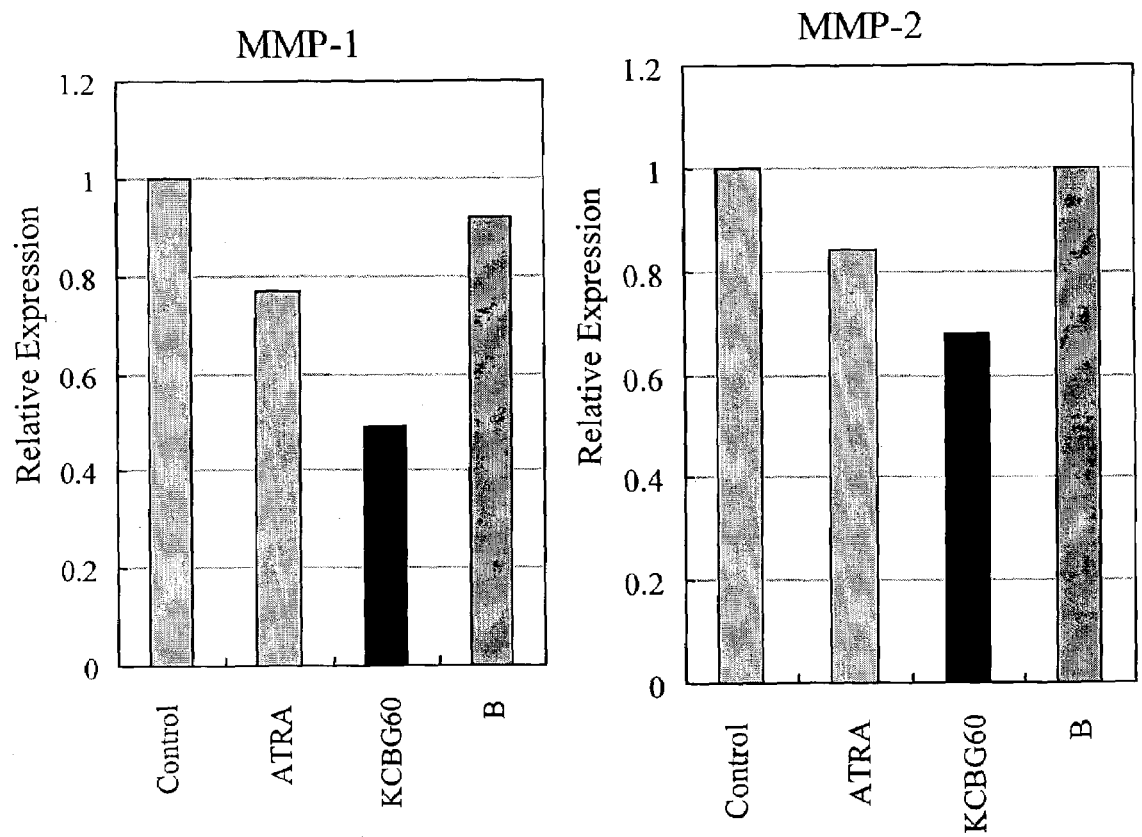

In order to examin whether KCBG60 of the present invention inhibits metastasis of cancer cells, the expression level of MMP (matrix metalloproteinase), known to be involved in metastasis of cancer cells, inhibited by KCBG60 was measured. Colon cancer HCT116 cells were treated with KCBG60 and its precursor, ATRA and phenyl butylate at a concentration of 1 μM for 24 hours. RNA was isolated from the cells and mRNA expression levels of MMP-1, -2 and -3 were analyzed by RT-PCR (FIG. 14).

RT-PCR analysis revealed that mRNA levels of MMPs were about 50% reduced for MMP-1, which was two times increased compared to ATRA and phenyl butylate. For MMP-2, KCBG60 showed two times higher inhibitory expression level compared to ATRA. In contrast, phenyl butylate did not affect expression of MMP-2 at all.

Figure 15:
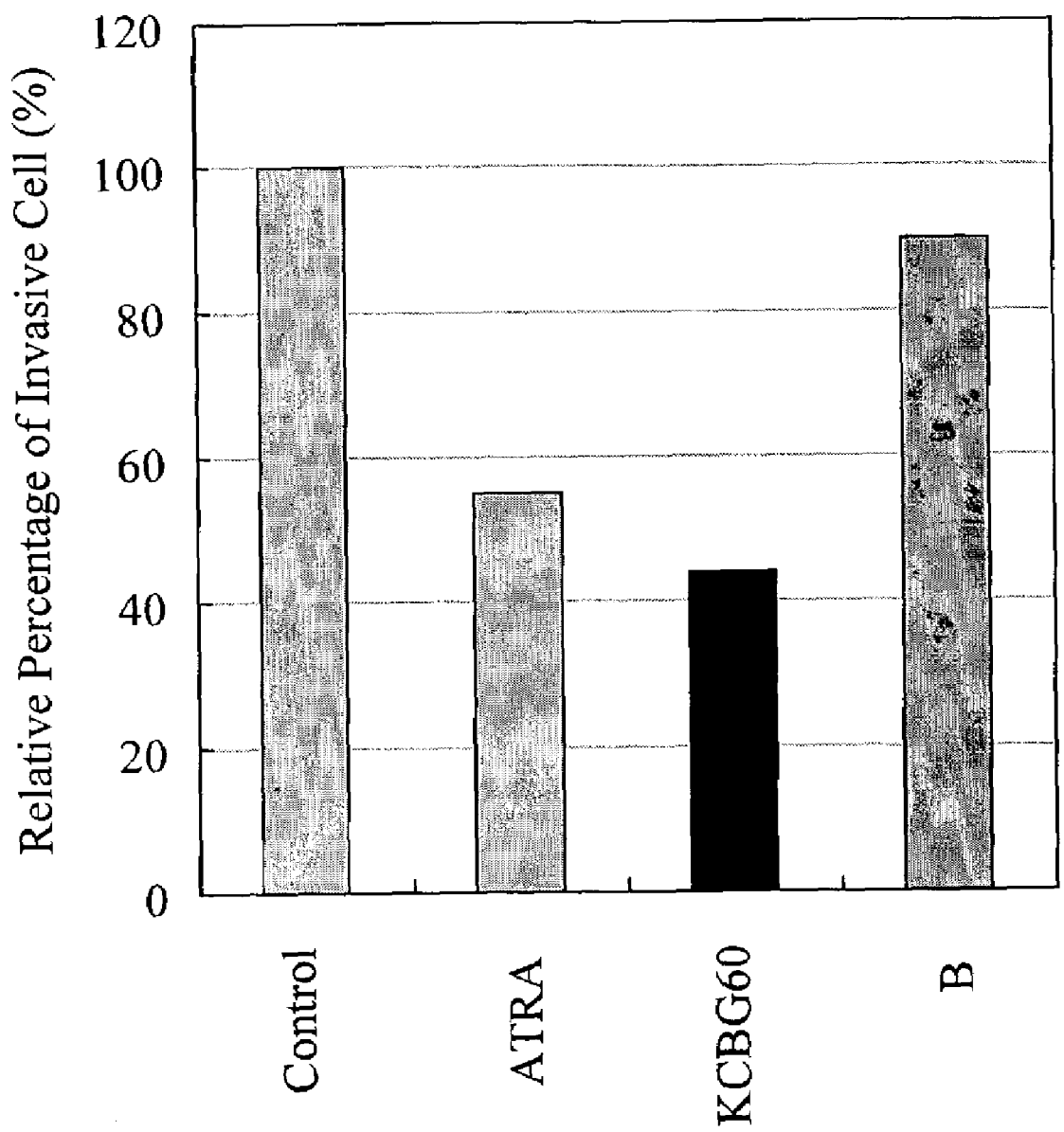
FIG. 15 shows the infiltration levels of cancer cells to which KCBG60 or precursors thereof were treated.

Meanwhile, to determine the effect of KCBG60 on the invasion potential of HCT116 cells, in vitro assay was performed. HCT116 cells were treated with KCBG60 and its precursor, ATRA, and phenyl butylate at a concentration of 1 μM for 8 hours and transferred to a filter coated with matrigel at the top layer. After cultivation for a predetermined period of time, the number of cells migrating to lower side of the filter was measured to determin the invasion level (FIG. 15). KCBG60 significantly (50%) reduced the number of invaded cells, which was superior to ATRA (40%). Phenyl butylated did not show invasion inhibiting effect.

From the above results, it is noted that KCBG60 according to the present invention prominently inhibit metastasis and infiltration of cancer cells, compared to its components.

As described above, the skilled in the art to which the present invention belongs appreciate that the present invention may be practiced in another embodiment without departing the spirit or features of the present invention. Thus, it should be understood that the above-described Examples and Experimental Examples are for illustration but not for limitation. The present invention covers all the changes and modifications from spirit and scope of the invention as defined by the appended claims and equivalents thereof rather than the foregoing detailed description of the invention.

The retinoid derivatives according to the present invention inhibit proliferation of cancer cells more effectively than their precursors through complementary actions between components and are thus expected to show excellent anticancer effects. The retinoid derivatives according to the present invention have a relatively low activity against all the subspecies of retinoid receptors but effectively inhibit activity of AP-1. Therefore, they have side effects lower than ATRA, an existing retinoid type drug, and particularly, equal to or lower than HPR. Accordingly, anticancer agents comprising the retinoid derivatives according to the present invention as an active ingredient may overcome poor efficiency and side effects, the problems of the precursor and show superior anticancer effects, being useful in the chemical prevention and treatment of cancer.

What is claimed is:

1. A compound of the formula I:

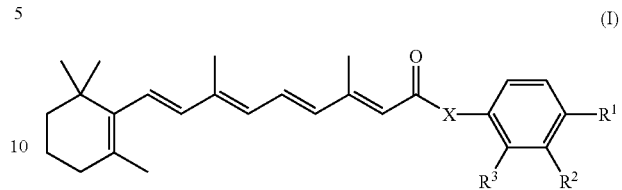

(I)

wherein

X is O, NH or S; $R^1$ and $R^2$, which may be identical or different, are each independently —OH, —SH, —NH$_2$, —COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each R is CH$_2$, O, NH or S, $R^4$ is H or $C_1$–$C_6$ alkyl, and each m is an integer of 0 to 5; and $R^3$ is H, with the proviso that if X is O, $R^1$ and $R^2$, which may be identical or different, are not each independently —OH, —NH$_2$, —COOH, —R(CH$_2$)$_m$CH$_3$, wherein R is CH$_2$, NH or O, m is 0 to 5, —RCO(CH$_2$)$_m$CHCH$_3$CH$_3$, wherein R is NH, m is 0 to 5, —RCOCH$_2$(CH$_2$)$_m$CH$_3$, wherein R is NH, m is 0 to 5, —RCO(CH$_2$)$_m$NR$^4$CH$_3$, wherein R is NH, m is 0, $R^4$ is H or $C_{1-6}$ alkyl, —RSO$_2$CH$_2$(CH$_2$)$_m$CH$_3$, wherein R is NH, m is 0 to 5, or pharmaceutically acceptable salts thereof.

2. The compound according to claim 1, which is selected from the group consisting of 2-butyryloxy-5-(2E,4E,6E,8E)-[3,7-dimethyl-9-(2,6,6-trimethyl-cyclohex-1-enyl)-nona-2,4,6,8-tetraenoylamino]-phenyl butanoate (KCBG34); 5-(2E,4E,6E,8E)-[3,7-dimethyl-9-(2,6,6-trimethyl-cyclohex-1-enyl)-nona-2,4,6,8-tetraenoylamino]-2-hydroxy-phenyl butanoate (KCBG35); (2E,4E,6E,8E)-[3,7-dimethyl-9-(2,6,6-trimethyl-cyclohex-1-enyl)-nona-2,4,6,8-tetraenoylamino]-(3-butylamino-4-hydroxy)-phenylamide(KCBG41), or pharmaceutically acceptable salts thereof.

3. A process for producing a compound of the formula I:

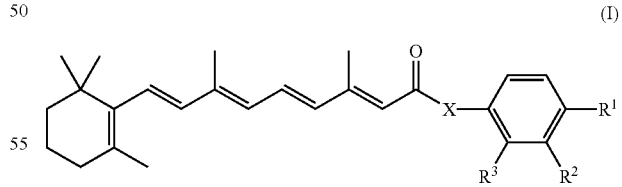

(I)

wherein (i) X is O, NH or S; $R^1$ and $R^2$, which may be identical or different, are each independently —OH, —SH, —NH$_2$, COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)

$CH_2CH_2CONH_2$, in which each R is $CH_2$, O, NH or S, $R^4$ is H or $C_1$–$C_6$ alkyl, and each m is an integer of 0 to 5; and $R^3$ is H, with the proviso that if X is O, $R^1$ and $R^2$, which may be identical or different are not each independently —OH, —$NH_2$, —COOH, —$R(CH_2)_mCH_3$, wherein R is $CH_2$, NH or O, m is 0 to 5, —$RCO(CH_2)_m$ $CHCH_3CH_3$, wherein R is NH, m is 0 to 5, $RCOCH_2$ $(CH_2)_mCH_3$, wherein R is NH, m is 0 to 5, —RCO $(CH_2)_mNR^4CH_3$, wherein R is NH, m is 0, $R^4$ is H or $C_{1-6}$ alkyl, —$RSO_2CH_2(CH_2)_mCH_3$, wherein R is NH, m is 0 to 5;

(ii) X is the same as defined above; $R^1$ and $R^3$, which may be identical or different, are each independently —OH, —SH, —$NH_2$, —COOH, —$R(CH_2,CH_3$, —$RCOCO$ $(CH_2)_mCH_3$, —$RCO(CH_2)_mCHCH_3CH_3$, —RCO $(CH_2)_mNR^4CH_3$, —$RCOCHOH(CH_2)_mCH_3$, —$RCOCH_2(CH_2)_mCH_3$, —$RCOCH_2CHOH(CH_2)_m$ $CH_3$, —$RCOCH_2(CH_2)_mCOOH$, —$RSO_2CH_2(CH_2)_m$ $CH_3$, —$RPO_2(OH)CH_2(CH_2)_mCH_3$ or $RCOCH(NH-COCH_3)CH_2CH_2CONH_2$, in which each R is $CH_2$, O, NH or S, $R^4$ is H or $C_1$–$C_6$ alkyl, and each m is an integer of 0 to 5; and $R^2$ is H, with the proviso that if X is O, $R^1$, and $R^3$, which may be identical or different, are not each independently —OH, —$NH_2$, —COOH, —$R(CH_2)_mCH_3$, wherein R, is $CH_2$, NH or O, m is 0 to 5, —$RCO(CH_2)_m$ $CHCH_3CH_3$, wherein R is NH, m is 0 to 5, —$RCOCH_2(CH_2)_mCH_3$ wherein R is NH, m is 0 to 5, —$RCO(CH_2)_mNR^4CH_3$, wherein R is NH, m is 0, $R^4$ is H or $C_{1-6}$ alkyl, —$RSO_2CH_2(CH_2)_mCH_3$, wherein R is NH, m is 0 to 5;

(iii) X is the same as defined above; $R^1$ is —OH, —SH, —$NH_2$, —COOH, —$R(CH_2)_mCH_3$, —$RCOCO(CH_2)_m$ $CH_3$, —$RCO(CH_2)_3CHCH_3CH_3$, —$RCO(CH_2)_m$ $NR^4CH_3$, —$RCOCHOH(CH_2)_mCH_3$, —$RCOCH_2$ $(CH_2)_mCH_3$, —$RCOCH_2CHOH(CH_2)_mCH_3$, —$RCOCH_2(CH_2)_mCOOH$, —$RSO_2CH_2(CH_2)_mCH_3$, —$RPO_2(OH)CH_2(CH_2)_mCH_3$ or $RCOCH(NHCOCH_3)$ $CH_2CH_2CONH_2$, in which each R is $CH_2$, O, NH or S, $R^4$ is H or $C_1$–$C_6$ alkyl, and each m is an integer of 0 to 5; $R^2$ is H; and $R^3$ is H, OH or Cl, with the proviso that when $R^2$ and $R^3$ are H, (a) if X is NH, $R^1$ is not —$RCO(CH_2)_mCHCH_3CH_3$, wherein R is O, m is 0 to 5, —$RCOCH_2(CH_2)_mCH_3$, wherein R is O, m is 0 to 5, —OH, —COOH, or —$R(CH_2)_mCH_3$, wherein R is O, m is 0 or 1, (b) if X is O, $R^1$ is not —$RCO(CH_2)_mCHCH_3CH_3$, wherein R is NH, m is 0 to 2, —$RCOCH_2(CH_2)_m$ $CH_3$, wherein R is NH, m is 0 to 2, —$R(CH_2)_mCH_3$, wherein R is $CH_2$, O or NH, m is 0 to 5, —COOH, —$NH_2$, —OH, —$RCO(CH_2)_mNR^4CH_3$, wherein R is O or NH, m is 0, $R^4$ is H or $C_{1-6}$ alkyl, —$RSO_2CH_2$ $(CH_2)_mCH_3$, wherein R is NH, m is 0 to 5, (c) if X is S, $R^1$ is not —$RCO(CH_2)_mCHCH_3CH_3$, wherein R is NH, m is 0 to 2, —$RCOCH_2(CH_2)_m$ $CH_3$, wherein R is NH, m is 0 to 2;

(iv) X is the same as defined above; $R^3$ is —OH, —SH, —$NH_2$, —COOH, —$R(CH_2)_mCH_3$, —$RCOCO(CH_2)_m$ $CH_3$, —$RCO(CH_2)_mCHCH_3CH_3$, —$RCO(CH_2)_m$ $NR^4CH_3$, —$RCOCHOH(CH_2)_mCH_3$, —$RCOCH_2$ $(CH_2)_mCH_3$, —$RCOCH_2CHOH(CH_2)_mCH_3$, —$RCOCH_2(CH_2)_mCOOH$, —$RSO_2CH_2(CH_2)_mCH_3$, —$RPO_2(OH)CH_2(CH_2)_mCH_3$ or $RCOCH(NHCOCH_3)$ $CH_2CH_2CONH_2$, in which each R is $CH_2$, O, NH or S, $R^4$ H or $C_1$–$C_6$ alkyl, and each m is an integer of 0 to 5; $R^2$ is H; and $R^1$ is H, OH or Cl, with the proviso that when $R^1$ and $R^2$ are H, (a) if X is NH, $R^3$ is not COOH, (b) if X is S, $R^3$ is not —$RCO(CH_2)_mCHCH_3CH_3$, wherein R is NH, m is 0 to 2, —$RCOCH_2(CH_2)_m$ $CH_3$, wherein R is NH, m is 0 to 2, (c) if X is O, $R^3$ is not —$RCO(CH_2)_mCHCH_3CH_3$, wherein R is NH, m is 0 to 2, —$RCOCH_2(CH_2)_m$ $CH_3$, wherein R is NH, m is 0 to 2, —$R(CH_2)_mCH_3$, wherein R is $CH_2$, O or NH, m is 0 to 5, —COOH, —$NH_2$, —OH, —$RCO(CH_2)_mNR^4CH_3$, wherein R is O or NH, m is 0, $R^4$ is H or $C_{1-6}$ alkyl, —$RSO_2CH_2$ $(CH_2)_mCH_3$, wherein R is NH, m is 0 to 5; or (v) X is the same as defined above; $R^1$, $R^2$ and $R^3$, which may be identical or different, are each independently —OH, —SH, —$NH_2$, —COOH, —$R(CH_2)_mCH_3$, —$RCOCO(CH_2)_mCH_3$, —$RCO(CH_2)_mCHCH_3CH_3$, —$RCO(CH_2)_mNR^4CH_3$, —$RCOCHOH(CH_2)_mCH_3$, —$RCOCH_2(CH_2)_mCH_3$, —$RCOCH_2CHOH(CH_2)_m$ $CH_3$, —$RCOCH_2(CH_2)_mCOOH$, —$RSO_2CH_2(CH_2)_m$ $CH_3$, —$RPO_2(OH)CH_2(CH_2)_mCH_3$ or $RCOCH(NH-COCH_3)CH_2CH_2CONH_2$, in which each R is $CH_2$, O, NH or S, $R^4$ is H or $C_1$–$C_6$ alkyl, and each m is an integer of 0 to 5, with the proviso that if X is O, $R^1$, $R^2$ and $R^3$, which may be identical or different, are not each independently —OH, —$NH_2$, —COOH, —$R(CH_2)_mCH_3$, wherein R is $GH_2$, NH or O, m is 0 to 5), —RCO $(CH_2)_mCHCH_3CH_3$, wherein R is NH, m is 0 to 5, —$RCOCH_2(CH_2)_mCH_3$, wherein R is NH, m is 0 to 5, —$RCO(CH_2)_mNR^4CH_3$, wherein R is O or NH, m is 0, $R^4$ is H or $C_{1-6}$ alkyl, —$RSO_2CH_2(CH_2)_mCH_3$, wherein R is NH, m is 0 to 5; or pharmaceutically acceptable salts thereof, which comprises reacting retinoic acid with a compound of the formula II:

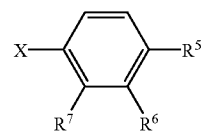

(II)

wherein X is the same as defined above; and $R^5$ and $R^6$ are each independently OH, $NH_2$ or SH and $R^7$ is H or Cl for the preparation of the above class (i) of the compounds of the formula I; $R^5$ and $R^7$ are each independently OH, $NH_2$ or SH and $R^6$ is H for the preparation of the above class (ii) of the compounds of the formula I; $R^5$ is OH, $NH_2$ or SH, $R^6$ is H and $R^7$ is H, OH or Cl for the preparation of the above class (iii) of the compounds of the formula I; $R^5$ is H, OH or Cl, $R^6$ is H and $R^7$ is OH, $NH_2$ or SH for the preparation of the above class (iv) of the compounds of the formula I; or $R^5$, $R^6$ and $R^7$ are each independently OH, $NH_2$ or SH for the preparation of the above class (v) of the compounds of the formula I to form a compound of the formula III:

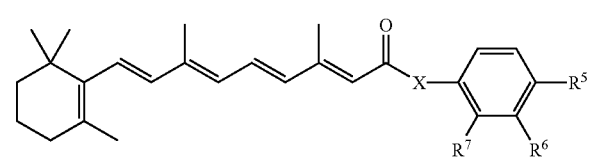

(III)

wherein X, $R^5$, $R^6$ and $R^7$ are the same as defined above and reacting the compound of the formula III with a compound of the formula IV:

$$W-Y \quad \quad (IV)$$

wherein W is —OH, —SH, —$NH_2$, —COOH, —$R(CH_2)_m$ $CH_3$, —$RCOCO(CH_2)_mCH_3$, —$RCO(CH_2)_mCHCH_3CH_3$, —$RCO(CH_2)_mNR^4CH_3$, —$RCOCHOH(CH_2)_mCH_3$, —$RCOCH_2(CH_2)_mCH_3$, —$RCOCH_2CHOH(CH_2)_mCH_3$, $RCOCH_2(CH_2)_mCOOH$, —$RSO_2CH_2(CH_2)_mCH_3$, —$RPO_2$ $(OH)CH_2(CH_2)_mCH_3$ or —$RCOCH(NCOCH_3)CH_2CH_2$ $CONH_2$; and Y is OH or Cl to form the above compound of the formula I.

4. The process according to claim 3, wherein the compound of the formula I is selected from the group consisting of 2.2-[(2E,4E,6E,8E)-3,7-dimethyl-9-(2,6,6-trimethyl-cyclohex-1-enyl)-nona-2,4,6,8-tetraenoyl amino]-5-hydroxy-phenyl butanoate (KCBG10);

5-butyryloxy-2-[3,7-dimethyl-9-(2,6,6-trimethyl-cyclohex-1-enyl)-nona-2,4,6,8-tetraenoylamino]-phenyl butanoate (KCBG09);

2-[(2E,4E,6E,8E)-3,7-dimethyl-9-(2,6,6-trimethyl-cyclohex-1-enyl)-nona-2,4,6,8-tetraenoylamino]-5-hydroxy-phenyl propionate (KCBG15);

2-[(2E,4E,6E,8E)-3,7-dimethyl-9-(2,6,6-trimethyl-cyclohex-1-enyl)-nona-2,4,6,8-tetraenoylamino]-5-hydroxy-phenyl-2-oxo-propionate (KCBG22);

2-[(2E,4E,6E,8E)-3,7-dimethyl-9-(2,6,6-trimethyl-cyclohex-1-enyl)-nona-2,4,6,8-tetraenoylamino]-5-hydroxy-phenyl-(dimethylamino)-acetate (KCBG23);

4-(4-[(2E,4E,6E,8E)-3,7-dimethyl-9-(2,6,6-trimethyl-1-cyclohexenyl)-2,4,6,8-nonatetraenoyl]aminophenoxy)-4-oxobutanoic acid (KCBG32);

2-butyryloxy-5-(2E,4E,6E,8E)-[3,7-dimethyl-9-(2,6,6-trimethyl-cyclohex-1-enyl)-nona-2,4,6,8-tetraenoylamino]-phenyl butanoate (KCBG34);

5-(2E,4E,6E,8E)-[3,7-dimethyl-9-(2,6,6-trimethyl-cyclohex-1-enyl)-nona-2,4,6,8-tetraenoylamino]-2-hydroxy-phenyl butanoate (KCBG35);

2-[(2E,4E,6E,8E)-3,7-dimethyl-9-(2,6,6-trimethyl-cyclohex-1-enyl)-nona-2,4,6,8-tetraenoylamino]-5-hydroxy-phenyl-2-oxobutanoate (KCBG38);

2-[(2E,4E,6E,8E)-3,7-dimethyl-9-(2,6,6-trimethyl-cyclohex-1-enyl)-nona-2,4,6,8-tetraenoylamino]-5-hydroxy-phenyl-3-hydroxy-butanoate (KCBG39);

(2E,4E,6E,8E)-[3,7-dimethyl-9-(2,6,6-trimethyl-cyclohex-1-enyl)-nona-2,4,6,8-tetraenoylamino]-(4-butyrylamino)-phenylamide (KCBG40);

(2E,4E,6E,8E)-[3,7-dimethyl-9-(2,6,6-trimethyl-cyclohex-1-enyl)-nona-2,4,6,8-tetraenoylamino]-(3-butylamino-4-hydroxy)-phenylamide (KCBG41);

4-[(2E,4E,6E,8E)-3,7-dimethyl-9-(2,6,6-trimethyl-1-cyclohexenyl)-2,4,6,8-nonatetraenoyl]aminophenyl-1-butanesulfonate (KCBG43);

4-[(2E,4E,6E,8E)-3,7-dimethyl-9-(2,6,6-trimethyl-1-cyclohexenyl)-2,4,6,8-nonatetraenoyl]aminophenyl-2-oxopropanoate (KCBG45);

4-[(2E,4E,6E,8E)-3,7-dimethyl-9-(2,6,6-trimethyl-1-cyclohexenyl)-2,4,6,8-nonatetraenoyl]aminophenyl-2-oxobutanoate (KCBG47);

4-(4-[(2E,4E,6E,8E)-3,7-dimethyl-9-(2,6,6-trimethyl-1-cyclohexenyl)-2,4,6,8-nonatetraenoyl]aminophenoxy)-4-oxobutanoic acid (KCBG50);

4-(4-[(2E,4E,6E,8E)-3,7-dimethyl-9-(2,6,6-trimethyl-1-cyclohexenyl)-2,4,6,8-nonatetraenoyl]aminophenoxy)-oxo-hexandioic acid (KCBG51);

4-[(2E,4E,6E,8E)-3,7-dimethyl-9-(2,6,6-trimethyl-cyclohex-1-enyl)-nona-2,4,6,8-tetraenoylamino]-phenyl-2-acetylamino-4-carbamoyl-butanoate (KCBG52);

4-(4-[(2E,4E,6E,8E)-3,7-dimethyl-9-(2,6,6-trimethyl-1-cyclohexenyl)-2,4,6,8-nonatetraenoyl]aminophenoxy)-oxo-peptandioic acid (KCBG53); and 4-(4-[(2E,4E,6E,8E)-3,7-dimethyl-9-(2,6,6-trimethyl-1-cyclohexenyl)-2,4,6,8-nonatetraenoyl]aminophenoxy)-oxo-octandioic acid (KCBG54).

5. A process for producing a compound of the formula I:

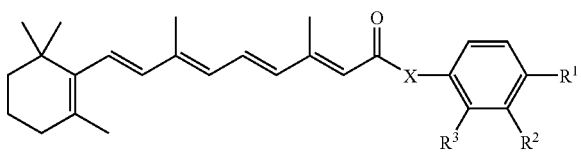

wherein
(i) X is O, NH or S; $R^1$ and $R^2$, which may be identical or different, are each independently —OH, —SH, —$NH_2$, —COOH, —$R(CH_2)_mCH_3$, —$RCOCO(CH_2)_m$ $CH_3$, —$RCO(CH_2)_mCHCH_3CH_3$, —$RCO(CH_2)_m$ $NR^4CH_3$, —$RCOCHOH(CH_2)_mCH_3$, —$RCOCH_2$ $(CH_2)_mCH_3$, —$RCOCH_2CHOH(CH_2)_mCH_3$, —$RCOCH_2(CH_2)_mCOOH$, —$RSO_2CH_2(CH_2)_mCH_3$, —$RPO_2(OH)CH_2(CH_2)_mCH_3$ or $RCOCH(NHCOCH_3)$ $CH_2CH_2CONH_2$, in which each R is $CH_2$, O, NH or S, $R^4$ is H or $C_1$–$C_6$ alkyl, and each m is an integer of 0 to 5; and $R^3$ is H, with the proviso that if X is O, $R^1$ and $R^2$, which may be identical or different, are not each independently —OH, —$NH_2$, —COOH, —$R(CH_2)_mCH_3$, wherein R is $CH_2$, NH or O, m is 0 to 5, —$RCO(CH_2)_m$ $CHCH_3CH_3$, wherein R is NH, m is 0 to 5, —$RCOCH_2(CH_2)_mCH_3$, wherein R is NH, m is 0 to 5, —$RCO(CH_2)_mNR^4CH_3$, wherein R is NH, m is 0, $R^4$ is H or $C_{1-6}$ alkyl, —$RSO_2CH_2(CH_2)_mCH_3$, wherein R is NH, m is 0 to 5;

(ii) X is the same as defined above; $R^1$ and $R^3$, which may be identical or different, are each independently —OH, —SH, —$NH_2$, —COOH, —$R(CH_2)_mCH_3$, —$RCOCO$ $(CH_2)_mCH_3$, —$RCO(CH_2)_mCHCH_3CH_3$, —$RCO$ $(CH_2)_mNR^4CH_3$, —$RCOCHOH(CH_2)_mCH_3$, —$RCOCH_2(CH_2)_mCH_3$, —$RCOCH_2CHOH(CH_2)_m$ $CH_3$, —$RCOCH_2(CH_2)_mCOOH$, —$RSO_2CH_2(CH_2)_m$ $CH_3$, —$RPO_2(OH)CH_2(CH_2)_mCH_3$ or $RCOCH(NH-COCH_3)CH_2CH_2CONH_2$, in which each R is $CH_2$, O, NH or S, $R^4$ is H or $C_1$–$C_6$ alkyl, and each m is an integer of 0 to 5; and $R^2$ is H, with the proviso that if X is O, $R^1$ and $R^3$, which may be identical or different, are not each independently —OH, —$NH_2$, —COOH, —$R(CH_2)_mCH_3$, wherein R is $CH_2$, NH or O, m is 0 to 5, —$RCO(CH_2)_m$ $CHCH_3CH_3$, wherein R is NH, m is 0 to 5, —$RCOCH_2(CH_2)_mCH_3$ wherein R is NH, m is 0 to 5, —$RCO(CH_2)_mNR^4CH_3$, wherein R is NH, m is 0, $R^4$ is H or $C_{1-6}$ alkyl, —$RSO_2CH_2(CH_2)_mCH_3$, wherein R is NH, m is 0 to 5;

(iii) X is the same as defined above; $R^1$ is —OH, —SH, —$NH_2$, —COOH, —$R(CH_2)_mCH_3$, —$RCOCO(CH_2)_m$ $CH_3$, —$RCO(CH_2)_mCHCH_3CH_3$, —$RCO(CH_2)_m$ $NR^4CH_3$, —$RCOCHOH(CH_2)_mCH_3$, —$RCOCH_2$ $(CH_2)_mCH_3$, —$RCOCH_2CHOH(CH_2)_mCH_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each R is CH$_2$, O, NH or S, R$^4$ is H or C$_1$–C$_6$ alkyl, and each m is an integer of 0 to 5; R$^2$ is H; and R$^3$ is H, OH or Cl, with the proviso that when R$^2$ and R$^3$ are H, (a) if X is NH, R$^1$ is not —RCO(CH$_2$)$_m$CHCH$_3$CH$_3$, wherein R is O, m is 0 to 5, —RCOCH$_2$(CH$_2$)$_m$CH$_3$, wherein R is O, m is 0 to 5, —OH, —COOH, or —R(CH$_2$)$_m$CH$_3$, wherein R is O, m is 0 or 1, (b) if X is O, R$^1$ is not —RCO(CH$_2$)$_m$CHCH$_3$CH$_3$, wherein R is NH, m is 0 to 2, —RCOCH$_2$(CH$_2$)$_m$CH$_3$, wherein R is NH, m is 0 to 2, —R(CH$_2$)$_m$CH$_3$, wherein R is Ch$_2$, O or NH, m is 0 to 5, —COOH, —NH$_2$, —OH, —RCO(CH$_2$)$_m$NR$^4$CH$_3$, wherein R is O or NH, m is 0, R$^4$ is H or C$_{1-6}$ alkyl, —RSO$_2$CH$_2$(CH$_2$)$_m$CH$_3$, wherein R is NH, m is 0 to 5

(c) if X is S, R$^1$ is not —RCO(CH$_2$)$_m$CHCH$_3$CH$_3$, wherein R is NH, m is 0 to 2, —RCOCH$_2$(CH$_2$)$_m$CH$_3$, wherein R is NH, m is 0 to 2;

(iv) X is the same as defined above; R$^3$ is —OH, —SH, —NH$_2$, —COOH, —R(CH$_2$)$_m$CH$_3$, —RCOCO(CH$_2$)$_m$CH$_3$, RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each R is CH$^2$, O, NH or S, R$^4$ is H or C$_1$–C$_6$ alkyl, and each m is an integer of 0 to 5; R$^2$ is H; and R$^1$ is H, OH or Cl, with the proviso that when R$^1$ and R$^2$ are H, (a) if X is NH, R$^3$ is not COOH, (b) if X is S, R$^3$ is not —RCO(CH$_2$)$_m$CHCH$_3$CH$_3$, wherein R is NH, m is 0 to 2, —RCOCH$_2$(CH$_2$)$_m$CH$_3$, wherein R is NH, m is 0 to 2, (c) if X is O, R$^3$ is not —RCO(CH$_2$)$_m$CHCH$_3$CH$_3$, wherein R is NH, m is 0 to 2, —RCOCH$_2$(CH$_2$)$_m$CH$_3$, wherein R is NH, m is 0 to 2, —R(CH$_2$)$_m$CH$_3$, wherein R is CH$_2$, O or NH, m is 0 to 5, —COOH, —NH$_2$, —OH, —RCO(CH$_2$)$_m$NR$^4$CH$_3$, wherein R is O or NH, m is 0, R$^4$ is H or C$_{1-6}$ alkyl, —RSO$_2$CH$_2$(CH$_2$)$_m$CH$_3$, wherein R is NH, m is 0 to 5; or (v) X is the same as defined above; R$^1$, R$^2$ and R$^3$, which may be identical or different, are each independently —OH, —SH, —NH$_2$, —COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each R is CH$_2$, O, NH or S, R$^4$ is H or C$_1$–C$_6$ alkyl, and each m is an integer of 0 to 5, with the proviso that if X is O, R$^1$, R$^2$ and R$^3$, which may be identical or different, are not each independently —OH, —NH$_2$, —COOH, —R(CH$_2$)$_m$CH$_3$, wherein R is CH$_2$, NH or O, m is 0 to 5), —RCO(CH$_2$)$_m$CHCH$_3$CH$_3$, wherein R is NH, m is 0 to 5, —RCOCH$_2$(CH$_2$)$_m$CH$_3$, wherein R is NH, m is 0 to 5, —RCO(CH$_2$)$_m$NR$^4$CH$_3$, wherein R is O or NH, m is 0, R$^4$ is H or C$_{1-6}$ alkyl, —RSO$_2$CH$_2$(CH$_2$)$_m$CH$_3$, wherein R is NH, m is 0 to 5; or pharmaceutically acceptable salts thereof, which comprises reacting a compound of the formula II:

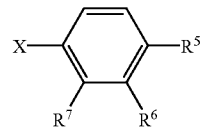

(II)

wherein X is the same as defined above; and R$^5$ and R$^6$ are each independently OH, NH$_2$ or SH and R$^7$ is H or Cl for the preparation of the above class (i) of the compounds of the formula I; R$^5$ and R$^7$ are each independently OH, NH$_2$ or SH and R$^6$ is H for the preparation of the above class (ii) of the compounds of the formula I; R$^5$ is OH, NH$_2$ or SH, R$^6$ is H and R$^7$ is H, OH or Cl for the preparation of the above class (iii) of the compounds of the formula I; R$^5$ is H, OH or Cl, R$^6$ is H and R$^7$ is OH, NH$_2$ or SH for the preparation of the above class (iv) of the compounds of the formula I; or R$^5$, R$^6$ and R$^7$ are each independently OH, NH$_2$ or SH for the preparation of the above class (v) of the compounds of the formula I with a compound of the formula IV:

W—Y (IV)

wherein W is —OH, —SH, —NH$_2$, —COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or —RCOCH(NCOCH$_3$)CH$_2$CH$_2$ CONH$_2$; and Y is OH or Cl to form a compound of the formula V:

(V)

wherein X, R$^1$, R$^2$ and R$^3$ are the same as defined above and reacting the compound of the formula V with retinoic acid to form the above compound of the formula I.

6. The process according to claim 5, wherein the compound of the formula I is selected from the group consisting of 2.2-[(2E,4E,6E,8E)-3,7-dimethyl-9-(2,6,6-trimethyl-cyclohex-1-enyl)-nona-2,4,6,8-tetraenoylamino]-5-hydroxy-phenyl butanoate (KCBG10);

5-butyryloxy-2-[3,7-dimethyl-9-(2,6,6-trimethyl-cyclohex-1-enyl)-nona-2,4,6,8-tetraenoylamino]-phenyl butanoate (KCBG09);

2-[(2E,4E,6E,8E)-3,7-dimethyl-9-(2,6,6-trimethyl-cyclohex-1-enyl)-nona-2,4,6,8-tetraenoylamino]-5-hydroxy-phenyl propionate (KCBG15);

2-[(2E,4E,6E,8E)-3,7-dimethyl-9-(2,6,6-trimethyl-cyclohex-1-enyl)-nona-2,4,6,8-tetraenoylamino]-5-hydroxy-phenyl-2-oxo-propionate (KCBG22);

2-[(2E,4E,6E,8E)-3,7-dimethyl-9-(2,6,6-trimethyl-cyclohex-1-enyl)-nona-2,4,6,8-tetraenoylamino]-5-hydroxy-phenyl-(dimethylamino)-acetate (KCBG23);

4-(4-[(2E,4E,6E,8E)-3,7-dimethyl-9-(2,6,6-trimethyl-1-cyclohexenyl)-2,4,6,8-nonatetraenoyl]aminophenoxy)-4-oxobutanoic acid (KCBG32);

2-butyryloxy-5-(2E,4E,6E,8E)-[3,7-dimethyl-9-(2,6,6-trimethyl-cyclohex-1-enyl)-nona-2,4,6,8-tetraenoylamino]-phenyl butanoate (KCBG34);

5-(2E,4E,6E,8E)-[3,7-dimethyl-9-(2,6,6-trimethyl-cyclohex-1-enyl)-nona-2,4,6,8-tetraenoylamino]-2-hydroxy-phenyl butanoate (KCBG35);

2-[(2E,4E,6E,8E)-3,7-dimethyl-9-(2,6,6-trimethyl-cyclohex-1-enyl)-nona-2,4,6,8-tetraenoylamino]-5-hydroxy-phenyl-2-oxobutanoate (KCBG38);

2-[(2E,4E,6E,8E)-3,7-dimethyl-9-(2,6,6-trimethyl-cyclohex-1-enyl)-nona-2,4,6,8-tetraenoylamino]-5-hydroxy-phenyl-3-hydroxy-butanoate (KCBG39);

(2E,4E,6E,8E)-[3,7-dimethyl-9-(2,6,6-trimethyl-cyclohex-1-enyl)-nona-2,4,6,8-tetraenoylamino]-(4-butyrylamino)-phenylamide (KCBG40);

(2E,4E,6E,8E)-[3,7-dimethyl-9-(2,6,6-trimethyl-cyclohex-1-enyl)-nona-2,4,6,8-tetraenoylamino]-(3-butylamino-4-hydroxy)-phenylamide (KCBG41);

4-[(2E,4E,6E,8E)-3,7-dimethyl-9-(2,6,6-trimethyl-1-cyclohexenyl)-2,4,6,8-nonatetraenoyl]aminophenyl-1-butanesulfonate (KCBG43);

4-[(2E,4E,6E,8E)-3,7-dimethyl-9-(2,6,6-trimethyl-1-cyclohexenyl)-2,4,6,8-nonatetraenoyl]aminophenyl-2-oxopropanoate (KCBG45);

4-[(2E,4E,6E,8E)-3,7-dimethyl-9-(2,6,6-trimethyl-1-cyclohexenyl)-2,4,6,8-nonatetraenoyl]aminophenyl-2-oxobutanoate (KCBG47);

4-(4-[(2E,4E,6E,8E)-3,7-dimethyl-9-(2,6,6-trimethyl-1-cyclohexenyl)-2,4,6,8-nonatetraenoyl]aminophenoxy)-4-oxobutanoic acid (KCBG50);

4-(4-[(2E,4E,6E,8E)-3,7-dimethyl-9-(2,6,6-trimethyl-1-cyclohexenyl)-2,4,6,8-nonatetraenoyl]aminophenoxy)-oxo-hexandioic acid (KCBG51);

4[(2E,4E,6E,8E)-3,7-dimethyl-9-(2,6,6-trimethyl-cyclohex-1-enyl)-nona-2,4,6,8-tetraenoylamino]-phenyl-2-acetylamino-4-carbamoyl-butanoate (KCBG52);

4-(4-[(2E,4E,6E,8E)-3,7-dimethyl-9-(2,6,6-trimethyl-1-cyclohexenyl)-2,4,6,8-nonatetraenoyl]aminophenoxy)-oxo-peptandioic acid (KCBG53); and 4-(4-[(2E,4E,6E,8E)-3,7-dimethyl-9-(2,6,6-trimethyl-1-cyclohexenyl)-2,4,6,8-nonatetraenoyl]aminophenoxy)-oxo-octadionic acid (KCBG54).

7. A process for producing a compound of the formula Ia:

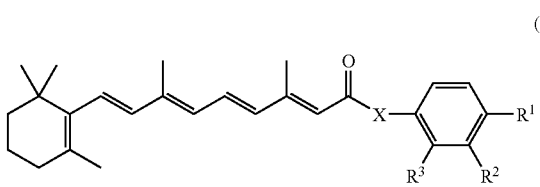

(Ia)

wherein
X is O, NH or S; $R^1$ and $R^3$ are each independently —OH, —SH, —NH$_2$, —COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each $R^1$ is O, NH or S, $R^4$ is H or $C_1$–$C_6$ alkyl, and each m is an integer of 0 to 5; $R^2$ is H, wherein $R^1$ and $R^3$ are not simultaneously —OH, —SH, —NH, or —COOH, with the proviso that if X is O, $R^1$ and $R^3$, which may be identical or different are not each independently —OH, —NH$_2$, —COOH, —R(CH$_2$)$_m$CH$_3$, wherein R is CH$_2$, NH or O, m is 0 to 5, —RCO(CH$_2$)$_m$CHCH$_3$CH$_3$, wherein R is NH, m is 0 to 5, —RCOCH$_2$(CN$_2$)$_m$CH$_3$ wherein R is NH, m is 0 to 5, —RCO(CH$_2$)$_m$NR$^4$CH$_3$, wherein R is NH, m is 0, $R^4$ is H or $C_{1-6}$ alkyl, —RSO$_2$CH$_2$(CH$_2$)$_m$CH$_3$, wherein R is NH, m is 0 to 5, which comprises reacting a compound of the formula IIIa:

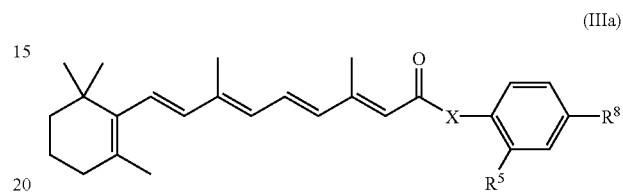

(IIIa)

wherein $R^5$ is OH, NH$_2$ or SH; and $R^8$ is OH or SH with a compound of the formula IV:

W—Y (IV)

wherein W is —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$ CH$_3$, —RCOCH$_2$(CH$_2$)$_m$CH$_3$, —RCOCH$_2$CHOH(CH$_2$)$_m$ CH$_3$, —RCOCH$_2$(CH$_2$)$_m$COOH, or RCOCH(NH-COCH$_3$)CH$_2$CH$_2$CONH$_2$, and Y is OH or Cl and deesterifying the resulting material to yield the above compound of the formula Ia.

8. A process for producing a compound of the formula Ic:

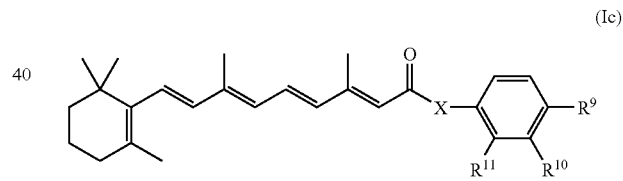

(Ic)

which comprises reacting a compound of the formula IIa:

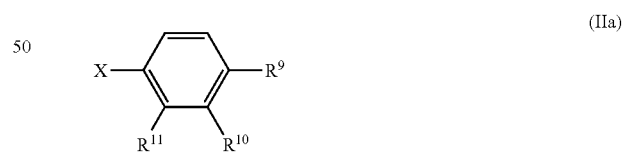

(IIa)

wherein X is O, NH or S; $R^9$ and $R^{10}$ are each independently —R(CH$_2$)$_m$CH$_3$ and $R^{11}$ is H; $R^9$ and $R^{11}$ are each independently —R(CH$_2$)$_m$CH$_3$ and $R^{10}$ is H; $R^9$ is —R(CH$_2$)$_m$CH$_3$, $R^{10}$ is H and $R^{11}$ is H, OH or Cl; $R^9$ is H, OH or Cl, $R^{10}$ is H and $R^{11}$ is —R(CH$_2$)$_m$CH$_3$; or $R^9$, $R^{10}$ and $R^{11}$ are each independently —R(CH$_2$)$_m$CH$_3$, in which each R is CH$_2$, O, NH or S and each m is an integer of 0 to 5 with retinoic acid to yield the above compound of the formula Ic.

9. An anti-cancer composition comprising a therapeutically effective amount of the compound of the formula I and a pharmaceutically acceptable carrier thereof:

(I)

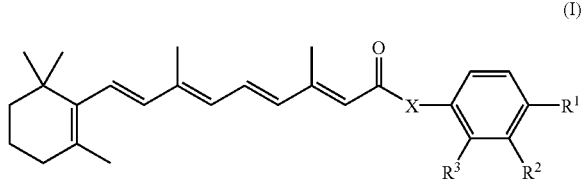

wherein (i) X is O, NH or S; R¹ and R², which may be identical or different, are each independently —OH, —SN, —NH₂, —COOH, —R(CH₂)ₘCH₃, —RCOCO(CH₂)ₘCH₃, —RCO(CH₂)ₘCHCH₃CH₃, —RCO(CH₂)ₘNR⁴CH₃, —RCOCHOH(CH₂)ₘCH₃, —RCOCH₂(CH₂)ₘCH₃, —RCOCH₂CHOH(CH₂)ₘCH₃, —RCOCH₂(CH₂)ₘCOOH, —RSO₂CH₂(CH₂)ₘCH₃, —RPO₂(OH)CH₂(CH₂)ₘCH₃ or RCOCH(NHCOCH₃)CH₂CH₂CONH₂, in which each R¹ is CH₂, O, NH or S, R⁴ is H or C₁–C₆ alkyl, and each m is an integer of 0 to 5; and R³ is H, (ii) X is the same as defined above; R¹ and R³, which may be identical or different, are each independently —OH, —SH, —NH₂, —COOH, —R(CH₂)ₘCH₃, —RCOCO(CH₂)ₘCH₃, —RCO(CH₂)ₘCHCH₃CH₃, —RCO(CH₂)ₘNR⁴CH₃, —RCOCHOH(CH₂)ₘCH₃—RCOCH₂(CH₂)ₘCH₃, —RCOCH₂CHOH(CH₂)ₘCH₃, —RCOCH₂(CH₂)ₘCOOH, —RSO₂CH₂(CH₂)ₘCH₃, —RPO₂(OH)CH₂(CH₂)ₘCH₃ or RCOCH(NHCOCH₃)CH₂CH₂CONH₂, in which each R is CH₂, O, NH or S, R⁴ is H or C₁–C₆ alkyl, and each m is an integer of 0 to 5; and R² is H, (iii) X is the same as defined above; R¹ is —OH, —SH, —NH₂, —COOH, —R(CH₂)ₘCH₃, —RCOCO(CH₂)ₘCH₃, —RCO(CH₂)ₘCHCH₃CH₃, —RCO(CH₂)ₘNR⁴CH₃, —RCOCHOH(CH₂)ₘCH₃, —RCOCH₂(CH₂)ₘCH₃, —RCOCH₂CHOH(CH₂)ₘCH₃, —RCOCH₂(CH₂)ₘCOOH, —RSO₂CH₂(CH₂)ₘCH₃, —RPO₂(OH)CH₂(CH₂)ₘCH₃ or RCOCH(NHCOCH₃)CH₂CH₂CONH₂, in which each R is CH₂, O, NH or S, R⁴ is H or C₁–C₆ alkyl, and each m is an integer of 0 to 5; R² is H; and R³ is H, OH or Cl, with the proviso that when R² and R³ are H, if X is NH, R¹ is not —RCOCH₂(CH₂)ₘCH₃, wherein R is O, m is 0 to 5, (iv) X is the same as defined above; R³ is —OH, —SH, —NH₂, —COOH, —R(CH₂)ₘCH₃, —RCOCO(CH₂)ₘCH₃, —RCO(CH₂)ₘCHCH₃CH₃, —RCO(CH₂)ₘNR⁴CH₃, —RCOCHOH(CH₂)ₘCH₃, —RCOCH₂(CH₂)ₘCH₃, —RCOCH₂CHOH(CH₂)ₘCH₃, —RCOCH₂(CH₂)ₘCOOH, —RSO₂CH₂(CH₂)ₘCH₃, —RPO₂(OH)CH₂(CH₂)ₘCH₃ or RCOCH(NHCOCH₃)CH₂CH₂CONH₂, in which each R is CH₂, O, NH or S, R⁴ is H or C₁–C₆ alkyl, and each m is an integer of 0 to 5; R² is H; and R¹ is H, OH or Cl, (v) X is the same as defined above; R¹, R² and R³, which may be identical or different, are each independently —OH, —SH, —NH₂, —COOH, —R(CH₂)ₘCH₃, —RCOCO(CH₂)ₘCH₃, —RCO(CH₂)ₘCHCH₃CH₃, —RCO(CH₂)ₘNR⁴CH₃, —RCOCHOH(CH₂)ₘCH₃, —RCOCH₂(CH₂)ₘCH₃, —RCOCH₂CHOH(CH₂)ₘCH₃, —RCOCH₂(CH₂)ₘCOOH, —RSO₂CH₂(CH₂)ₘCH₃, —RPO₂(OH)CH₂(CH₂)ₘCH₃ or RCOCH(NHCOCH₃)CH₂CH₂CONH₂, in which each R is CH₂, O, NH or S, R⁴ is H or C₁–C₆ alkyl, and each m is an integer of 0 to 5.

10. The composition according to claim 9, wherein the compound of the formula I is selected from the group consisting of 2.2-[(2E,4E,6E,8E)-3,7-dimethyl-9-(2,6,6-trimethyl-cyclohex-1-enyl)-nona-2,4,6,8-tetraenoyl amino]-5-hydroxy-phenyl butanoate (KCBG10);

5-butyryloxy-2-[3,7-dimethyl-9-(2,6,6-trimethyl-cyclohex-1-enyl)-nona-2,4,6,8-tetraenoylamino]-phenyl butanoate (KCBG09);

2-[(2E,4E,6E,8E)-3,7-dimethyl-9-(2,6,6-trimethyl-cyclohex-1-enyl)-nona-2,4,6,8-tetraenoylamino]-5-hydroxy-phenyl propionate (KCBG15);

2-[(2E,4E,6E,8E)-3,7-dimethyl-9-(2,6,6-trimethyl-cyclohex-1-enyl)-nona-2,4,6,8-tetraenoylamino]-5-hydroxy-phenyl-2-oxo-propionate (KCBG22);

2-[(2E,4E,6E,8E)-3,7-dimethyl-9-(2,6,6-trimethyl-cyclohex-1-enyl)-nona-2,4,6,8-tetraenoylamino]-5-hydroxy-phenyl-(dimethylamino)-acetate (KCBG23);

4-(4-[(2E,4E,6E,8E)-3,7-dimethyl-9-(2,6,6-trimethyl-1-cyclohexenyl)-2,4,6,8-nonatetraenoyl]aminophenoxy)-4-oxobutanoic acid (KCBG32);

2-butyryloxy-5-(2E,4E,6E,8E)-[3,7-dimethyl-9-(2,6,6-trimethyl-cyclohex-1-enyl)-nona-2,4,6,8-tetraenoylamino]-phenyl butanoate (KCBG34);

5-(2E,4E,6E,8E)-[3,7-dimethyl-9-(2,6,6-trimethyl-cyclohex-1-enyl)-nona-2,4,6,8-tetraenoylamino]-2-hydroxy-phenyl butanoate (KCBG35);

2-[(2E,4E,6E,8E)-3,7-dimethyl-9-(2,6,6-trimethyl-cyclohex-1-enyl)-nona-2,4,6,8-tetraenoylamino]-5-hydroxy-phenyl-2-oxobutanoate (KCBG38);

2-[(2E,4E,6E,8E)-3,7-dimethyl-9-(2,6,6-trimethyl-cyclohex-1-enyl)-nona-2,4,6,8-tetraenoylamino]-5-hydroxy-phenyl-3-hydroxy-butanoate (KCBG39);

(2E,4E,6E,8E)-[3,7-dimethyl-9-(2,6,6-trimethyl-cyclohex-1-enyl)-nona-2,4,6,8-tetraenoylamino]-(4-butyrylamino)-phenylamide (KCBG40);

(2E,4E,6E,8E)-[3,7-dimethyl-9-(2,6,6-trimethyl-cyclohex-1-enyl)-nona-2,4,6,8-tetraenoylamino]-(3-butylamino-4-hydroxy)-phenylamide (KCBG41);

4-[(2E,4E,6E,8E)-3,7-dimethyl-9-(2,6,6-trimethyl-1-cyclohexenyl)-2,4,6,8-nonatetraenoyl]aminophenyl-1-butanesulfonate (KCBG43);

4-[(2E,4E,6E,8E)-3,7-dimethyl-9-(2,6,6-trimethyl-1-cyclohexenyl)-2,4,6,8-nonatetraenoyl]aminophenyl-2-oxopropanoate (KCBG45);

4-[(2E,4E,6E,8E)-3,7-dimethyl-9-(2,6,6-trimethyl-1-cyclohexenyl)-2,4,6,8-nonatetraenoyl]aminophenyl-2-oxobutanoate (KCBG47);

4-(4-[(2E,4E,6E,8E)-3,7-dimethyl-9-(2,6,6-trimethyl-1-cyclohexenyl)-2,4,6,8-nonatetraenoyl]aminophenoxy)-4-oxobutanoic acid (KCBG50);

4-(4-[(2E,4E,6E,8E)-3,7-dimethyl-9-(2,6,6-trimethyl-1-cyclohexenyl)-2,4,6,8-nonatetraenoyl]aminophenoxy)-oxo-hexandioic acid (KCBG51);

4-[(2E,4E,6E,8E)-3,7-dimethyl-9-(2,6,6-trimethyl-cyclohex-1-enyl)-nona-2,4,6,8-tetraenoylamino]-phenyl-2-acetylamino-4-carbamoyl-butanoate (KCBG52);

4-(4-[(2E,4E,6E,8E)-3,7-dimethyl-9-(2,6,6-trimethyl-1-cyclohexenyl)-2,4,6,8-nonatetraenoyl]aminophenoxy)-oxo-peptandioic acid (KCBG53); and 4-(4-[(2E,4E,6E,8E)-3,7-dimethyl-9-(2,6,6-trimethyl-1-cyclohexenyl)-2,4,6,8-nonatetraenoyl]aminophenoxy)-oxo-octadionic acid (KCBG54).

11. A compound of the formula V:

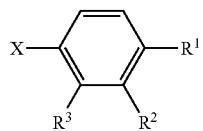

wherein (i) X is OH, NH$_2$ or SH; R$^1$ and R$^2$, which may be identical or different, are each independently —OH, —SH, —NH$_2$, —COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each R is CH$_2$, O, NH or S, R$^4$ is H or C$_1$–C$_6$ alkyl, and each m is an integer of 0 to 5; and R$^3$ is H;

with the proviso that (a) if X is NH$_2$, R$^1$ and R$_2$, which may be identical or different, are not each independently —OH, —R(CH$_2$)$_m$CH$_3$, wherein R is O or CH$_2$, m is 0 to 5, (b) if X is OH and R$_1$ is OH, R$^2$ is not —RSO$_2$CH$_2$(CH$_2$)$_m$CH$_3$, wherein R is NH, m is 0 to 5 or —R(CH$_2$)$_m$CH$_3$, wherein R is CH$_2$, m is 0 to 5, (c) if X is OH and R$^3$ is OH, R$^1$ is not —RSO$_2$CH$_2$(CH$_2$)$_m$CH$_3$, wherein R is NH, m is 0 to 5 or —R(CH$_2$)$_m$CH$_3$, wherein R is CH$_2$, m is 0 to 5;

(ii) X is the same as defined above; R$^1$ and R$^3$, which may be identical or different, are each independently —OH, —SH, —NH$_2$, —COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each R is CH$_2$, O, NH or S, R$^4$ is H or C$_1$–C$_6$ alkyl, and each m is an integer of 0 to 5; and R$^2$ is H;

with a proviso that (a) if X is NH$_2$, R$^1$ and R$^3$, which may be identical or different, are not each independently —OH, —R(CH$_2$)$_m$CH$_3$, wherein R is O or CH$_2$, m is 0 to 5, (b) if X is NH$_2$ and R$^1$ is OH, R$^3$ is not —RSO$_2$CH$_2$(CH$_2$)$_m$CH$_3$, wherein R is NH, m is 0 to 5, (c) if X is OH and R$^1$ is OH, R$^3$ is not —RSO$_2$CH$_2$(CH$_2$)$_m$CH$_3$, wherein R is NH, m is 0 to 5 or —R(CH$_2$)$_m$CH$_3$, wherein R is CH$_2$, m is 0 to 5, (d) if X is OH and R$^3$ is OH, R$^1$ is not —RSO$_2$CH$_2$(CH$_2$)$_m$CH$_3$, wherein R is NH, m is 0 to 5;

(iii) X is the same as defined above; R$^1$ is —OH, —SH, —NH$_2$, —COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each R is CH$_2$, O, NH or S, R$^4$ is H or C$_1$–C$_6$ alkyl, and each m is an integer of 0 to 5; R$^2$ is H; and R$^3$ is H, OH or Cl;

with the proviso that (a) if X is NH$_2$, R$^1$ is not —OH, —NH$_2$, —R(CH$_2$)$_m$CH$_3$, wherein R is O or CH$_2$, m is 0 to 5, (b) if X is OH and R$^1$ is —RSO$_2$CH$_2$(CH$_2$)$_m$CH$_3$, wherein R is NH, m is 0 to 5, R$^3$ is not —OH;

(iv) X is the same as defined above; R$^3$ is —OH, —SH, —NH$_2$, —COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$—RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each R is CH$_2$, O, NH or S, R$^4$ is H or —C$_1$–C$_6$ alkyl, and each m is an integer of 0 to 5; R$^2$ is H; and R$^1$ is H, OH or Cl;

with the proviso that (a) if X is NH$_2$, R$^3$ is not —OH, —NH$_2$, or —R(CH$_2$)$_m$CH$_3$, wherein R is O or CH$_2$, m is 0 to 5, (b) if X is NH$_2$ and R$^3$ is NH$_2$, R$^1$ is not Cl or H, (c) if X is OH, R$^1$ is OH and R$^2$ is H, R$^3$ is not —RSO$_2$CH$_2$(CH$_2$)$_m$CH$_3$, wherein R is NH, m is 0 to 5 ; or (v) X is the same as defined above; R$^1$, R$^2$ and R$^3$, which may be identical or different, are each independently —OH, —SH, —NH$_2$, —COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each R is CH$_2$, O, NH or S, R$^4$ is H or C$_1$–C$_6$ alkyl, and each m is an integer of 0 to 5, with the proviso that when X is OH, (a) if R$^1$ is —R(CH$_2$)$_m$CH$_3$, wherein R is CH$_2$, m is 0 to 5 and R$^2$ is —RSO$_2$CH$_2$(CH$_2$)$_m$CH$_3$, wherein R is NH, m is 0 to 5, R$^3$ is not OH, (b) if R$^1$ is —RSO$_2$CH$_2$(CH$_2$)$_m$CH$_3$, wherein R is NH, m is 0 to 5 and R$^2$ is OH, R$^3$ is not OH or —R(CH$_2$)$_m$CH$_3$, wherein R is CH$_2$, m is 0 to 5, (c) if R$^1$ is OH and R$^2$ is —RSO$_2$CH$_2$(CH$_2$)$_m$CH$_3$, wherein R is NH, m is 0 to 5, R$^3$ is not OH, —(CH$_2$)$_m$CH$_3$, wherein R is NH, m is 0 to 5 or —RSO$_2$CH$_2$(CH$_2$)$_m$CH$_3$, wherein R is NH, m is 0 to 5, (d) if R$^1$ is OH and —R$^2$ is R(CH$_2$)$_m$CH$_3$, wherein R is CH$_2$, m is 0 to 5, R$^3$ is not —RSO$_2$CH$_2$(CH$_2$)$_m$CH$_3$, wherein R is NH, m is 0 to 5, (e) if R$^1$ is —R(CH$_2$)$_m$CH$_3$, wherein R is CH$_2$, m is 0 to 5 and R$^2$ is OH, R$^3$ is not —RSO$_2$CH$_2$(CH$_2$)$_m$CH$_3$, wherein R is NH, m is 0 to 5, (f) if R$^1$ is —RSO$_2$CH$_2$(CH$_2$)$_m$CH$_3$, wherein R is NH, m is 0 to 5 and R$^2$ is —R(CH$_2$)$_m$CH$_3$, wherein R is CH$_2$, m is 0 to 5, R$^3$ is not OH.

12. A compound of the formula I:

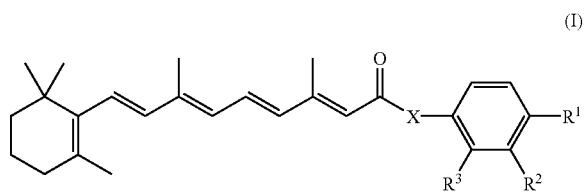

wherein

X is O, NH or S; $R^1$ and $R^3$, which may be identical or different, are each independently —OH, —SH, —NH$_2$, —COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each R is CH$_2$, O, NH or S, $R^4$ is H or C$_1$–C$_6$ alkyl, and each m is an integer of 0 to 5; and $R^2$ is H, with the proviso that if X is O, $R^1$ and $R^3$, which may be identical or different, are not each independently —OH, —NH$_2$, —COOH, —R(CH$_2$)$_m$CH$_3$, wherein R is CH$_2$, NH or O, m is 0 to 5, —RCO(CH$_2$)$_m$CHCH$_3$CH$_3$, wherein R is NH, m is 0 to 5, —RCOCH$_2$(CH$_2$)$_m$CH$_3$ wherein R is NH, m is 0 to 5, —RCO(CH$_2$)$_m$NR$^4$CH$_3$, wherein R is NH, m is 0, $R^4$ is H or C$_{1-6}$ alkyl, —RSO$_2$CH$_2$(CH$_2$)$_m$CH$_3$, wherein R is NH, m is 0 to 5; or pharmaceutically acceptable salts thereof.

13. A compound of the formula I:

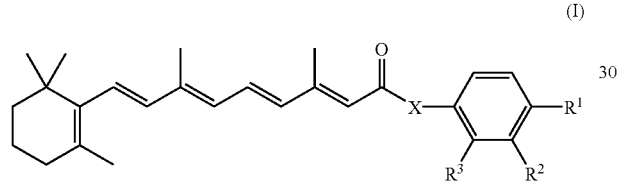

(I)

wherein

X is O, NH or S; $R^1$ is —OH, —SH, —NH$_2$, —COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each R is CH$_2$, O, NH or S, $R^4$ is H or C$_1$–C$_6$ alkyl, and each m is an integer of 0 to 5; $R^2$ is H; and $R^3$ is H, OH or Cl, with the proviso that when $R^2$ and $R^3$ are H, (a) if X is NH, $R^1$ is not —OH, —COOH, —RCO(CH$_2$)$_m$CHCH$_3$CH$_3$, wherein R is O, m is 0 to 5, —RCOCH$_2$(CH$_2$)$_m$CH$_3$, wherein R is O, m is 0 to 5, or —R(CH$_2$)$_m$CH$_3$, wherein R is O, m is 0 or 1, (b) if X is O, $R^1$ is not —COOH, —NH$_2$, —OH, —RCO(CH$_2$)$_m$CHCH$_3$CH$_3$, wherein R is NH, m is 0 to 2, —RCOCH$_2$(CH$_2$)$_m$CH$_3$, wherein R is NH, m is 0 to 2, —R(CH$_2$)$_m$CH$_3$, wherein R is CH$_2$, O or NH, m is 0 to 5, —RCO(CH$_2$)$_m$NR$^4$CH$_3$, wherein R is O or NH, m is 0, $R^4$ is H or C$_{1-6}$ alkyl, —RSO$_2$CH$_2$(CH$_2$)$_m$CH$_3$, wherein R is NH, m is 0 to 5, (c) if X is S, $R^1$ is not —RCO(CH$_2$)$_m$CHCH$_3$CH$_3$, wherein R is NH, m is 0 to 2, —RCOCH$_2$(CH$_2$)$_m$CH$_3$, wherein R is NH, m is 0 to 2; or pharmaceutically acceptable salts thereof.

14. A compound of the formula I:

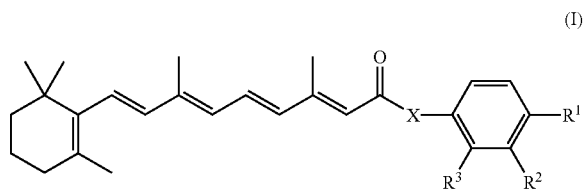

(I)

wherein

X is O, NH or S; $R^3$ is —OH, —SH, NH$_2$, —COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each R is CH$_2$, O, NH or S, $R^4$ is H or C$_1$–C$_6$ alkyl, and each m is an integer of 0 to 5; $R^2$ is H; and $R^1$ is H, OH or Cl, with the proviso that when $R^1$ and $R^2$ are H, (a) if X is NH, $R^3$ is not COOH, (b) if X is S, $R^3$ is not —RCO(CH$_2$)$_m$CHCH$_3$CH$_3$, wherein R is NH, m is 0 to 2, —RCOCH$_2$(CH$_2$)$_m$CH$_3$, wherein R is NH, m is 0 to 2, (c) if X is O, $R^3$ is not —COOH, —NH$_2$, —OH, —RCO(CH$_2$)$_m$CHCH$_3$CH$_3$, wherein R is NH, m is 0 to 2, —RCOCH$_2$(CH$_2$)$_m$CH$_3$, wherein R is NH, m is 0 to 2, —R(CH$_2$)$_m$CH$_3$, wherein R is CH$_2$, O or NH, m is 0 to 5, —RCO(CH$_2$)$_m$NR$^4$CH$_3$, wherein R is O or NH, m is 0, $R^4$ is H or C$_{1-6}$ alkyl, —RSO$_2$CH$_2$(CH$_2$)$_m$CH$_3$, wherein R is NH, m is 0 to 5; or pharmaceutically acceptable salts thereof.

15. A compound of the formula I:

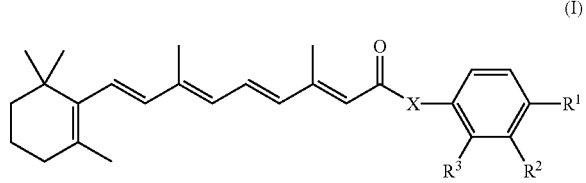

(I)

wherein

X is O, NH or S; $R^1$, $R^2$ and $R^3$, which may be identical or different, are each independently —OH, —SH, —NH$_2$, —COOH, —R(CH$_2$)$_m$CH$_3$, —RCOCO(CH$_2$)$_m$CH$_3$, —RCO(CH$_2$)$_m$CHCH$_3$CH$_3$, —RCO(CH$_2$)$_m$NR$^4$CH$_3$, —RCOCHOH(CH$_2$)$_m$CH$_3$, —RCOCH$_2$(CH$_2$)$_m$CH$_3$, —RCOCH$_2$CHOH(CH$_2$)$_m$CH$_3$, —RCOCH$_2$(CH$_2$)$_m$COOH, —RSO$_2$CH$_2$(CH$_2$)$_m$CH$_3$, —RPO$_2$(OH)CH$_2$(CH$_2$)$_m$CH$_3$ or RCOCH(NHCOCH$_3$)CH$_2$CH$_2$CONH$_2$, in which each R is CH$_2$, O, NH or S, $R^4$ is H or C$_1$–C$_6$ alkyl, and each m is an integer of 0 to 5, with the proviso that if X is O, $R^1$, $R^2$ and $R^3$, which may be identical or different, are not each independently —OH, —NH$_2$, —COOH, —R(CH$_2$)$_m$CH$_3$, wherein R is CH$_2$, NH or O, m is 0 to 5), —RCO(CH$_2$)$_m$CHCH$_3$CH$_3$, wherein R is NH, m is 0 to 5, —RCOCH$_2$(CH$_2$)$_m$CH$_3$, wherein R is NH, m is 0 to 5, —RCO(CH$_2$)$_m$NR$^4$CH$_3$, wherein R is O or NH, m is 0, $R^4$ is H or $C_{1-6}$ alkyl, $-RSO_2CH_2(CH_2)_mCH_3$, wherein R is NH, m is 0 to 5; or pharmaceutically acceptable salts thereof.

16. The compound according to claim 12, which is selected from the group consisting of
  2.2-[(2E,4E,6E,8E)-3,7-dimethyl-9-(2,6,6-trimethyl-cyclohex-1-enyl)-nona-2,4,6,8-tetraenoylamino]-5-hydroxy-phenyl butanoate(KCBG10);
  5-butyryloxy-2-[3,7-dimethyl-9-(2,6,6-trimethyl-cyclohex-1-enyl)-nona-2,4,6,8-tetraenoylamino]-phenyl butanoate(KCBG09);
  2-[(2E,4E,6E,8E)-3,7-dimethyl-9-(2,6,6-trimethyl-cyclohex-1-enyl)-nona-2,4,6,8-tetraenoylamino]-5-hydroxy-phenyl propionate (KCBG15);
  2-[(2E,4E,6E,8E)-3,7-dimethyl-9-(2,6,6-trimethyl-cyclohex-1-enyl)-nona-2,4,6,8-tetraenoylamino]-5-hydroxy-phenyl-2-oxo-propionate (KCBG22);
  2-[(2E,4E,6E,8E)-3,7-dimethyl-9-(2,6,6-trimethyl-cyclohex-1-enyl)-nona-2,4,6,8-tetraenoylamino]-5-hydroxy-phenyl-(dimethylamino)-acetate(KCBG23);
  2-[(2E,4E,6E,8E)-3,7-dimethyl-9-(2,6,6-trimethyl-cyclohex-1-enyl)-nona-2,4,6,8-tetraenoylamino]-5-hydroxy-phenyl-2-oxobutanoate (KCBG38);
  2-[(2E,4E,6E,8E)-3,7-dimethyl-9-(2,6,6-trimethyl-cyclohex-1-enyl)-nona-2,4,6,8-tetraenoylamino]-5-hydroxy-pbenyl-3-hydroxy-butanoate(KCBG39), or pharmaceutically acceptable salts thereof.

17. The compound according to claim 13, which is selected from the group consisting of
  4-(4-[(2E,4E,6E,8E)-3,7-dimethyl-9-(2,6,6-trimethyl-1-cyclohexenyl)-2,4,6,8-nonatetraenoyl]aminophenoxy)-4-oxobutanoic acid(KCBG32);
  (2E,4E,6E,8E)-[3,7-dimethyl-9-(2,6,6-trimethyl-cyclohex-1-enyl)-nona-2,4,6,8-tetraenoylamino]-(4-butyrylamino)-phenylamide (KCBG40);
  4-[(2E,4E,6E,8E)-3,7-dimethyl-9-(2,6,6-trimethyl-1-cyclohexenyl)-2,4,6,8-nonatetraenoyl]aminophenyl-1-butanesulfonate(KCBG43);
  4-[(2E,4E,6E,8E)-3,7-dimethyl-9-(2,6,6-trimethyl-1-cyclohexenyl)-2,4,6,8-nonatetraenoyl]aminophenyl-2-oxopropanoate(KCBG45);
  4-[(2E,4E,6E,8E)-3,7-dimethyl-9-(2,6,6-trimethyl-1-cyclohexenyl)-2,4,6,8-nonatetraenoyl]aminophenyl-2-oxobutanoate(KCBG47);
  4-(4-[(2E,4E,6E,8E)-3,7-dimethyl-9-(2,6,6-trimethyl-1-cyclohexenyl)-2,4,6,8-nonatetraenoyl]aminophenoxy) 4-oxobutanoic acid(KCBG50);
  4-(4[(2E,4E,6E,8E)-3,7-dimethyl-9-(2,6,6-trimethyl-1-cyclohexenyl)-2,4,6,8-nonatetraenoyl]aminophenoxy)-oxo-hexandioic acid(KCBG51);
  4-[(2E,4E,6E,8E)-3,7-dimethyl-9-(2,6,6-trimethyl-cyclohex-1-enyl)-nona-2,4,6,8-tetraenoylamino]-phenyl-2-acetylamino-4-carbamoyl-butanoate(KGBG52);
  4-(4-[(2E,4E,6E,8E)-3,7-dimethyl-9-(2,6,6-trimethyl-1-cyclohexenyl)-2,4,6,8-nonatetraenoyl]aminophenoxy)-oxo-peptandioic acid(KCBG53); and
  4-(4-[(2E,4E,6E,8E)-3,7-dimethyl-9-(2,6,6-trimethyl-1-cyclohexenyl)-2,4,6,8-nonatetraenoyl]aminophenoxy)-oxo-octandionic acid (KCBG54), or pharmaceutically acceptable salts thereof.

\* \* \* \* \*